(12) United States Patent
Korinek et al.

(10) Patent No.: US 12,239,654 B2
(45) Date of Patent: Mar. 4, 2025

(54) COMPOUNDS AND METHODS FOR TREATING NEUROLOGICAL AND CARDIOVASCULAR CONDITIONS

(71) Applicants: Astrocyte Pharmaceuticals, Inc., Cambridge, MA (US); Board of Regents, the University of Texas System, Austin, TX (US); The United States of America, as Represented by the Secretary, Department of Health and Human Services, Bethesda, MD (US)

(72) Inventors: William S. Korinek, Mystic, CT (US); James D. Lechleiter, San Antonio, TX (US); Theodore E. Liston, Stonington, CT (US); Kenneth A. Jacobson, Silver Spring, MD (US)

(73) Assignees: Astrocyte Pharmaceuticals, Inc., Cambridge, MA (US); Board of Regents, The University of Texas System, Austin, TX (US); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 1230 days.

(21) Appl. No.: 16/095,282

(22) PCT Filed: Apr. 21, 2017

(86) PCT No.: PCT/US2017/028996
§ 371 (c)(1),
(2) Date: Oct. 19, 2018

(87) PCT Pub. No.: WO2017/185061
PCT Pub. Date: Oct. 26, 2017

(65) Prior Publication Data
US 2022/0305044 A1 Sep. 29, 2022

Related U.S. Application Data

(60) Provisional application No. 62/325,860, filed on Apr. 21, 2016.

(51) Int. Cl.
*A61K 31/7076* (2006.01)
*A61K 31/52* (2006.01)
*A61P 25/00* (2006.01)

(52) U.S. Cl.
CPC .......... *A61K 31/7076* (2013.01); *A61K 31/52* (2013.01); *A61P 25/00* (2018.01)

(58) Field of Classification Search
CPC ..... A61K 31/7076; A61K 31/52; A61P 25/00; A61P 9/00; A61P 9/10; A61P 25/28; A61P 25/16
See application file for complete search history.

(56) References Cited

U.S. PATENT DOCUMENTS

| | | |
|---|---|---|
| 5,773,423 A | 6/1998 | Jacobson et al. |
| 6,586,413 B2 | 7/2003 | Liang et al. |
| 7,064,112 B1 | 6/2006 | Fishman |
| 7,087,589 B2 | 8/2006 | Jacobson et al. |
| 7,348,315 B2 | 3/2008 | Liang et al. |
| 7,414,036 B2 | 8/2008 | Sevillano et al. |
| 7,476,709 B2 | 1/2009 | Moody et al. |
| 7,589,075 B2 | 9/2009 | Fishman et al. |
| 7,790,735 B2 | 9/2010 | Jacobson et al. |
| 7,825,126 B2 | 11/2010 | Jacobson et al. |
| 7,867,983 B2 | 1/2011 | Liang et al. |
| 8,399,018 B2 | 3/2013 | Lichter et al. |
| 8,410,078 B2 | 4/2013 | Liang et al. |
| 8,518,957 B2 | 8/2013 | Jacobson et al. |
| 8,685,372 B2 | 4/2014 | Tsien et al. |
| 8,691,775 B2 | 4/2014 | Wurtman |
| 8,735,407 B2 | 5/2014 | Jacobson et al. |
| 8,796,291 B2 | 8/2014 | Jacobson et al. |
| 8,822,434 B2 | 9/2014 | Liang et al. |
| 8,916,570 B2 | 12/2014 | Jacobson et al. |
| 9,132,087 B2 | 9/2015 | Lichter et al. |
| 9,132,131 B2 | 9/2015 | Salvemini |
| 9,181,253 B2 | 11/2015 | Jacobson et al. |
| 9,387,220 B2 | 7/2016 | Fishman et al. |
| 9,526,739 B2 | 12/2016 | Liang et al. |
| 9,789,131 B1 | 10/2017 | Korinek et al. |
| 9,963,450 B2 | 5/2018 | Jacobson et al. |
| 10,265,338 B2 | 4/2019 | Korinek et al. |
| 10,953,031 B2 | 3/2021 | Korinek et al. |
| 11,324,769 B2 | 5/2022 | Poe et al. |

(Continued)

FOREIGN PATENT DOCUMENTS

| | | |
|---|---|---|
| CN | 1946732 A | 4/2007 |
| CN | 109666053 A | 4/2019 |

(Continued)

OTHER PUBLICATIONS

U.S. Appl. No. 16/353,737, filed Mar. 14, 2019 (146 pages).
U.S. Appl. No. 16/583,570, filed Sep. 26, 2019 (96 pages).
Ando et al., "A comparative analysis of the activity of ligands acting at P2X and P2Y receptor subtypes in models of neuropathic, acute and inflammatory pain, " British Journal of Pharmacology, vol. 159, No. 5, Mar. 2010 (pp. 1106-1117).
Armstrong et al., "Adenosine receptor specificity in preconditioning of isolated rabbit cardiomyocytes: evidence of $A_3$ receptor involvement," Cardiovascular Research, vol. 28, No. 7, Jul. 1994 (pp. 1049-1056).
Auchampach et al., "Selective Activation of $A_3$ Adenosine Receptors with $N^6$-(3-Iodobenzyl)Adenosine-5'-N-Methyluronamide Protects Against Myocardial Stunning and Infarction without Hemodynamic Changes in Conscious Rabbits," Circulation Research, vol. 80, Jun. 1997 (pp. 800-809).

(Continued)

*Primary Examiner* — Sahar Javanmard
(74) *Attorney, Agent, or Firm* — Dechert LLP; Andrea L. C. Reid; Joseph W. Arico

(57) ABSTRACT

The present invention relates to compounds and methods of use thereof for treatment of certain disorders and conditions, for example brain injuries such as stroke or traumatic brain injuries.

11 Claims, 20 Drawing Sheets

(56) References Cited

U.S. PATENT DOCUMENTS

| | | | |
|---|---|---|---|
| 11,484,545 | B2 | 11/2022 | Korinek et al. |
| 11,839,615 | B2 | 12/2023 | Korinek et al. |
| 2003/0216412 | A1 | 11/2003 | Jacobson et al. |
| 2009/0088403 | A1 | 4/2009 | Blakely et al. |
| 2009/0306225 | A1 | 12/2009 | Lichter et al. |
| 2010/0047798 | A1 | 2/2010 | Feldman et al. |
| 2010/0197914 | A1 | 8/2010 | Fairhurst |
| 2010/0256086 | A1 | 10/2010 | Fischer |
| 2011/0046166 | A1* | 2/2011 | Jacobson ............ A61P 9/00 514/263.2 |
| 2014/0241990 | A1 | 8/2014 | Haydon et al. |
| 2015/0087613 | A1 | 3/2015 | Salvemini |
| 2016/0024135 | A1 | 1/2016 | Chai et al. |
| 2017/0002007 | A1 | 1/2017 | Jacobson et al. |
| 2018/0021363 | A1 | 1/2018 | Korinek et al. |
| 2019/0225615 | A1 | 7/2019 | Casale et al. |
| 2020/0004675 | A1 | 2/2020 | Korinek et al. |
| 2020/0009384 | A1 | 3/2020 | Poe et al. |
| 2021/0077518 | A1 | 3/2021 | Poe et al. |
| 2022/0305044 | A1 | 9/2022 | Korinek et al. |
| 2023/0165887 | A1 | 6/2023 | Korinek et al. |

FOREIGN PATENT DOCUMENTS

| | | |
|---|---|---|
| EP | 1624753 A2 | 2/2006 |
| JP | 2003-519698 A | 6/2003 |
| WO | 2003051881 A1 | 6/2003 |
| WO | WO-2004047749 | 6/2004 |
| WO | 2005063246 A1 | 7/2005 |
| WO | 2006031505 A1 | 3/2006 |
| WO | WO-2006091905 A1 | 8/2006 |
| WO | WO-2007020018 A1 | 2/2007 |
| WO | WO-2008021552 A2 | 2/2008 |
| WO | 2009018871 A1 | 2/2009 |
| WO | WO-2010014921 A2 | 2/2010 |
| WO | WO-2011077435 A1 | 6/2011 |
| WO | WO-2014160502 A1 | 10/2014 |
| WO | 2015080940 A1 | 6/2015 |
| WO | WO-2016123672 A1 | 8/2016 |
| WO | 2017185061 A1 | 10/2017 |
| WO | WO-2019157317 A1 | 8/2019 |
| WO | 2020069068 A1 | 4/2020 |
| WO | 2021021717 A1 | 2/2021 |
| WO | 2022232810 A1 | 11/2022 |
| WO | 2023091791 A1 | 5/2023 |

OTHER PUBLICATIONS

Baltos et al., "Structure-Activity Analysis of Biased Agonism at the Human Adenosine $A_3$ Receptor," Molecular Pharmacology, vol. 90, No. 1, Jul. 2016 (pp. 12-22).

Barragán-Iglesias et al., "Participation of Peripheral $P2Y_1$, $P2Y_6$ and $P2Y_{11}$ receptors in formalin-induced inflammatory pain in rats," Pharmacology, Biochemistry and Behavior, vol. 128, Jan. 2015 (pp. 23-32).

Ben et al., "Different efficacy of adenosine and NECA derivatives at the human $A_3$ adenosine receptor: insight into the receptor activation switch," Biochemical Pharmacology, vol. 87, No. 2, Jan. 2014 (pp. 321-331).

Beukers et al., "New, non-adenosine, high-potency agonists for the human adenosine A2B receptor with an improved selectivity profile compared to the reference agonist N-ethylcarboxamidoadenosine," Journal of Medicinal Chemistry, vol. 47, No. 15, Jul. 2004 (pp. 3707-3709).

Björklund et al., "Adenosine $A_1$ and $A_3$ receptors protect astrocytes from hypoxic damage," European Journal of Pharmacology, vol. 596, No Month Listed 2008 (pp. 6-13).

Borea et al., "The $A_3$ Adenosine Receptor: History and Perspectives," Pharmacological Reviews, vo. 67, Jan. 2015 (pp. 74-102).

Bourdon et al., "(N)-methanocarba-2MeSADP (MRS2365) is a subtype-specific agonist that induces rapid desensitization of the $P2Y_1$, receptor of human platelets," Journal of Thrombosis and Haemostasis, vol. 4, No. 4, Apr. 2006 (pp. 861-868).

Camaioni et al., "Adenosine receptor agonists: synthesis and biological evaluation of the disatereoisomers of 2-(3-hydroxy-3-phenyl-1-propyn-1-yl)NECA," Bioorganic & Medicinal Chemistry, vol. 5, No. 12, Dec. 1997 (pp. 2267-2275).

Chen et al., "Activation of Adenosine A3 Receptors Reduces Ischemic Brain Injury in Rodents," Journal of Neuroscience Research, vol. 84, No Month Listed 2006 (pp. 1848-1855).

Choi et al., "A3 Adenosine Receptor Agonist Reduces Brain Ischemic Injury and Inhibits Inflammatory Cell Migration in Rats," The America Journal of Pathology, vol. 179, No. 4, Oct. 2011 (pp. 2042-2052).

Ciancetta et al., "Structural Probing and Molecular Modeling of the $A_3$ Adenosine Receptor: A Focus on Agonist Binding," Molecules, vol. 22, No. 3, Mar. 2017 (17 pages).

Cosyn et al., "2-Triazole-Substituted Adenosines: A New Class of Selective $A_3$ Adenosine Receptor Agonists, Partial Agonists, and Antagonists," The Journal of Medicinal Chemistry, vol. 49, No. 25, Dec. 2006 (pp. 7373-7383).

Cosyn et al., "Synthesis of hypermodified adenosine derivatives as selective adenosine $A_3$ receptor ligands," Bioorganic & Medicinal Chemistry, vol. 14, 2006 (pp. 1403-1412) (Nov. 2005).

Cristalli et al., "2-Aralkynyl and 2-Heteroalkynyl derivatives of adenosine-5'-N-ethyluronamide as selective A2a adenosine receptor agonists," Journal of Medicinal Chemistry, vol. 38, No. 9, Apr. 1995 (pp. 1462-1472).

D'Alimonte et al., "Potentiation of temozolomide antitumor effect by purine receptor ligands able to restrain the in vitro growth of human glioblastoma stem cells," Purinergic Signalling, vol. 11, No. 3, Sep. 2015 (pp. 331-346).

Devine et al., "Synthesis and evaluation of new $N^6$-substituted adenosine-5'-N-methylcarboxamides as $A_3$ adenosine receptor agonists," Bioorganic & Medicinal Chemistry, vol. 18, No. 8, May 2010 (pp. 3078-3087).

Doyle et al., "Adenosine $A_3$ Receptor Expression and Function in Mitochondria," The FASEB Journal, vol. 30, No. 1, Apr. 2016, Supplement 1266.6 (2 pages).

Fedorova et al., "Behavioral Characterization of Mice Lacking the $A_3$ Adenosine Receptor: Sensitivity to Hypoxic Neurodegeneration," Cell Molecular Neurobiology, vol. 23, No. 3, Jun. 2003 (pp. 431-447).

Gao et al., "Allosteric modulation and functional selectivity of G protein-coupled receptors," Drug Discovery Today. Technologies, vol. 10, no. 2, No Month Listed 2013 (pp. e237-e243).

Gao et al., "Functionally biased modulation of $A_3$ adenosine receptor agonist efficacy and potency by imidazoquinolinamine allosteric enhancers," Biochemical Pharmacology, vol. 82, No. 6, Sep. 2011 (pp. 658-668).

Gao et al., "Partial Agonists for $A_3$ Adenosine Receptors," Current Topics in Medicinal Chemistry, vol. 4, No. 8, Apr. 2004 (pp. 855-862).

Gao et al., "Structural Determinants of $A_3$ Adenosine Receptor Activation: Nucleoside Ligands at the Agonist/Antagonist boundary," Journal of Medicinal Chemistry, vol. 45, No. 20, Aug. 2002 (pp. 4471-4484).

Gundry et al., "A Practical Guide to Approaching Biased Agonism at G Protein Coupled Receptors," Frontiers in Neuroscience, vol. 11, No. 17, Jan. 2017 (6 pages).

International Preliminary Report on Patentability issued by the United States Patent and Trademark Office as International Searching Authority for International Patent Application No. PCT/US2017/028996 mailed Nov. 1, 2018 (8 pages).

International Search Report and Written Opinion issued by the United States Patent and Trademark Office as International Searching Authority for International Patent Application No. PCT/US2017/028996 mailed Aug. 2, 2017 (10 pages).

Jacobson et al., "Medicinal Chemistry of the $A_3$ Adenosine Receptor: Agonists, Antagonists, and Receptor Engineering," Handbook Experimental Pharmacology, vol. 193, No Month Listed 2009 (pp. 123-159).

(56) References Cited

OTHER PUBLICATIONS

Jacobson et al., "P2Y nucleotide receptors: Promise of therapeutic applications," Drug Discovery Today, vol. 15, Nos. 13-14, Jul. 2010 (pp. 570-578).
Jacobson et al., "John Daly Lecture: Structure-guided Drug Design for Adenosine and. P2Y Receptors," Computational and Structural Biotechnology Journal, vol. 13, Oct. 2014 (pp. 286-298).
Kim et al., "Three-dimensional quantitative structure-activity relationship of nucleosides acting at the $A_3$ adenosine receptor: analysis of binding and relative efficacy," Journal of Chemical Information and Modeling, vol. 47, No. 3, May 2007 (pp. 1225-1233).
Klotz et al., "2-substituted N-ethylcarboxamidoadenosine derivatives as high-affinity agonists as human $A_3$ adenosine receptors," Naunyn-Schmiedeberg's Archives of Pharmacology, vol. 360, No. 2, Aug. 1999 (pp. 103-108).
Koch et al., "Impaired Cognition after Stimulation of $P2Y_1$ Receptors in the Rat Medial Prefrontal Cortex," Neuropsychopharmacology, vol. 40, No. 2, Jan. 2015 (pp. 305-314).
Kumar et al., "5'-Phosphate and 5'-Phosphonate Ester Derivatives of (N)-Methanocarba Adenosine with in Vivo Cardioprotective Activity," Journal of Medicinal Chemistry, vol. 56, No. 3, Jan. 2013 (pp. 902-914).
Kwon et al., "Blockade of Peripheral $P2Y_1$ Receptors Prevents the Induction of Thermal Hyperalgesia via Modulation of $TRPV_1$ Expression in Carrageenan-Induced Inflammatory Pain Rats: Involvement of p38 MAPK Phosphorylation in DRGs," Neuropharmacology, vol. 79, Dec. 2013 (pp. 368-379).
Lee et al., "Ring-Constrained (N)-Methanocarba Nucleosides as Adenosine Receptor Agonists: Independent 5'-Uronamide and 2'-Deoxy Modifications," Bioorganic & Medicinal Chemistry Letters, vol. 11, No Month Listed 2001 (pp. 1333-1337).
Lewerenz et al., "A3 Receptors in Cortical Neurons: Pharmacological Aspects and Neuroprotection during Hypoxia," Drug Development Research, vol. 58, No. Month Listed 2003 (pp. 420-427).
Liang et al., "A physiological role of the adenosine $A_3$ receptor: Sustained cardioprotection," The Proceedings of the National Academy of Science, U.S.A., vol. 95, No. 12, Jun. 1998 (pp. 6995-6999).
Little et al., "Endogenous adenosine A3 receptor activation selectively alleviates persisent pain states," Brain Advance Access published Nov. 19, 2015; (pp. 1-8).
Lubitz et al., "Adenosine A3 receptor stimulation and cerebral ischemia," European Journal of Pharmacology, vol. 263, No Month Listed 1994 (pp. 59-67).
Lubitz et al., "Chronic administration of adenosine $A_3$ receptor agonist and cerebral ischemia: neuronal and glial effects," European Journal of Pharmacology, vol. 367, No Month Listed 1999 (pp. 157-163).
Lubitz et al., "Right Thing at a Wrong Time? Adenosine $A_3$ Receptors and Cerebroprotection in Stroke," Annals New York Academy of Sciences, Neuroprotective Agents: Fifth International Conference, vol. 939, Jun. 2001 (pp. 85-96).
Mañé et al., "Differential functional role of purinergic and nitrergic inhibitory co-transmitters in human colonic relaxation," Acta Physiologica, vol. 212, No. 4, Oct. 2014 (pp. 293-305).
Müller et al., "Recent developments in adenosine receptor ligands and their potential as novel drugs," Biochimica et Biophysica Acta, vol. 1808, vol. 5, May 2011 (pp. 1290-1308).
Nayak et al., "Synthesis and Anti-Renal Fibrosis Activity of Conformationally Locked Truncated 2-Hexynyl-$N^6$-Substituted-(N)-Methanocarba-nucleosides as $A_3$ Adenosine Receptor Antagonists and Partial Agonists," Journal of Medicinal Chemistry, vol. 57, No. 4, Jan. 2014 (pp. 1344-1354).
Paoletta et al., "Rational Design of Sulfonated $A_3$ Adenosine Receptor-Selective Nucleosides as Pharmacological Tools to Study Chronic Neuropathic Pain," Journal of Medicinal Chemistry, vol. 56, No. 14, Jun. 2013 (pp. 5949-5963).
Perreira et al., "'Reversine' and its 2-Substituted Adenine Derivates as Potent and Selective A3 Adenosine Receptor Antagonists," The Journal of Medicinal Chemistry, vol. 48, No. 15, Jul. 2005 (pp. 4910-4918).

Pubchem, "Compound Summary for CID 69572716, SCHEMBL5803724," retrieved from https://pubchem.ncbi.nlm.nih.gov/compound/69572716#section=Top>> accessed on Mar. 17, 2017 (10 pages).
Pugliese et al., "Role of adenosine $A_3$ receptors on CA1 hippocampal neurotransmission during oxygen-glucose deprivation episodes of different duration," Biochemical Pharmacology, vol. 74, No. 5, Sep. 2007 (pp. 768-779).
Ravi et al., "Adenine Nucleotide Analogues Locked in a Northern Methanocarba Conformation: Enhanced Stability and Potency as $P2Y_1$ Receptor Agonists," Journal of Medicinal Chemistry, vol. 45, No. 10, May 2002 (pp. 2090-2100).
Tamada et al., "Calcium responses in subserosal interstitial cells of the guinea-pig proximal colon," Neurogastroenterology and motility: the official journal of the European Gastrointestinal Motility Society, vol. 26, No. 1, Jan. 2014 (pp. 115-123).
Tosh et al., "Click Modification in the $N^6$ Region of $A_3$ Adenosine Receptor-Selective Carbocyclic Nucleosides for Dendrimeric Tethering that Preserves Pharmacophore Recognition," Bioconjugate Chemistry, vol. 23, No. 2, Feb. 2012 (pp. 232-247).
Tosh et al., "Structural Sweet Spot for $A_1$ Adenosine Receptor Activation by Truncated (N)-Methanocarba Nucleosides: Receptor Docking and Potent Anticonvulsant Activity," Journal of Medicinal Chemistry, vol. 55, No. 18, Sep. 2012 (pp. 8075-8090).
Tosh et al., "Methanocarba ring as a ribose modification in ligands of G protein-coupled purine and pyrimidine receptors: synthetic approaches," MedChemComm, vol. 2013, No. 4, Dec. 2013 (pp. 619-630).
Toti et al., "Synthesis and Evaluation of $N^6$-Substituted Apioadenosines as Potential Adenosine $A_3$ Receptor modulators," Bioorganic & Medicinal Chemistry Journal, vol. 22, No. 15, Aug. 2014 (pp. 4257-4268).
Tracey et al., "Novel $N^6$-substituted adenosine 5'-N-methyluronamindes with high selectivity for human adenosine A3 receptors reduce ischemic myocardial injury," American Journal of Physiology Heart and Circulatory Physiology, vol. 285, No. 6, Dec. 2003 (pp. H2780-H2787).
Verzijl et al., "Functional selectivity of adenosine receptor ligands," Purinergic Signalling, vol. 7, May 2011 (pp. 171-192).
Volpini et al., "Synthesis and biological evaluation of 2-alkynyl-$N^6$-methyl-5'-N-methylcarboxamidoadenosine derivatives as potent and highly selective agonists for the human adenosine $A_3$ receptor," Journal of Medicinal Chemistry, vol. 52, No. 23, Dec. 2009 (pp. 7897-7900).
Wan et al., "The $A_3$ adenosine receptor agonist CP-532,903 [$N^6$-(2,5-dichlorobenzyl)-3'-aminoadenosine-5'-N-methylcarboxamide] protects against myocardial ischemia/reperfusion injury via the sarcolemmal ATP-sensitive potassium channel," Journal of Pharmacology and Experimental Therapeutics, vol. 324, No. 1, Jan. 2008 (pp. 234-243).
Warden et al., "Guidelines for the pharmacologic treatment of neurobehavioral sequelae of traumatic brain injury," Journal of Neurotrauma, vol. 23, No. 10, Oct. 2006 (pp. 1468-1501).
Wei et al., "Activation of the $P2Y_1$ receptor induces apoptosis and inhibits proliferation of prostate cancer cells," Biochemical Pharmacology, vol. 82, No. 4, Aug. 2011 (pp. 418-425).
Wong et al., "Post exposure administration of A1 adenosine receptor agonists attenuates noise-induced hearing loss", Hearing Research, vol. 260, 2010 (pp. 81-88).
Ziganshin et al., "Characteristics of ecto-ATPase of Xenopus oocytes and the inhibitory actions of suramin on ATP breakdown," Pflugers Archiv: European journal of physiology, vol. 429, No. 3, Jan. 1995 (pp. 412-418).
Gillerman et al., "Investigations into the Origin of the Molecular Recognition of Several Adenosine Deaminase Inhibitors," J. Med. Chem. 2011; 54(1):107-121.
Brittain, "Polymorphism in Pharmaceutical Solids," Marcel Dekker Inc., 1999; 183-226.
Goadsby et al., "Adenosine A1 receptor agonists inhibit trigeminovascular nociceptive transmission," Guarantors of Brain, 2002 (pp. 1392-1401).

(56) References Cited

OTHER PUBLICATIONS

International Search Report and Written Opinion for PCT/US2017/028996, mailed by the U.S. Patent and Trademark Office on Aug. 2, 2017 (10 pages).
International Search Report and Written Opinion for PCT Application No. PCT/US2022/071971, mailed by the U.S. Patent and Trademark Office on Aug. 24, 2022 (14 Pages).
Jacobson et al., "Historical and Current Adenosine Receptor Agonists in Preclinical and Clinical Development," Front Cell Neurosci., 2019, vol. 13, No. 124, 17 pages.
Mayo Clinic Staff, "Compulsive Gambling—Diagnosis", Mayo Foundation for Medical Education and Research (MFMER), (Oct. 22, 2016), p. 1, URL: https://www.mayoclinic.org/diseases-conditions/compulsive-gambling/diagnosis-treatment/drc-20355184.
Mayo Clinic Staff, "Compulsive Gambling—Symptoms", Mayo Foundation for Medical Education and Research (MFMER), (Oct. 22, 2016), p. 1, URL: https://www.mayoclinic.org/diseases-conditions/compulsive-gambling/symptoms-causes/syc-20355178.
Mañé et al., "BPTU, an allosteric antagonist of P2Y1 receptor, blocks nerve mediated inhibitory neuromuscular responses in the gastrointestinal tract of rodents," Neuropharmacology. 2016; 110(Pt A): 376-385.
PubChem-CID-11623975, Create Date: Oct. 26, 2006, p. 2.
Vippagunta et al., "Crystalline solids," Adv Drug Deliv Rev. 2001; 48(1): 3-26.
U.S. Appl. No. 17/934,169, filed Sep. 21, 2022.
Augustijns et al., ed., Solvent Systems and Their Selection in Pharmaceutics and Biopharmaceutics, 2007, American Association of Pharmaceutical Scientists, Springer, 2007, pp. 53-109.
Byrn et al., "Pharmaceutical Solids: A Strategic Approach to Regulatory Considerations," Pharmaceutical Research, 1995, vol. 12, No. 7, pp. 945-954.
CDC, Types of Stroke, https://web.archive.org/web/20150315064531/http://www.cdc.gov/stroke/types_of_stroke.htm; 2013.
Choi et al., "Preparative and Stereoselective Synthesis of the Versatile Intermediate for Carbocyclic Nucleosides: Effects of the Bulky Protecting Groups to Enforce Facial Selectivity," J. Org. Chem. 2004; 69(7): 2634-2636.
Yamano, "Approach to Crystal Polymorph in Process Research of New Drug," Journal of Synthetic Organic Chemistry, Sep. 1, 2007, vol. 65, No. 9, pp. 907-913.
Wu et al., "Purinergic receptor-stimulated IP3-mediated Ca2+ release enhances neuroprotection by increasing astrocyte mitochondrial metabolism during aging," J Neurosci. 2007; 27(24): 6510-20.
Hirayama, "Handbook for Preparation of Organic Compound Crystals," Maruzen Inc., Jul. 25, 2008, pp. 57-84.
Wootten et al., "Differential activation and modulation of the glucagon-like peptide-1 receptor by small molecule ligands," Mol Pharmacol. 2013; 83:822-834.
Van der Westhuizen et al., "Quantification of ligand bias for clinically relevant b2-adrenergic receptor ligands: im-plications for drug taxonomy," Mol Pharmacol. 2014; 85:492-509.
Tosh et al., "Truncated nucleosides as A3 adenosine receptor ligands: Combined 2-arylethynyl and bicyclohex-ane substitutions," ACS Med Chem Lett. 2012; 3:596-601.
Kawaguchi et al., "Drug and Crystal Polymorphism," Journal of Human Environmental Engineering, 2002, vol. 4, No. 2, pp. 310-317.
Kenakin et al., "A simple method for quantifying functional selectivity and agonist bias," ACS Chem Neurosci. 2012; 3:193-203.
Klotz, "Adenosine receptors and their ligands," Naunyn Schmiedebergs Arch Pharmacol. 2000; 362(4-5): 382-391.
Tosh et al., "Structure-guided design of A3 adenosine receptor-selective nucleosides: combination of 2-arylethynyl and bicyclo[3.1.0]hexane sub-stitutions," J Med Chem. 2012; 55:4847-4860.
Lin et al., "Ca2+ signaling, mitochondria and sensitivity to oxidative stress in aging astrocytes," Neurobiol Aging. 2007; 28(1): 99-111.
Liston et al., "Nucleotide P2Y, receptor agonists are in vitro and in vivo prodrugs of A1/A3 adenosine receptor agonists . . . ," Purinergic Signalling, 2020; 16; 543-559.
May et al., "Structure-function studies of allosteric agonism at M2 muscarinic acetylcholine receptors," Mol Pharmacol. 2007; 72:463-476.
McCall et al., "Selective Ablation of GIRK Channels in Dopamine Neurons Alters Behavioral Effects of Cocaine in Mice," Neuropsychopharmacology. 2017; 42(3): 707-715.
McCarthy et al., "Preparation of separate astroglial and oligodendroglial cell cultures from rat cerebral tissue," J Cell Biol. 1980; 85(3): 890-902.
Michel et al., "Total syntheses of a conformationally locked North-type methanocarba puromycin analogue and a dinucleotide derivative," Chemistry. 2009; 15(25):6244-57.
Tosh et al., "Efficient, large-scale synthesis and preclinical studies of MRS5698, a highly selective A3 adenosine receptor agonist that protects against chronic neuropathic pain," Purinergic Signalling. 2015; 11(3): 371-387.
Shiniyakuhin, "Setting of the Standard and Test Method for New Pharmaceuticals," Iyakushinpatsu No. 568, May 1, 2001.
Stewart et al. "Determination of adenosine A1 receptor agonist and antagonist pharmacology using *Saccharomyces cerevisiae*: implications for ligand screening and functional selectivity," J Pharmacol Exp Ther. 2009; 331:277-286.
Takata, "API Form Screening and Selection in Drug Discovery Stage," Pharm Stage, vol. 6, No. 10, Jan. 15, 2007, pp. 20-25.
International Search Report for PCT Application No. PCT/US2019/017265, mailed by the U.S. Patent and Trademark Office on May 7, 2019.
International Search Report for PCT Application No. PCT/US2019/053076, mailed by the U.S. Patent and Trademark Office on Dec. 13, 2019 (8 pages).
International Search Report for PCT Application No. PCT/US2022/050743, mailed by the U.S. Patent and Trademark Office on Mar. 3, 2023.
International Search Report for PCT Application No. PCT/US2022/071971, mailed by the U.S. Patent and Trademark Office on Aug. 24, 2022 (14 Pages).

\* cited by examiner

MRS4322 Plasma & Brain Concentration vs Time Profiles in Mice

MRS4322 Plasma & Brain Concentration vs Time Profiles in Neonatal Pigs

MRS2365 and MRS2365 Monophosphate Percent Observed v Time
Following Incubation with Male CD-1 Mouse EDTA-Treated Plasma at 37°C MRS2365 and MRS2365 Monophosphate Percent Observed v Time
Following Incubation with Male CD-1 Mouse EDTA-Treated Whole Blood at 37°C

MRS 2365
Chemical Formula: $C_{13}H_{19}N_5O_9P_2S$
Exact Mass: 483.0379

M2
Chemical Formula: $C_{13}H_{18}N_5O_6PS$
Exact Mass: 403.0715
MRS2347

M1
Chemical Formula: $C_{13}H_{17}N_5O_3S$
Exact Mass: 323.1052
MRS4322

Brain and Cerebrospinal Fluid Concentration-Time Profiles of MRS4322 in Neonatal Pigs
Following Intravenous Administration Competition binding experiments of MRS4322 at <u>human</u> A3 receptors Competition binding experiments of MRS4322 at mouse A3 receptors cAMP accumulation experiments of MRS4322 and NECA at <u>human</u> A3 receptors cAMP accumulation experiments of MRS4322 and NECA at <u>mouse</u> A3 receptors

COMPOUNDS AND METHODS FOR TREATING NEUROLOGICAL AND CARDIOVASCULAR CONDITIONS

CROSS-REFERENCE TO RELATED APPLICATIONS

This application claims the benefit of U.S. Provisional Application No. 62/325,860, filed on Apr. 21, 2016, the entirety of which is hereby incorporated by reference.

STATEMENT OF GOVERNMENT SUPPORT

This invention was made with government support under grant no. NS093756 awarded by the National Institutes of Health. The government has certain rights in the invention.

FIELD OF THE INVENTION

The present invention relates to compounds and methods of use thereof for treating, ameliorating, or promoting recovery from certain conditions of the brain, central nervous system (CNS), or cardiovascular system such as a brain injury, a neurodegenerative condition, or cardiac ischemia.

BACKGROUND OF THE INVENTION

Brain injuries are a distressingly common medical condition and one of the leading causes of morbidity and mortality worldwide. The brain is particularly susceptible to injury as neurons have a limited capacity to repair. When an individual is born, the brain already has essentially all the neurons it will have in life. Unlike other cells in the body, neurons stop reproducing shortly after birth. If these cells are injured or die, they are not replaced, often culminating in the disabling and largely irreversible degradation of a person's cognitive and sensorimotor capacity. Conditions that result in nerve cell death and damage range from ischemic episodes (e.g., stroke) and trauma, to degenerative disorders (e.g., Alzheimer's disease).

Injury to the Central Nervous System (CNS) is a substantial cause of death and disability worldwide. For example, according to the CDC approximately 1.7 million people sustain a Traumatic Brain Injury (TBI) annually, costing the U.S. economy in excess of $60 billion per year in terms of medical costs and lost productivity (Finkelstein, E; Corso, P; Miller, T, The Incidence and Economic Burden of Injuries in the United States, Oxford University Press: New York, 2006). Additionally, stroke is the third leading cause of death in the U.S. with an estimated incidence of 795,000 cases annually, a major cause of disability, and costing the U.S. economy over $34 billion per year (NINDS, 2014; stroke.n-ih.gov; and Mozaffarian D, Benjamin E J, Go A S, et al. "Heart disease and stroke statistics-2015 update: a report from the American Heart Association," *Circulation*. 2015; e29-322).

In the acute setting, there is an opportunity to treat patients within 24 hours that can limit the extent of the damage. Immediately after an ischemic or hemorrhagic stroke, the site of insult in the brain typically contains a core of tissue that is irreversibly damaged, and then also an area of viable but at-risk tissue called the penumbra. During this period, the insufficient oxygen and glucose supply to brain cells results in further secondary injury to the penumbra. The lack of oxygen and glucose decreases energy production by cell mitochondria. An immediate effect of this energy depletion is failure of the ion pumps, which by elevating extracellular potassium ($K^+$) ions, results in waves of recurrent spreading depolarizations in brain tissue. At the same time, influx of sodium ($Na^+$) ions into cells, followed by chloride ($Cl^-$) ions, results in the swelling of cells due to osmotic pressure elevation, pressuring nearby neurons and their processes, ultimately leading to lysis (cell rupture) and inflammatory responses. In general, this disruption of ion homeostasis leads to excitotoxicity, cell swelling and cell death that extends damage to adjacent tissue and expands lesions by secondary mechanisms. There is a need for effective treatments during the initial 24 hours to protect the stressed brain cells. The propagation of brain damage in stroke is similar to that observed in other forms of brain injury such as trauma and concussions.

Beyond acute treatment, effective astrocyte function plays a key role in broader neurorestoration—in the period 24-96 hours following brain insult, in the period months-years in patients with neurodegeneration such as Alzheimer's, or most generally in aged individuals. The inability of brain cells to regenerate requires the remaining intact brain tissue to reorganize in an attempt to recover any loss of function. This potential for neural reorganization is diminished in older individuals.

GPCR receptors have been suggested to mediate cardioprotective effects. Therefore, there is potential to treat heart and cardiovascular conditions by similar mechanisms of action via modulation of these receptors.

There is urgent and compelling unmet medical need for more effective treatments for brain injuries, CNS injuries, heart and cardiovascular diseases, and related conditions, as well as promoting neurorestoration in patients having a neurodegenerative condition such as Alzheimer's.

SUMMARY OF THE INVENTION

In one aspect, the present invention provides a method of treating an injury, disease, or condition selected from traumatic brain injury (TBI), stroke, a neurodegenerative condition, or a heart or cardiovascular disease, comprising administering to a patient in need thereof an effective amount of an agonist of an $A_3$ adenosine receptor ($A_3R$).

In one aspect, the present invention provides a method of treating an injury, disease, or condition selected from traumatic brain injury (TBI), stroke, a neurodegenerative condition, or a heart or cardiovascular disease, comprising administering to a patient in need thereof an effective amount of a biased agonist, partial agonist, or biased partial agonist of an $A_3$ adenosine receptor ($A_3R$) selected from

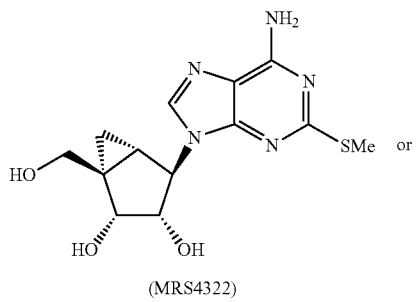

(MRS4322)

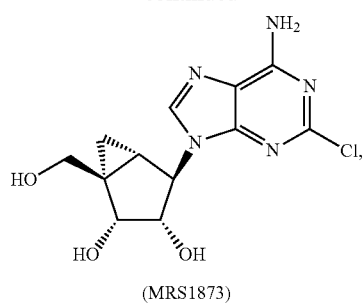

(MRS1873)

a pharmaceutically acceptable salt thereof, or a pharmaceutically acceptable composition comprising the same.

In another aspect, the present invention provides a method of treating a brain or central nervous system (CNS) injury or condition selected from traumatic brain injury (TBI) or stroke, comprising administering to a patient in need thereof an effective amount of a compound selected from:

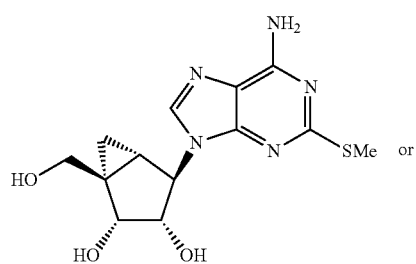 or

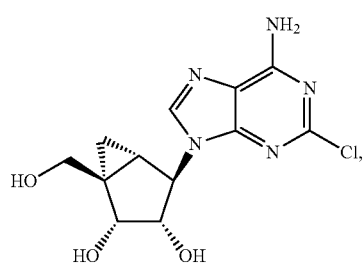, a pharmaceutically acceptable salt thereof, or a pharmaceutically acceptable composition comprising the same.

In another aspect, the present invention provides a compound selected from the group consisting of:

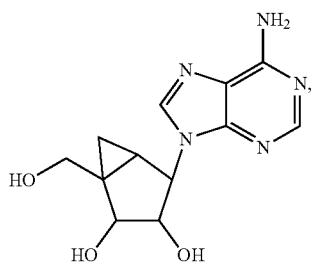,

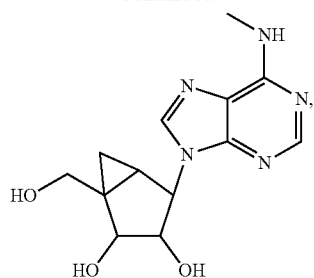,

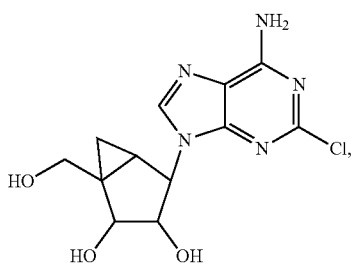,

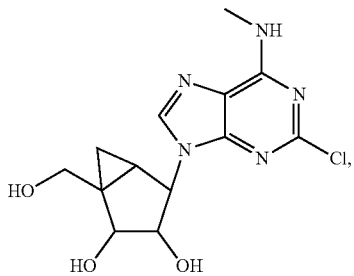,

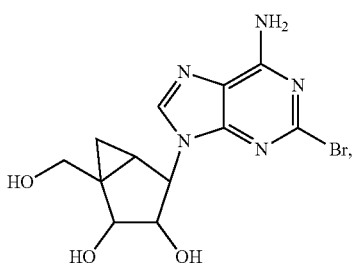,

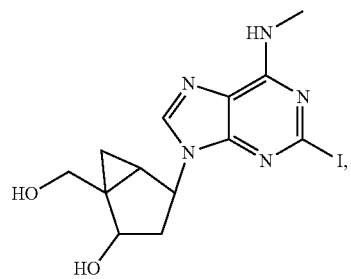,

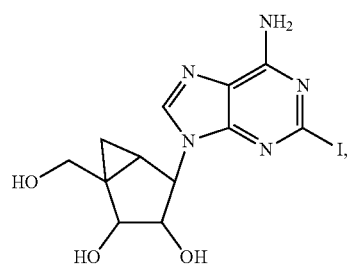,

-continued

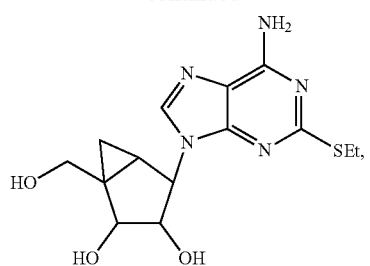
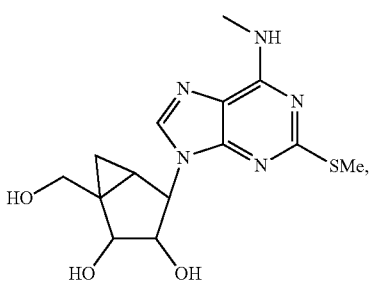
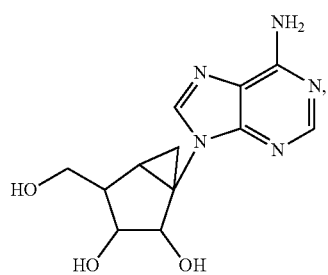
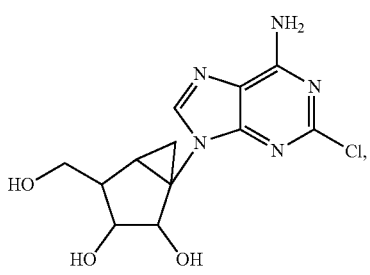
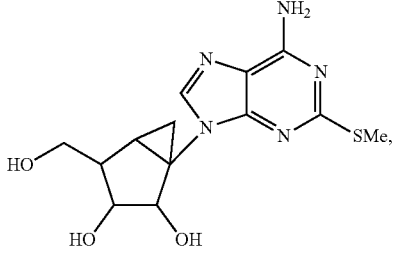
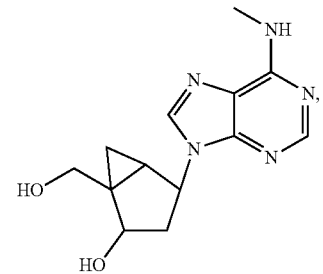

-continued

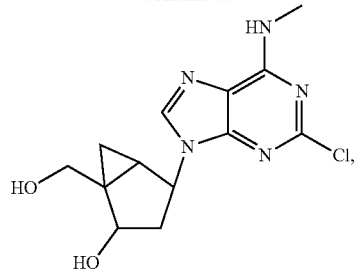
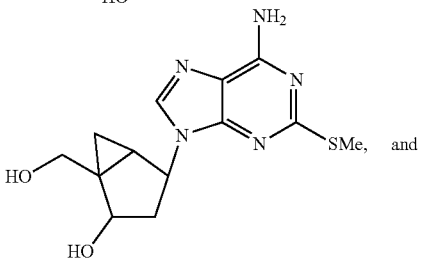 and
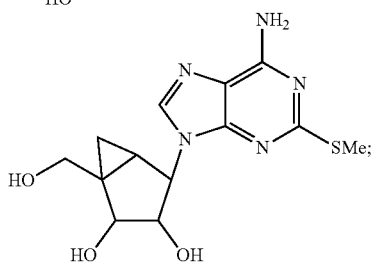

wherein each compound may be in the North or South conformation or the methanocarba sugar may be replaced with a D-ribosugar; or a pharmaceutically acceptable salt thereof; or a mono-, di-, or triphosphate thereof or pharmaceutically acceptable salt of the mono-, di-, or triphosphate.

In another aspect, the present invention provides a method of treating or ameliorating a traumatic brain injury (TBI), radiation damage, stroke, migraine headache, a heart or cardiovascular disease, or neurodegenerative disorder, comprising administering to a patient in need thereof an effective amount of a disclosed compound.

In another aspect, the present invention provides a method of treating or ameliorating a traumatic brain injury (TBI), radiation damage, stroke, migraine headache, a heart or cardiovascular disease, or neurodegenerative disorder, comprising administering to a patient in need thereof an effective amount of a compound selected from: adenosine, ADP, 2-methylthio-ADP trisodium salt, ATP, ATP disodium salt, α,β-methylene ATP, α,β-methyleneadenosine 5'-triphosphate trisodium salt, 2-methylthioadenosine triphosphate tetrasodium salt, 2-MeSATP, BzATP triethylammonium salt, inosine, cytidine, acylated cytidines, cytidine-monophosphate (CMP), cytidine diphosphate (CDP), cytidine triphosphate (CTP), CDP-choline, CMP-choline, denufosol, denufosol tetrasodium, GTP, ITP, MRS 541, MRS 542, MRS 1760, MRS 2179, MRS 2279, MRS 2341, MRS 2365, MRS 2500, MRS 2690, MRS 2698, MRS 3558, MRS 4322, MRS 5151, MRS 5676, MRS 5678, MRS 5697, MRS 5698, MRS 5923, MRS 5930, Benzyl-NECA, IB-MECA, Cl-IB-MECA, LJ529, DPMA, CCPA, DBXRM, HEMADO, PEMADO, HENECA, PENECA, CP608,039, CP532,903, CGS21680, AR132, VT72, VT158, VT160, VT163, PSB 0474, uridine 5'-diphosphate (UDP), UDP-glucose, uridine β-thiodiphosphate (UDPβS), uridine 5'-triphosphate (UTP), uridine γ-thiophosphate (UTPγS), 2-thioUTP tetrasodium salt, UTPγS trisodium salt, uridine-5'-diphosphoglucose, diuridine triphosphate, 2-(hexylthio) (HT)-AMP, diadenosine pentaphosphate, 2'-deoxy-2'-amino-UTP, 2-thio-UTP, triacetyluridine, diacetyl/acyl uridine, uridine, suramin, dipyridamole analogs, diadenosine tetraphosphate $Ap_4U$, $Ap_4A$, INS365, INS37217, or INS48823; wherein each sugar may be replaced with a methanocarba sugar in the North or South conformation or each sugar may be replaced with a D-ribosugar; or a pharmaceutically acceptable salt thereof.

BRIEF DESCRIPTION OF THE FIGURES

(FIGS. 12A and 12C) Representative blots are shown for Ipsilateral brain homogenates and the plasma at day 7. Administration of MRS4322 or MRS2365 decreased brain levels of GFAP expression in mice exposed to TBI. (FIGS. 12B and 12D) Data were pooled from 3 distinct experiments (N=number of mice per treatment) and plotted as bar histograms, shown as mean of control+/−SEM. *$p<0.05$ and **$p<0.01$ from TBI untreated (red bar).

(FIG. 13A) Coronal sections of mouse brains (each group of sections is from a single mouse) stroked with photothrombosis in vehicle (saline injected) and in treated mice, MRS4322, and MRS2365 as labelled. Stroked mice received either vehicle or treatments (IP injections) within 30 minutes of ischemia. Mice were then sacrificed at 24 hours post-stroke, their brains removed, sectioned and stained with TTC. (FIG. 13B) Coronal sections from stroked mice pre-injected with the $A_3$ receptor antagonist MRS1523. (FIG. 13C) Average TTC-stained stroke volumes of MRS4322, MRS2365, MRS5698 and Cl-IBMECA as labeled. (FIG. 13D) Stroke volumes in mice pretreated with the $A_3$ receptor antagonist MRS1523 as indicated. Data were pooled from 2 experiments (N=number of mice per treatment) and plotted as mean+/−SEM. $p<0.01$ and *$p<0.001$.

(FIG. 14A) Coronal sections of brains stroked with photothrombosis in vehicle (saline injected) and in treated mice, MRS4322 and MRS1873 as labelled. Stroked mice received either vehicle or treatments (IP injections) within 30 minutes of ischemia. Mice were then sacrificed at 24 hours post-stroke, their brains removed, sectioned and stained with TTC. (FIG. 14B) Average TTC-stained stroke volumes as labeled. Data were pooled from 3 experiments (N=number of mice per treatment) and plotted as mean+/−SEM. **$p<0.01$.

DETAILED DESCRIPTION OF CERTAIN EMBODIMENTS OF THE INVENTION

Figure 1A:
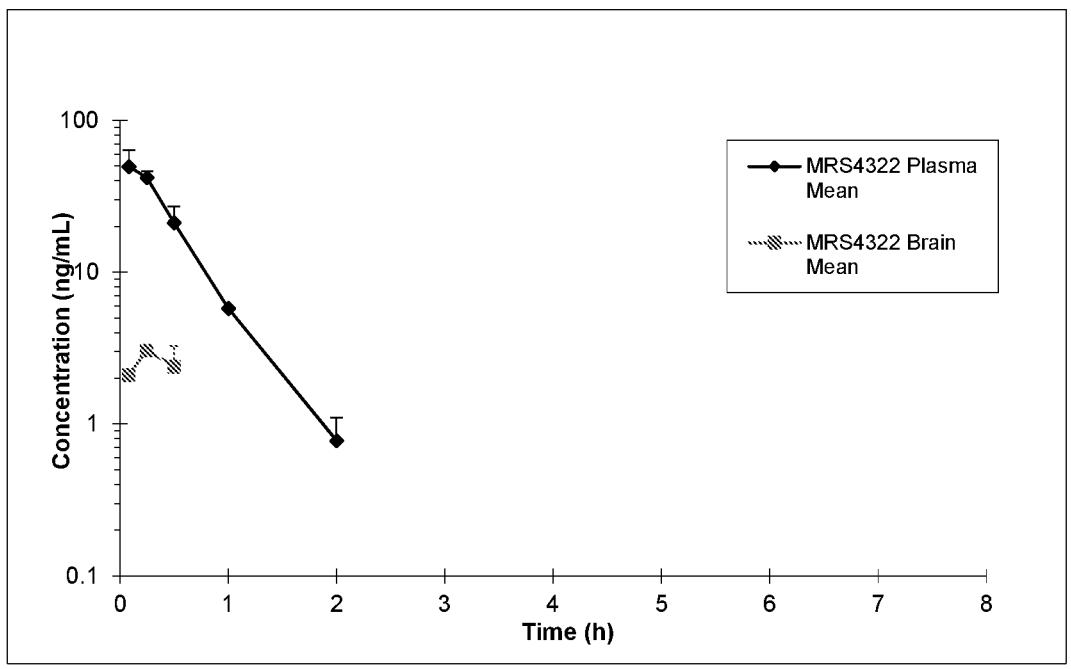
FIG. 1A shows plasma and brain concentration-time profiles of MRS4322 in mice following intraperitoneal administration.

1. Brain, CNS, Cardiovascular, and Other Injuries and Conditions

In some embodiments, the present invention provides a new approach to preventing and/or treating brain damage associated with acute brain trauma as well as longer term diseases of the brain and CNS and heart and cardiovascular diseases and conditions. In one aspect, the present invention provides methods of treating such injuries, diseases, and conditions by utilizing neuroprotective and neurorestorative effects mediated by astrocytes, which are now understood as the key natural caretaker cell of neurons, as well as the astrocyte mitochondria, which supply a significant portion of the brain's energy. In another aspect, the present invention provides methods of treating such injuries, diseases, and conditions by cardioprotective and regenerative effects mediated by $A_3R$ receptors. Regarding neuroprotective and neurorestorative effects, without wishing to be bound by theory, it is believed that selective enhancement of astrocyte energy metabolism mediated by $A_3R$ and/or $P2Y_1$ receptors promotes astrocyte caretaker functions, such as their neuroprotective and neurorestorative functions, in turn enhancing the resistance of neurons and other cells to both acute injury and long term stress. In some cases, it may be advantageous to achieve biased, i.e. selective or preferential, of one or more pathways mediated by $A_3R$ and/or $P2Y_1$ receptors wherein one or more undesired pathways are not activated, or activated to a lesser degree. In addition to or as an alternative to astrocytes, neuroprotective or neurorestorative function of glia, microglia, neurons, endothelium cells and other brain and/or CNS cell types may be activated. Accordingly, in one aspect, the present invention provides compounds and methods of use thereof for treating, ameliorating, or promoting recovery from certain conditions of the brain or central nervous system (CNS) such as brain injuries, for example by increasing neuroprotection and/or neurorestorative effects mediated by astrocytes, glia, microglia, neurons, endothelium cells or other cells of the brain and/or CNS, comprising administering to a patient in need thereof an effective amount of a disclosed compound.

Astrocytes play key roles in supporting and protecting neurons and they critically affect the outcome of brain injuries that cause brain damage, such as ischemic injuries. The central role astrocyte mitochondria themselves play in these brain functions is less well appreciated. For example, inhibition of astrocyte mitochondria increases swelling and leads to necrotic cell death. Neurons are permanently injured by recurrent spreading depolarizations only if astrocyte mitochondrial function fails, and astrocyte mitochondria are required for reduction of pathophysiological elevations of extracellular $K^+$, which initiate spreading depolarizations. Activation of purinergic receptors on astrocytes results in increased mitochondrial $Ca^{2+}$ that enhances mitochondrial citric acid cycle function and increases respiration and ATP production. Accordingly, in one aspect, the present invention relates to the discovery that activation of astrocyte purinergic receptors enhances brain cell survival signaling pathways, enabling both astrocyte and neuronal viability during oxidative stress. Furthermore, activated astrocytes generate and supply reduced glutathione, a key antioxidant that aids in the resistance of both astrocytes and neurons to oxidative stress. Thus, in one aspect, the present invention provides a method of modulating astrocyte purinergic receptors to promote survival and viability of one or more cell types in the brain of a patient after oxidative stress, such as oxidative stress caused by a brain injury, ischemia-reperfusion or a neurodegenerative condition, comprising administering to a patient in need thereof a disclosed compound.

In some embodiments, activation of astrocytes is achieved through contacting with a disclosed compound one or more purinergic receptors such as adenosine receptors (ARs), for example those associated with or expressed by astrocytes, thus modulating the activity of the one or more receptors. In some embodiments, through effects on adenosine receptors such as $A_1$, $A_{2A}$, $A_{2B}$ and $A_3$ on astrocytes, the compound activates astrocytes to treat one or more disclosed diseases or conditions. In some embodiments, after administration to a patient in need thereof, a disclosed compound influences one or more functions such as glutamate uptake, reactive gliosis, swelling, and release of neurotrophic and neurotoxic factors having an impact on metabolic stress and its consequences, thus treating one or more diseases or conditions. In some embodiments, the compound is an AR agonist. In some embodiments, the purinergic receptor is an $A_3$ adenosine receptor ($A_3R$). In some embodiments, the compound is an $A_3R$ agonist. In some embodiments, the compound is a partial agonist or biased agonist or biased partial agonist, at an $A_3$ receptor ($A_3R$), such as a human $A_3$ receptor ($hA_3R$). In some embodiments, the compound is a biased antagonist at an $A_3$ receptor. In some embodiments, the compound is MRS4322 or MRS1873 or a pharmaceutically acceptable salt thereof.

P2Y receptors are G-protein-coupled receptors and different subtypes of these receptors have important roles in processes such as synaptic communication, cellular differentiation, ion flux, vasodilation, blood brain barrier permeability, platelet aggregation and neuromodulation. Characterized members of the purinergic P2Y receptor family include the mammalian $P2Y_1$, $P2Y_{11}$, $P2Y_{12}$ and $P2Y_{13}$ receptors, which bind to adenine nucleotides; the $P2Y_4$, $P2Y_6$, and $P2Y_{14}$ receptors, that bind to uracil nucleotides; and the $P2Y_2$ and rodent $P2Y_4$ receptors, which have mixed selectivity. In some embodiments, activation of astrocytes is achieved through contacting with a disclosed compound one or more purinergic receptors such as P2Y receptors, for example those associated with or expressed by astrocytes, thus modulating the activity of the one or more receptors. In some embodiments, through effects on P2Y receptors such as $P2Y_1$, $P2Y_{11}$, $P2Y_{12}$ and $P2Y_{13}$ receptors associated with or expressed by astrocytes, the compound activates astrocytes to treat one or more disclosed diseases or conditions. In some embodiments, the P2Y receptor is a $P2Y_1$ receptor. In some embodiments, the $P2Y_1$ receptor is located on intracellular mitochondrial membranes. In some embodiments, the compound is a P2Y agonist. In some embodiments, the compound is a $P2Y_1$ agonist, e.g. at a human $P2Y_1$ receptor. In some embodiments, the compound is a biased agonist, partial agonist, or biased partial agonist at a $P2Y_1$ receptor, such as a human $P2Y_1$ receptor. In some embodiments, the compound is a biased antagonist at a $P2Y_1$ receptor. In some embodiments, the compound is MRS4322 or a pharmaceutically acceptable salt thereof.

In another aspect, the present invention provides a method of treating or ameliorating a brain injury, such as a brain injury resulting from a TBI or progressive neurodegenerative disorder, in a patient in need thereof, comprising administering to the patient an effective amount of a disclosed compound. In some embodiments, the subject has suffered a TBI, concussion, stroke, partial or total spinal cord transection, or malnutrition. In other embodiments, the subject has suffered toxic neuropathies, meningoencephalopathies, neurodegeneration caused by a genetic disorder, age-related neurodegeneration, or a vascular disease; or another disease disclosed in U.S. Pat. No. 8,691,775, which is hereby incorporated by reference. In some embodiments, the present invention provides a method of treating or ameliorating a brain injury, such as a brain injury resulting from a TBI or progressive neurodegenerative disorder, in a patient in need thereof, comprising administering to the patient an effective amount of an $A_3R$ agonist. In other embodiments, the present invention provides a method of treating or ameliorating a brain injury, such as a brain injury resulting from a TBI or progressive neurodegenerative disorder, in a patient in need thereof, comprising administering to the patient an effective amount of a $P2Y_1$ agonist. In some embodiments, the compound is a biased agonist, partial agonist, or biased partial agonist at an $A_3$ receptor. In some embodiments, the compound is a biased agonist, partial agonist, or biased partial agonist or antagonist at a $P2Y_1$ receptor. In some embodiments, the compound is MRS4322 or MRS1873, or a pharmaceutically acceptable salt thereof.

In another aspect, the present invention provides a method of promoting astrocyte-mediated neuroprotection or neurorestoration in a patient in need thereof, comprising administering to the patient an effective amount of a disclosed compound. In some embodiments, the present invention provides a method of promoting astrocyte-mediated neuroprotection or neurorestoration in a patient in need thereof, comprising administering to the patient an effective amount of an $A_3R$ agonist. In other embodiments, the present invention provides a method of promoting astrocyte-mediated neuroprotection or neurorestoration in a patient in need thereof, comprising administering to the patient an effective amount of a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or MRS1873, or a pharmaceutically acceptable salt thereof.

In another aspect, the present invention provides a method of promoting survival of neurons, glial cells, endothelial cells or other brain cells, such as those in an ischemic penumbra in a patient in need thereof, comprising administering to the patient an effective amount of a compound disclosed herein. In some embodiments, the present invention provides a method of promoting survival of neurons, glial cells, or other brain cells, such as those in an ischemic penumbra in a patient in need thereof, comprising administering to the patient an effective amount of an $A_3R$ agonist. In some embodiments, the present invention provides a method of promoting survival of neurons, glial cells, endothelial cells or other brain cells, such as those in an ischemic penumbra in a patient in need thereof, comprising administering to the patient an effective amount of a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or MRS1873, or a pharmaceutically acceptable salt thereof.

In further embodiments, the patient has or is at risk of acquiring a brain injury such as those below. Accordingly, methods of treating the conditions discussed below are also provided.

Traumatic Brain Injuries

Traumatic brain injuries (TBI) are a distressingly common medical condition and are predicted to become the third major cause of global morbidity and mortality by 2020. There are no approved treatments for TBI, and most TBI patients are discharged from the hospital with no pharmacological treatment (Witt 2006). Repetitive TBI such as concussions can trigger age-associated neurodegeneration that results in a range of symptoms and disabilities over decades (McKee 2013). TBIs can happen through sports-related injuries, motor vehicle accidents, falls, explosive impacts, physical assaults, etc. Injuries range widely in their complexity and severity, from "mild" concussions with brief alterations in mental status, cognitive difficulties, or loss of consciousness to "severe" with prolonged periods of unconsciousness and/or amnesia after the injury. In the U.S., approximately 1.7 million people have an injury resulting in a TBI annually and seek medical intervention (USCSF and CDC), and the CDC estimates that 1.6 to 3.8 million additional concussion incidents occur in sports and other recreational pursuits annually that do not present to hospital or emergency departments. (CDC; Langlois 2006) Approximately 5-10% of athletes will receive a concussion each sport season. (Sports Concussion Institute 2012) Football is the sport with the highest concussion risk for males (75% chance for concussion), while soccer has the highest concussion risk for females (50% chance for concussion). TBI is the leading cause of death and disability in children and young adults (CDC) and the most commonly received military-related injury; approximately 20% of U.S. Service Members deployed since 2003 have sustained at least one TBI. (Chronic Effects of Neurotrauma Consortium (CENC); Warden 2006; Scholten 2012; Taylor 2012; Gavett 2011; Guskiewicz 2005; Omalu 2005) Total TBI-related indirect and direct medical costs are estimated at $77 billion annually (UCSF and CDC). At least 5 million Americans require ongoing daily support in performing activities as a result of TBI (CDC and Thurman 1999).

Activation of astrocytes according to the present invention represents a new treatment option for such conditions. Accordingly, provided herein in one aspect is a method of treating TBI or promoting recovery from TBI, comprising administering to a patient in need thereof an effective amount of a disclosed compound. In some embodiments, the TBI is selected from traumatic injuries to the brain (such as concussion, blast injury, combat-related injury) or spinal cord (such as partial or total spinal cord transection). In some embodiments, the TBI results from a mild, moderate, or severe blow to the head, comprises an open or closed head wound, or results from a penetrating or non-penetrating blow to the head. In some embodiments, the present invention provides a method of treating TBI or promoting recovery from TBI, comprising administering to a patient in need thereof an effective amount of an $A_3R$ agonist. In some embodiments, the present invention provides a method of treating TBI or promoting recovery from TBI, comprising administering to a patient in need thereof an effective amount of a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or MRS1873, or a pharmaceutically acceptable salt thereof.

Stroke

A stroke occurs when a blood vessel that transports oxygen and nutrients to the brain is disrupted due to an ischemic blockage or from the hemorrhagic rupture of a blood vessel in the brain, causing neurons, glia and endothelial cells in the disrupted region of the brain to die. The outcome of the stroke depends upon the location and breadth of damage, and the impacts of that damage are observed in the body functions regulated by the damaged brain region. Strokes can cause unilateral or bilateral paralysis, speech and language disabilities, memory loss, behavioral changes, and even death. Stroke is the fourth leading cause of death in the United States and is a major cause of adult disability. Each year, ~800,000 people experience a new or recurrent stroke. Each day, over 2000 Americans will have a stroke, resulting in death in over 400 of these incidents. Stroke accounted for ~1 of every 19 deaths in the United States in 2010. An estimated 6.8 million Americans ≥20 years of age has had a stroke. (AHA and Go 2014) As of 2010, the annual direct and indirect cost of stroke was estimated at $36.5 billion. Within minutes of a stroke, the lack of blood flow will permanently damage a core of brain tissue. Between this damaged core and normal brain tissue is a region of tissue known as the penumbra—tissue that is under gradated stress from lessened blood flow and some disruption of energy metabolism. Over the first 24-48 hours following a stroke incident, the stress on neuronal and glia cells in the penumbra resolves either with some recovery or further cell death.

In one aspect, the present invention provides a method of neuroprotective therapy in a stroke patient, comprising administering to a patient in need thereof an effective amount of a disclosed compound. In some embodiments, such therapy salvages as much of the penumbra as possible, and/or limits further acute tissue damage, and/or promotes neuron recovery. In another aspect is provided a method of treating stroke or promoting recovery from stroke, comprising administering to a patient in need thereof an effective amount of a disclosed compound. In another aspect is provided a method of treating stroke or promoting recovery from stroke, comprising administering to a patient in need thereof an effective amount of an $A_3R$ agonist. In some embodiments, the present invention provides a method of treating stroke or promoting recovery from stroke, comprising administering to a patient in need thereof an effective amount of a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or a pharmaceutically acceptable salt thereof.

In some embodiments, the stroke is selected from selected from ischemic stroke, hemorrhagic stroke, subarachnoid hemorrhage, cerebral vasospasm, or transient ischemic attacks (TIA). In some embodiments, the stroke is ischemic. In some embodiments, the stroke is hemorrhagic. In some embodiments, the compound is administered within 48 hours of the stroke. In some embodiments, the compound is administered within 24 hours of the stroke. In some embodiments, the compound is administered within 16 hours of the stroke. In some embodiments, the compound is administered within 8, 4, 2, or 1 hours of the stroke. In some embodiments, the compound is administered for at least the first 1-72 hours following the stroke. In some embodiments, the compound is administered for at least the first 8-52 hours following the stroke. In some embodiments, the compound is administered for at least the first 8-48 hours following the stroke. In some embodiments, the compound is administered for at least the first 24-48 hours following the stroke. In some embodiments, the compound is administered chronically to treat the stroke as it occurs. In some embodiments, the compound is administered chronically to treat Transient Ischemic Attacks (TIA).

In some embodiments, the compound is administered chronically to treat ischemic stroke, hemorrhagic stroke, a subarachnoid hemorrhage, cerebral vasospasm, transient ischemic attacks (TIA), or treat a patient who is at an increased risk for a stroke, such as a patient who has had a stroke in the past and is at risk for a further stroke, such as a patient over the age of 40, 45, 50, 55, 60, 65, 70, 75, or 80 years of age.

In some embodiments, the compound treats an ischemia-reperfusion injury caused by the stroke.

Neurodegenerative Diseases

Neurodegenerative diseases are incurable, progressive, and ultimately debilitating syndromes resulting from the progressive degeneration and/or death of neurons in the brain and spinal cord. Neurodegeneration results in movement (ataxias) and/or cognitive function (dementias) disorders, and includes a spectrum of diseases such as Alzheimer's Disease (AD), Parkinson's Disease (PD), Huntington's Disease (HD), Multiple Sclerosis (MS), amyotrophic lateral sclerosis (ALS), and chronic traumatic encephalopathy (CTE). While many neurodegenerative diseases are principally genetic in origin, other causes can include viruses, alcoholism, tumors or toxins, and as is now clear, repetitive brain injuries.

Neurons accumulate cellular damage over time due to the foregoing factors, which is generally considered the reason why many neurodegenerative diseases associated with prolonged cellular stress, such as Alzheimer's disease and Parkinson's disease, occur in aged individuals. Dementias represent the predominant outcome of neurodegenerative diseases with AD representing approximately 60-70% of cases. (Kandale 2013) As discussed above, activation of neuroprotective and neurorestorative mechanisms can ameliorate the progression of one or more neurodegenerative diseases. Accordingly, in one aspect the present invention provides a method of treating a neurodegenerative disease or promoting recovery from a neurodegenerative disease, comprising administering to a patient in need thereof an effective amount of a disclosed compound.

In one aspect, the present invention provides a method of promoting neuroprotection or neurorestoration in a patient suffering from a neurodegenerative disease, comprising administering to the patient an effective amount of a disclosed compound. In some embodiments is provided a method of promoting neuroprotection or neurorestoration in a patient suffering from a neurodegenerative disease, comprising administering to the patient an effective amount of an $A_3R$ agonist. In other embodiments is provided a method of promoting neuroprotection or neurorestoration in a patient suffering from a neurodegenerative disease, comprising administering to the patient an effective amount of a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or a pharmaceutically acceptable salt thereof.

Alzheimer's Disease (AD)

An estimated 5.2 million Americans of all ages had AD in 2014; 11% of the population age 65 and older have AD. (Alzheimer's Association) By 2050, the number of people age 65 and older with AD is projected to nearly triple to a projected 13.8 million. In the U.S., the cost of providing care for AD patients is about $214 billion per year; 70% of this cost is covered by Medicare and Medicaid. The current trends would project these costs to grow to $1.2 trillion per year by 2050.

Activation of astrocytes and promoting neuroprotection and neurorestoration according to the present invention represents a new treatment option for AD. Accordingly, provided herein in one aspect is a method of treating AD or promoting neuroprotection or neurorestoration in a patient suffering from AD, comprising administering to the patient an effective amount of a compound disclosed herein. In some embodiments, the present invention provides a method of treating AD or promoting neuroprotection or neurorecovery in a patient suffering from AD, comprising administering to the patient an effective amount of an $A_3R$ agonist. In some embodiments, the present invention provides a method of treating AD or promoting neuroprotection or neurorecovery in a patient suffering from AD, comprising administering to the patient an effective amount of a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or a pharmaceutically acceptable salt thereof.

Parkinson's Disease (PD)

As many as one million Americans live with PD, and each year approximately 60,000 Americans are newly diagnosed not including the thousands of cases that go undetected. (Parkinson's Disease Foundation) The total combined direct and indirect cost of PD, including medical treatment, social security payments and lost income, is estimated to be nearly $25 billion per year in the United States. (Parkinson's Disease Foundation and Huse 2005)

Activation of neuroprotection and neurorestoration according to the present invention represents a new treatment option for PD. Accordingly, provided herein in one aspect is a method of treating PD or promoting neuroprotection or neurorestoration in a patient suffering from PD, comprising administering to the patient an effective amount of a disclosed compound. In some embodiments, the present invention provides a method of treating PD or promoting neuroprotection or neurorecovery in a patient suffering from PD, comprising administering to the patient an effective amount of an $A_3R$ agonist. In some embodiments, the present invention provides a method of treating PD or promoting neuroprotection or neurorecovery in a patient suffering from PD, comprising administering to the patient an effective amount of a $P2Y_1$ agonist. In some embodiments, the compound is a biased agonist, partial agonist, or biased partial agonist or antagonist at an $A_3$ receptor. In some embodiments, the compound is a biased biased agonist, partial agonist, or biased partial agonist or antagonist at a $P2Y_1$ receptor. In some embodiments, the compound is MRS4322 or MRS1873, or a pharmaceutically acceptable salt thereof.

Multiple Sclerosis (MS)

More than 400,000 people in the United States have MS. In young adults, MS represents the most prevalent disease of the central nervous system. (Multiple Sclerosis Foundation) There is potential for astrocytes to reverse the destruction of nerve cell myelin coatings that is caused by MS by their neurorestorative effects and promotion of healing in the damaged CNS of MS patients.

Activation of neuroprotection and neurorestoration in the CNS according to the present invention thus represents a new treatment option for MS. Accordingly, provided herein in one aspect is a method of treating MS or promoting neuroprotection or neurorestoration in a patient suffering from MS, comprising administering to the patient an effective amount of a disclosed compound. In some embodiments, the present invention provides a method of treating MS or promoting neuroprotection or neurorecovery in a patient suffering from MS, comprising administering to the patient an effective amount of an $A_3R$ agonist. In some embodiments, the present invention provides a method of treating MS or promoting neuroprotection or neurorecovery in a patient suffering from MS, comprising administering to the patient an effective amount of a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or MRS1873, or a pharmaceutically acceptable salt thereof.

Amyotrophic Lateral Sclerosis (ALS)/Lou Gehrig's Disease

Approximately 5,600 people in the U.S. are diagnosed with ALS each year; as many as 30,000 Americans may have the disease concurrently. (ALS Association) Activation of astrocytes can provide stimulation of recovery and repair of the neurons and their connections in an ALS patient.

Accordingly, provided herein in one aspect is a method of treating ALS or promoting neuroprotection or neurorestoration in a patient suffering from ALS, comprising administering to the patient an effective amount of a disclosed compound. Also provided in other embodiments is a method of stimulating recovery and repair of the neurons and their connections in an ALS patient, comprising administering to the patient an effective amount of a compound disclosed herein. In some embodiments, the present invention provides a method of treating ALS or promoting neuroprotection or neurorecovery in a patient suffering from ALS, comprising administering to the patient an effective amount of an $A_3R$ agonist. In some embodiments, the present invention provides a method of treating ALS or promoting neuroprotection or neurorecovery in a patient suffering from ALS, comprising administering to the patient an effective amount of a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or a pharmaceutically acceptable salt thereof.

Chronic Traumatic Encephalopathy (CTE)

CTE (a form of tauopathy) is a progressive neurodegenerative disease found in individuals who have suffered one or more (often multiple, or repeated over the course of time) severe blows to the head. CTE is most often diagnosed in professional athletes in American football, soccer, hockey, professional wrestling, stunt performing, bull riding and rodeo performing, motocross, and other contact sports who have experienced brain trauma and/or repeated concussions. A subset of CTE sufferers have chronic traumatic encephalomyopathy (CTEM), which is characterized by motor neuron disease symptoms that mimic ALS. Progressive muscle weakness and motor and gait abnormalities are believed to be early signs of CTEM. First stage symptoms of CTE include progressive attention deficit, disorientation, dizziness, and headaches. Second stage symptoms comprise memory loss, social instability, erratic behavior, and poor judgment. In third and fourth stages, patients suffer progressive dementia, slowed movements, tremors, hypomimia, vertigo, speech impediments, hearing loss, and suicidality, and may further include dysarthria, dysphagia, and ocular abnormalities, e.g. ptosis.

Accordingly, provided herein in one aspect is a method of treating or preventing CTE or promoting neuroprotection or neurorestoration in a patient suffering from CTE, comprising administering to the patient an effective amount of a disclosed compound. Also provided in other embodiments is a method of stimulating recovery and repair of the neurons and their connections in a CTE patient, comprising administering to the patient an effective amount of a disclosed compound. In some embodiments, the compound treats one or more symptoms of first stage, second stage, third stage, or fourth stage CTE. In some embodiments, the present invention provides a method of treating CTE or promoting neuroprotection or neurorecovery in a patient suffering from CTE, comprising administering to the patient an effective amount of an $A_3R$ agonist. In some embodiments, the present invention provides a method of treating CTE or promoting neuroprotection or neurorecovery in a patient suffering from CTE, comprising administering to the patient an effective amount of a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or MRS1873 or a pharmaceutically acceptable salt thereof.

On a microscopic scale the pathology includes neuronal death, tau deposition, TAR DNA-binding Protein 43 (TDP 43) beta-amyloid deposition, white matter changes, and other abnormalities. Tau deposition includes the increasing presence of dense neurofibrillary tangles (NFT), neurites, and glial tangles, which are made up of astrocytes and other glial cells. Thus, in some embodiments, the method treats, enhances clearance or prevents neuronal death, tau deposition, TAR DNA-binding Protein 43 (TDP 43) beta-amyloid deposition, white matter changes, and other abnormalities associated with CTE.

In some embodiments, the present invention provides long-term administration of a compound disclosed herein, such as a biased agonist, partial agonist, or biased partial agonist of $A_3R$, or a biased agonist, partial agonist, or biased partial agonist of $P2Y_1$, to treat a neurodegenerative disease, such as those discussed above and below.

Cardiovascular Diseases

Disclosed compounds are also useful in treating a variety of cardiovascular diseases and conditions. In some embodiments, the present invention provides a method of treating a heart or cardiovascular disease, such as cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis, comprising administering an effective amount of a disclosed compound to a patient in need thereof, such as MRS4322 or MRS1873, or a pharmaceutically acceptable salt thereof. In some embodiments, a disclosed compound provides for modulation of ATP-sensitive potassium channels, for example via biased agonism, partial agonism, or biased partial agonism at an $A_3R$ receptor.

In some embodiments, the heart or cardiovascular disease is cardiac ischemia or myocardial infarction.

Other Diseases

Compounds that modulate beneficial effects such as neuroprotection, for example by increasing astrocyte mitochondrial activity, also have the potential to treat a variety of other diseases. For example, due to the role of astrocytes in neuroprotection disclosed in the present invention, activation of astrocytes, for example via modulation of $A_3R$ and/or a $P2Y_1$ receptor, may be useful in treating various diseases and conditions discussed below. Accordingly, in some embodiments, the present invention provides a method of treating or promoting neuroprotection or neuroregeneration in a patient suffering from a disease or condition, comprising administering to the patient an effective amount of a disclosed compound, for example MRS4322 or a pharmaceutically acceptable salt thereof. In some embodiments, the disease or condition is selected from autoimmune diseases, allergic diseases, and/or transplant rejection and graft-versus-host disease (for the use of certain nucleoside and nucleotide compounds in treating these conditions, see, for example, WO 2007/20018, hereby incorporated by reference). In other embodiments, the disease or condition is selected from intraocular hypertension and/or glaucoma (for the use of certain nucleoside and nucleotide compounds in treating these conditions, see, for example, WO 2011/77435, hereby incorporated by reference). In other embodiments, the disease or condition is selected from odor sensitivity and/or an olfactory disorder (for the use of certain nucleoside and nucleotide compounds in treating these conditions, see, for example, EP1624753, hereby incorporated by reference). In other embodiments, the disease or condition is selected from type 2 diabetes and/or pain control (for the use of certain nucleoside and nucleotide compounds in treating these conditions, see, for example, US 2010/0256086, hereby incorporated by reference).

In other embodiments, the disease or condition is selected from respiratory diseases and/or cardiovascular (CV) diseases (for the use of certain nucleoside and nucleotide compounds in treating these conditions, see, for example, FASEB J. (2013) 27:1118.4 (abstract of meeting), hereby incorporated by reference). In other embodiments, the disease or condition is selected from deficits in CNS function, deficits in learning and/or deficits in cognition (for the use of certain nucleoside and nucleotide compounds in treating these conditions, see, for example, Neuropsychopharmacology. 2015 January; 40(2):305-14. doi: 10.1038/npp.2014.173. Epub 2014 Jul. 15. "Impaired cognition after stimulation of a $P2Y_1$ receptor in the rat medial prefrontal cortex," Koch, H. et al. PMID: 25027332, hereby incorporated by reference). In other embodiments, the disease or condition is selected from a neurodegenerative disease such as Alzheimer's disease, Parkinson's disease, Huntington's disease, prion disease, and/or amyotrophic lateral sclerosis (for the use of certain nucleoside and nucleotide compounds in treating these conditions, see, for example, U.S. Pat. No. 8,691,775, hereby incorporated by reference). In other embodiments, the disease or condition is selected from otic disorders, Meniere's disease, endolymphatic hydrops, progressive hearing loss, dizziness, vertigo, tinnitus, collateral brain damage associated with radiation cancer therapy, and/or migraine treatment (for the use of certain nucleoside and nucleotide compounds in treating these conditions, see, for example, US 2009/0306225; UY31779; and U.S. Pat. No. 8,399,018, each of which is hereby incorporated by reference). In other embodiments, the disease or condition is selected from pathological sleep perturbations, depression, sleep disorders in the elderly, Parkinson's disease, Alzheimer's disease, epilepsy, schizophrenia, and/or symptoms experienced by recovering alcoholics (for the use of certain nucleoside and nucleotide compounds in treating these conditions, see, for example, US 2014/0241990, hereby incorporated by reference). In other embodiments, the disease or condition is selected from damage to neurons or nerves of the peripheral nervous system during surgery (for the use of certain nucleoside and nucleotide compounds in treating these conditions, see, for example, U.S. Pat. No. 8,685,372, hereby incorporated by reference). In other embodiments, the disease or condition is a cancer such as prostate cancer (for the use of certain nucleoside and nucleotide compounds in treating these conditions, see, for example, Biochem Pharmacol. 2011 Aug. 15; 82(4): 418-425. doi:10.1016/j.bcp.2011.05.013. "Activation of the P2Y1 Receptor Induces Apoptosis and Inhibits Proliferation of Prostate Cancer Cells," Qiang Wei et al., hereby incorporated by reference). In other embodiments, the disease or condition is selected from one or more gastrointestinal conditions such as constipation and/or diarrhea (for the use of certain nucleoside and nucleotide compounds in treating these conditions, see, for example, Acta Physiol (Oxf). 2014 December; 212(4):293-305. doi: 10.1111/apha.12408. "Differential functional role of purinergic and nitrergic inhibitory cotransmitters in human colonic relaxation," Mañé N1, Gil V, Martinez-Cutillas M, Clavé P, Gallego D, Jimenez M.; and Neurogastroenterol. Motil. 2014 January; 26(1):115-23. doi: 10.1111/nmo.12240. Epub 2013 Oct. 8. "Calcium responses in subserosal interstitial cells of the guinea-pig proximal colon," Tamada H., Hashitani H. PMID: 24329947, hereby incorporated by reference). In other embodiments, the disease or condition is selected from pain mediated by the CNS, such as neuropathic pain, inflammatory pain, and/or acute pain (for the use of certain nucleoside and nucleotide compounds in treating these conditions, see, for example, Br J Pharmacol. 2010 March; 159(5):1106-17. doi: 10.1111/j.1476-5381.2009.00596.x. Epub 2010 Feb. 5. "A comparative analysis of the activity of ligands acting at P2X and P2Y receptor subtypes in models of neuropathic, acute and inflammatory pain." Andó RD1, Méhész B, Gyires K, Illes P, Sperlágh B. PMID: 20136836), hereby incorporated by reference).

In other embodiments, the disease or condition is selected from cancer of the brain, such as glioblastoma (for the use of certain nucleoside and nucleotide compounds in treating these conditions, see, for example, Purinergic Signal. 2015 September; 11(3):331-46. doi: 10.1007/s11302-015-9454-7. Epub 2015 May 15. "Potentiation of temozolomide antitumor effect by purine receptor ligands able to restrain the in vitro growth of human glioblastoma stem cells." D'Alimonte, I. et al. PMID: 25976165, hereby incorporated by reference). In other embodiments, the disease or condition is pain (for the use of certain nucleoside and nucleotide compounds in treating pain, see, for example, Pharmacol Biochem Behav. 2015 January; 128:23-32. doi: 10.1016/j.pbb.2014.11.001. Epub 2014 Nov. 6. "Participation of peripheral $P2Y_1$, $P2Y_6$ and $P2Y_{11}$ receptors in formalin-induced inflammatory pain in rats." Barragán-Iglesias P. et al. PMID: 25449358; and Neuropharmacology. 2014 April; 79:368-79. doi: 10.1016/j.neuropharm.2013.12.005. Epub 2013 Dec. 12. "Blockade of peripheral $P2Y_1$ receptors prevents the induction of thermal hyperalgesia via modulation of TRPV1 expression in carrageenan-induced inflammatory pain rats: involvement of p38 MAPK phosphorylation in DRGs." Kwon S G, Roh D H, Yoon S Y, Moon J Y, Choi S R, Choi H S, Kang S Y, Han H J, Beitz A J, Lee J H. PMID: 24333674, each of which is hereby incorporated by reference). In other embodiments, the disease or condition is selected from a gastrointestinal disorder such as diarrhea (for the use of certain nucleoside and nucleotide compounds in treating these conditions, see, for example, Acta Physiol (Oxf). 2014 December; 212(4):293-305. doi: 10.1111/apha.12408. "Differential functional role of purinergic and nitrergic inhibitory cotransmitters in human colonic relaxation," Mañé N., Gil V, Martinez-Cutillas M, Clavé P, Gallego D, Jimenez M., hereby incorporated by reference). In other embodiments, the disease or condition is impaired cognition (for the use of certain nucleoside and nucleotide compounds in treating this condition, see, for example, Neuropsychopharmacology. 2015 January; 40(2): 305-14. doi: 10.1038/npp.2014.173. Epub 2014 Jul. 15. "Impaired cognition after stimulation of $P2Y_1$ receptors in the rat medial prefrontal cortex," Koch H, Bespalov A, Drescher K, Franke H, Krugel U. PMID: 25027332, hereby incorporated by reference).

In some embodiments, the present invention provides a method of treating a disease or condition associated with brain injury or a neurodegenerative condition, such as epilepsy, migraine, collateral brain damage associated with radiation cancer therapy, depression, mood or behavioral changes, dementia, erratic behavior, suicidality, tremors, Huntington's chorea, loss of coordination of movement, deafness, impaired speech, dry eyes, hypomimia, attention deficit, memory loss, cognitive difficulties, vertigo, dysarthria, dysphagia, ocular abnormalities, or disorientation, comprising administering to a patient in need thereof an effective amount of a disclosed compound. In some embodiments, the compound is an $A_3R$ agonist. In some embodiments, the compound is a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or MRS1873, or a pharmaceutically acceptable salt thereof.

In further embodiments, the present invention provides a method of treating a neurodegenerative disease selected from the group consisting of Alzheimer's disease, Parkinson's disease, Huntington's disease, multiple sclerosis, amyotrophic lateral sclerosis, and prion disease in a patient in need thereof, comprising administering an effective amount of a disclosed compound. In some embodiments, the compound is an $A_3R$ agonist. In some embodiments, the compound is a $P2Y_1$ agonist. In some embodiments, the compound is a biased agonist, partial agonist, or biased partial agonist or antagonist at an $A_3$ receptor. In some embodiments, the compound is a biased agonist, partial agonist, or biased partial agonist or antagonist at a $P2Y_1$ receptor. In some embodiments, the compound is MRS4322 or MRS1873, or a pharmaceutically acceptable salt thereof.

In some embodiments, the improvement in cognitive or neurological function is measured as a score increase between about 1% and 20% in the delayed verbal recall task of the revised Wechsler Memory Scale. For example, the improvement in cognitive function may be measured as a score increase between about 1% and 10%, or between about 1% and 5%.

2. Description of Certain Compounds of the Present Invention

In one aspect, the present invention provides compounds useful for treating, ameliorating, or promoting recovery from certain conditions of the brain or central nervous system (CNS) such as a brain injury or a neurodegenerative condition. In some embodiments, a disclosed compound increases neuroprotection and neuroregeneration mediated by astrocytes, thereby treating, ameliorating, or promoting recovery from the condition. In some embodiments, the compound is selective for an $A_3$ receptor, for example selective for an $A_3$ receptor by at least 10-fold relative to other adenosine receptors; or for example more than 25-fold, 50-fold, 100-fold, 500-fold, or 1000-fold relative to other adenosine receptors. In some embodiments, the compound selectively modulates an $A_3$ receptor. In some embodiments, the compound is a selective agonist at an $A_3$ receptor. In some embodiments, the compound is a selective partial agonist at an $A_3$ receptor. In some embodiments, the compound is a biased full or partial agonist. In some embodiments, the compound is a biased full or partial antagonist.

In further embodiments, the compound is selective for a $P2Y_1$ receptor, for example selective for $P2Y_1$ receptors by at least 10-fold relative to other P2Y receptors; or for example more than 25-fold, 50-fold, 100-fold, 500-fold, or 1000-fold relative to other P2Y receptors. In some embodiments, the compound selectively modulates a $P2Y_1$ receptor. In some embodiments, the compound is a selective agonist at a $P2Y_1$ receptor. In some embodiments, the compound is a selective partial agonist at a $P2Y_1$ receptor. In some embodiments, the compound is a biased full or partial agonist. In some embodiments, the compound is a biased full or partial antagonist.

The term "biased" refers to compounds that preferentially modulate, activate, agonize, or antagonize one or more, but not all, of the pathways associated with a receptor.

Without wishing to be bound by theory, it is believed that biased full or partial agonism or antagonism allows for selective modulation of one or more pathways linked to an $A_3$ or $P2Y_1$ receptor, which may lead to improved treatment of a disease or condition and avoidance of undesired pathway modulation (which would lead to side effects). Selective modulation may preferentially activate astrocytes as disclosed herein, for example to treat a brain injury or neurodegenerative disease or condition. Accordingly, in some embodiments, a disclosed compound is a biased full or partial agonist or antagonist of one or more G-coupled or G-independent pathways linked to the adenosine $A_3$ receptor or $P2Y_1$ receptor. In some embodiments, the compound selectively modulates a pathway mediated by $A_3$ or a $P2Y_1$ receptor, such as beta-arrestin activation, intracellular calcium mobilization, cAMP modulation, ATP-dependent potassium channel activation, or ERK1/2 phosphorylation, or other downstream cellular activities associated with such pathways. In some embodiments, the pathway increases or is related to neuroprotection or neurorestoration, or cardioprotection or cardioregeneration. In some embodiments, the compound is selected from a (N)-methanocarba nucleoside such as MRS4322; or a pharmaceutically acceptable salt thereof.

The term "methanocarba nucleoside" as used herein refers to a nucleoside analog in which the oxygen present in the tetrahydrofuran ring of the ribose sugar is replaced with a methylene unit and the resulting carbocyclic ring is fused to a cyclopropyl ring to form a bicyclo[3.1.0]hexane, such as the structures

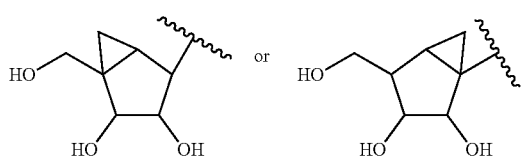

Without being bound by theory, it is believed that methanocarba nucleosides mimic a sugar conformation or pseudoconformation believed to be favored by certain receptor subtypes. In some embodiments, North methanocarba nucleosides are those that mimic or prefer a C3'-endo/C2'-exo sugar conformation and South methanocarba nucleosides are those that mimic or prefer a C3'-exo/C2'-endo conformation. In some embodiments, a (N)-methanocarba ("North" methanocarba) sugar has the following structure:

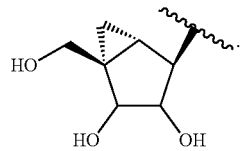

In some embodiments, a (N)-methanocarba sugar has the following structure:

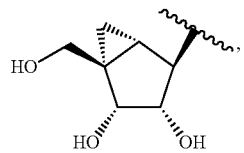 [SMILES: *[C@H]1[C@H](O)[C@H](O)[C@]2(CO)C[C@H]12]

referred to herein as a "D-(N)-methanocarba sugar." In other embodiments, a methanocarba sugar is in the South, or (5)-methanocarba, configuration. In some embodiments, such methanocarba sugars are represented by the structure:

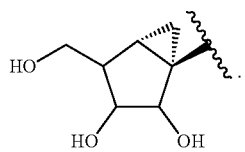

In some embodiments, a (S)-methanocarba sugar has the following structure:

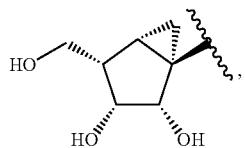 [SMILES: *[C@]12C[C@H]1[C@@H](CO)[C@@H](O)[C@H]2O]

referred to herein as a "D-(S)-methanocarba sugar."

In some embodiments, the compound is functionally selective at the $A_3$ or $P2Y_1$ receptor, i.e., selectively discriminates among pathways mediated by $A_3$ or a $P2Y_1$ receptor, for example by modulating one or more pathways but not others, or by activating one or more pathways and deactivating one or more other pathways. In some embodiments, the compound is an antagonist as measured by cAMP signaling, but a partial agonist for β-arrestin recruitment. In other embodiments, the compound is an agonist of Gq/11-mediated $Ca^{2+}$ mobilization and a partial agonist or antagonist of arrestin recruitment. In some embodiments, the present invention provides a method of treating a brain injury or neurodegenerative disease or condition via biased or functionally selective $A_3$ receptor modulation (e.g., by selective agonism or antagonism among pathways such as those mentioned above), comprising administering an effective amount of a disclosed compound to a patient in need thereof. In some embodiments, the compound is selected from DMPA, CCPA, MRS1760, or MRS542 (see Verzijl D, et al., "Functional selectivity of adenosine receptor ligands," Purinergic Signaling 7: 171-192 (2011)). In some embodiments, the compound is DBXRM. In some embodiments, the compound is selected from a (N)-methanocarba nucleoside such as MRS4322; or a pharmaceutically acceptable salt thereof.

It has been surprisingly found that certain purine nucleoside mono-, di-, and tri-phosphates, such as those described in detail herein, are rapidly dephosphorylated in vivo, possibly by ectonucleotidases, enzymes responsible for the dephosphorylation of nucleotides that are present both on the surface of cell membranes and circulating in blood and plasma (See Ziganshin et al. Pflugers Arch. (1995) 429:412-418). It is often extremely difficult to predict which nucleotide analogs will be substrates for ectonucleotidases and will thus be expected to be dephosphorylated in vivo. In some embodiments, the dephosphorylated compound is responsible for the therapeutic efficacy. Thus, in some embodiments the corresponding, phosphorylated mono-, di-, or tri-phosphate, or a phosphate ester such as an alkyl or phenyl ester thereof, is a prodrug or precursor to the agent responsible for the therapeutic effect.

In some embodiments, compounds of the present invention are able to cross the blood-brain barrier (BBB). The term "blood-brain barrier" or "BBB", as used herein, refers to the BBB proper as well as to the blood-spinal barrier. The blood-brain barrier, which consists of the endothelium of the brain vessels, the basal membrane and neuroglial cells, acts to limit penetration of substances into the brain. In some embodiments, the brain/plasma ratio of total drug is at least approximately 0.01 after administration (e.g. oral or intravenous administration) to a patient. In some embodiments, the brain/plasma ratio of total drug is at least approximately 0.03. In some embodiments, the brain/plasma ratio of total drug is at least approximately 0.06. In some embodiments, the brain/plasma ratio of total drug is at least approximately 0.1. In some embodiments, the brain/plasma ratio of total drug is at least approximately 0.2.

Prototypical adenosine $A_3$ agonists such as Cl-IB-MECA and MRS5698 are low-solubility, lipophilic compounds with c Log P values typically >2. This lipophilicity is a major factor contributing to these compounds' high plasma protein binding, high brain binding and resulting low free fraction of drug available to interact with the $A_3$ receptor in the brain. In some embodiments, for example neurological and neurodegenerative conditions, the physicochemical properties of compounds of the present invention such as MRS4322 and MRS1873 are substantially different; these and related compounds are hydrophilic compounds with c Log P<0, resulting in high solubility, low plasma and brain binding and high unbound drug concentrations available to interact with the $A_3$ receptor.

Accordingly, in some embodiments the compound has a c Log P less than about 0.8, about 0.7, about 0.6, about 0.5, about 0.4, about 0.3, about 0.2, about 0.1, about 0.05, about 0.01, or about 0.005. In some embodiments, the compound has a c Log P less than about 0, such as less than about −0.1, −0.2, −0.3, −0.4, −0.5, −0.6, −0.7, −0.8, or −0.9 or less. In some embodiments, the compound has an unbound fraction in plasma of about 0.5 to 0.9. In some embodiments, the compound has an unbound fraction in plasma of about 0.6 to 0.85, 0.7 to 0.8, or about 0.75. In some embodiments, the compound has an unbound fraction in brain of at least about 0.02, or at least about 0.03, 0.04, 0.05, 0.06, 0.07, 0.08, 0.09, 0.1, 0.12, 0.15, or 0.17 or greater. In some embodiments, the compound has an unbound fraction in plasma of about 0.6 to 0.85, 0.7 to 0.8, or about 0.75 and/or at least 0.08 unbound fraction in brain.

Compounds of the invention may be prepared using methods known in the art, using no more than routine experimentation. For example, certain compounds of the invention may be prepared following the procedures provided in U.S. Pat. No. 7,087,589 (and references cited therein), which is hereby incorporated by reference.

In some embodiments, the compound is selected from adenosine, ADP, 2-methylthio-ADP trisodium salt, ATP, ATP disodium salt, α,β-methylene ATP, α,β-methyleneadenosine 5'-triphosphate trisodium salt, 2-methylthioadenosine triphosphate tetrasodium salt, 2-MeSATP, BzATP triethylammonium salt, inosine, cytidine, acylated cytidines, cytidine-monophosphate (CMP), cytidine diphosphate (CDP), cytidine triphosphate (CTP), CDP-choline, CMP-choline, denufosol, denufosol tetrasodium, GTP, ITP, MRS 541, MRS 542, MRS 1760, MRS 2179, MRS 2279, MRS 2341, MRS 2365, MRS 2500, MRS 2690, MRS 2698, MRS 3558, MRS 4322, MRS 5151, MRS 5676, MRS 5678, MRS 5697, MRS 5698, MRS 5923, MRS 5930, Benzyl-NECA, IB-MECA, Cl-IB-MECA, LJ529, DPMA, CCPA, DBXRM, HEMADO, PEMADO, HENECA, PENECA, CP608,039, CP532,903, CGS21680, AR132, VT72, VT158, VT160, VT163, PSB 0474, uridine 5'-diphosphate (UDP), UDP-glucose, uridine β-thiodiphosphate (UDPβS), uridine 5'-triphosphate (UTP), uridine γ-thiophosphate (UTPγS), 2-thio-UTP tetrasodium salt, UTPγS trisodium salt, uridine-5'-diphosphoglucose, diuridine triphosphate, 2-(hexylthio) (HT)-AMP, diadenosine pentaphosphate, 2'-deoxy-2'-amino-UTP, 2-thio-UTP, triacetyluridine, diacetyl/acyl uridine, uridine, suramin, dipyridamole analogs, diadenosine tetraphosphate $Ap_4U$, $Ap_4A$, INS365, INS37217, or INS48823; wherein each sugar may be replaced with a methanocarba sugar in the North or South conformation or each sugar may be replaced with a D-ribosugar; or a pharmaceutically acceptable salt thereof.

In some embodiments, 2-methylthio-ADP or a pharmaceutically acceptable salt thereof is useful in the methods of the present invention. Without wishing to be bound by theory, it is believed that 2-MeS ADP is rapidly hydrolyzed to 2-methylthioadenosine in vivo, where it is a biased agonist, partial agonist, or biased partial agonist of $A_3R$. 2-methylthioadenosine is believed to have receptor data very similar to that of MRS4322.

In some embodiments, the compound is an $A_3R$ agonist such as $N^6$-benzyladenosine-5'-N-methyluronamides such as $N^6$-(3-iodobenzyl)-adenosine-5'-N-methyluronamide, also known as IB-MECA or Can-Fite CF-101, or 2-Chloro-$N^6$-(3-iodobenzyl)-adenosine-5'-N-methyluronamide (also known as 2-Cl-IB-MECA or Can-Fite CF-102; (N)-methanocarba nucleosides such as (1R,2R,3S,4R)-4-(2-chloro-6-((3-chlorobenzyl)amino)-9H-purin-9-yl)-2,3-di-hydroxy-N-methylbicyclo[3.1.0]hexane-1-carboxamide (also known as CF502, Can-Fite Biopharma, MA); (2S,3S,4R,5R)-3-amino-5-[6-(2,5-dichlorobenzylamino)purin-9-yl]-4-hydroxy-tetrahydrofuran-2-carboxylic acid methylamide (also known as CP532,903); (1'S,2'R,3'S,4'R,5'S)-4-(2-chloro-6-(3-chlorobenzylamino)-9H-purin-9-yl)-2,3-dihydroxy-N-methylbicyclo[3.1.0]hexane-1-carboxamide (also known as MRS3558), 2-(1-hexynyl)-N-methyladenosine; (1S,2R,3S, 4R)-2,3-dihydroxy-4-(6-((3-iodobenzyl)amino)-4H-purin-9

(5H)-yl)-N-methylcyclopentanecarboxamide (also known as CF101, Can-Fite); (1S,2R,3S,4R)-4-(2-chloro-6-((3-iodobenzyl)amino)-4H-purin-9(5H)-yl)-2,3-dihydroxy-N-methylcyclopentanecarboxamide (also known as CF102, Can-Fite); (1'R,2'R,3'S,4'R,5'S)-4-{2-chloro-6-[(3-iodophenylmethyl)amino]purin-9-yl-}-1-(methylaminocarbonyl)-bicyclo[3.1.0]hexane-2,3-diol (also known as MRS1898); or 2-dialkynyl derivatives of (N)-methanocarba nucleosides; or a pharmaceutically acceptable salt thereof. In some embodiments, the compound is selected from IB-MECA (also known as CF101), or Cl-IB-MECA (also known as CF102); or a pharmaceutically acceptable salt thereof. In some embodiments, the compound is selected from a (N)-methanocarba nucleoside such as those disclosed above; or a pharmaceutically acceptable salt thereof.

Also included are $A_3R$ allosteric modulators which enhance the receptor activity in the presence of the native ligand, such as 2-cyclohexyl-N-(3,4-dichlorophenyl)-1H-imidazo[4,5-c]quinolin-4-amine (also known as CF602, Can-Fite). However, the above-listed $A_3R$ agonists are by no means exclusive and other such agonists may also be used. The administration of $A_3R$ agonists covalently bound to polymers is also contemplated. For example, $A_3R$ agonists may be administered in the form of conjugates where an agonist is bound to a polyamidoamine (PAMAM) dendrimer.

Without wishing to be bound by theory, it is believed that full or partial agonism, including biased agonism, by certain uridine analogs will allow for selective modulation of one or more pathways which may lead to improved treatment of a disclosed disease or condition and avoidance of undesired pathway modulation (which would lead to side effects). In some embodiments, selective modulation preferentially activates astrocytes or other glial cells such as microglia and oligodendrocytes to treat a disclosed brain injury or neurodegenerative disease or condition. Certain uridine analog compounds suitable for use in the present invention are disclosed in WO 2014/160502, which is hereby incorporated by reference in its entirety. In some embodiments, the compound is an $A_3R$ agonist. In some embodiments, the compound is a $P2Y_1$ agonist. In some embodiments, the compound is a biased agonist at an adenosine receptor, such as an $A_1$, $A_{2A}$, $A_{2B}$ or $A_3$ receptor. In some embodiments, the compound is a biased agonist, partial agonist, or biased partial agonist at an $A_3$ receptor. In some embodiments, the compound is a biased agonist, partial agonist, or biased partial agonist at a $P2Y_1$ receptor. In some embodiments, the compound is selected from the group consisting of:

1

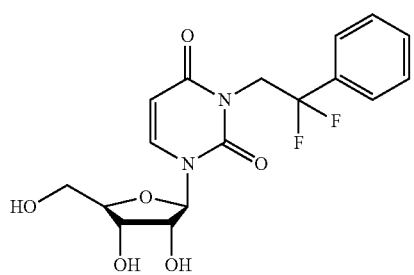

2

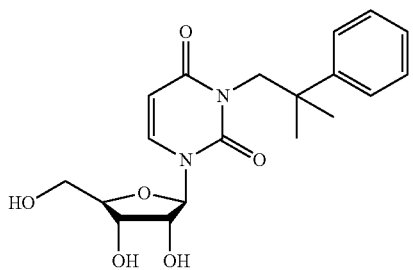

3

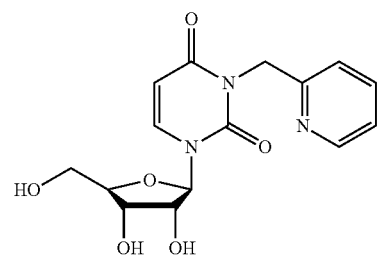

4

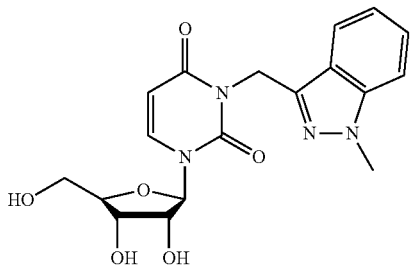

5

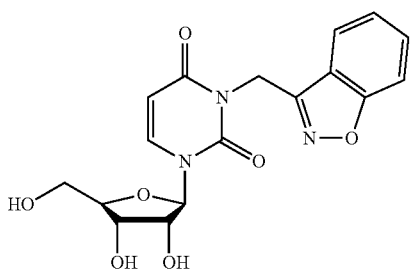

6

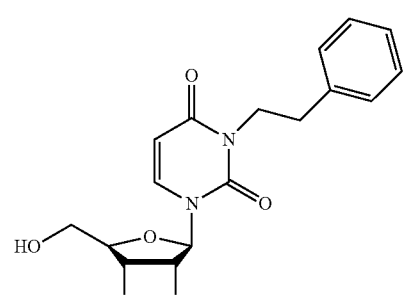

7

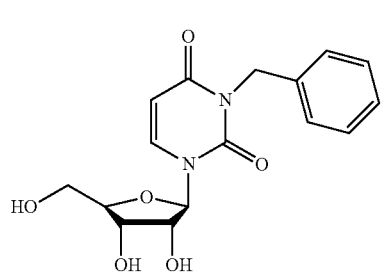

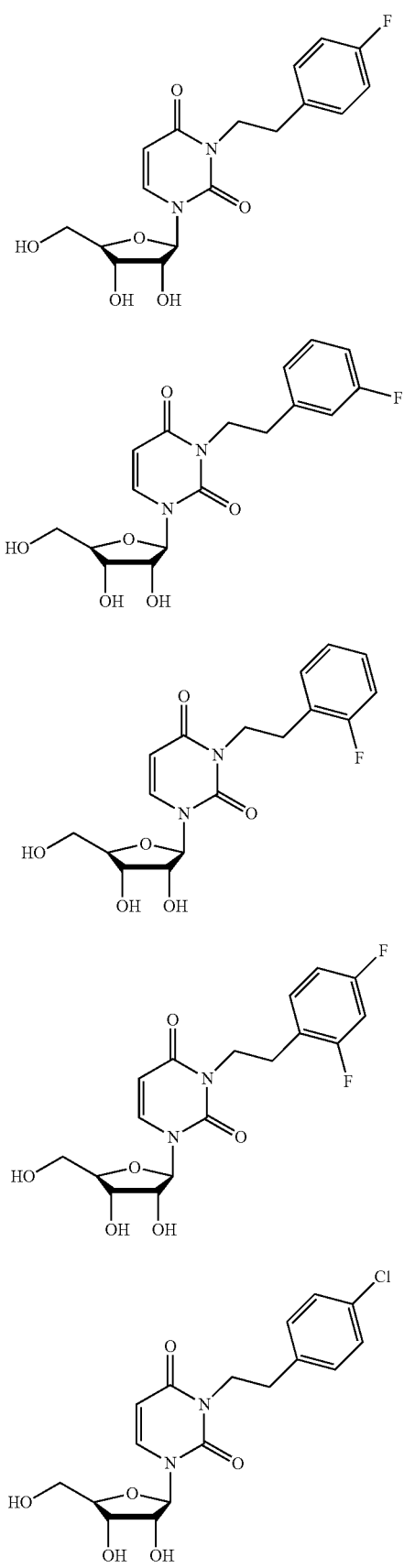
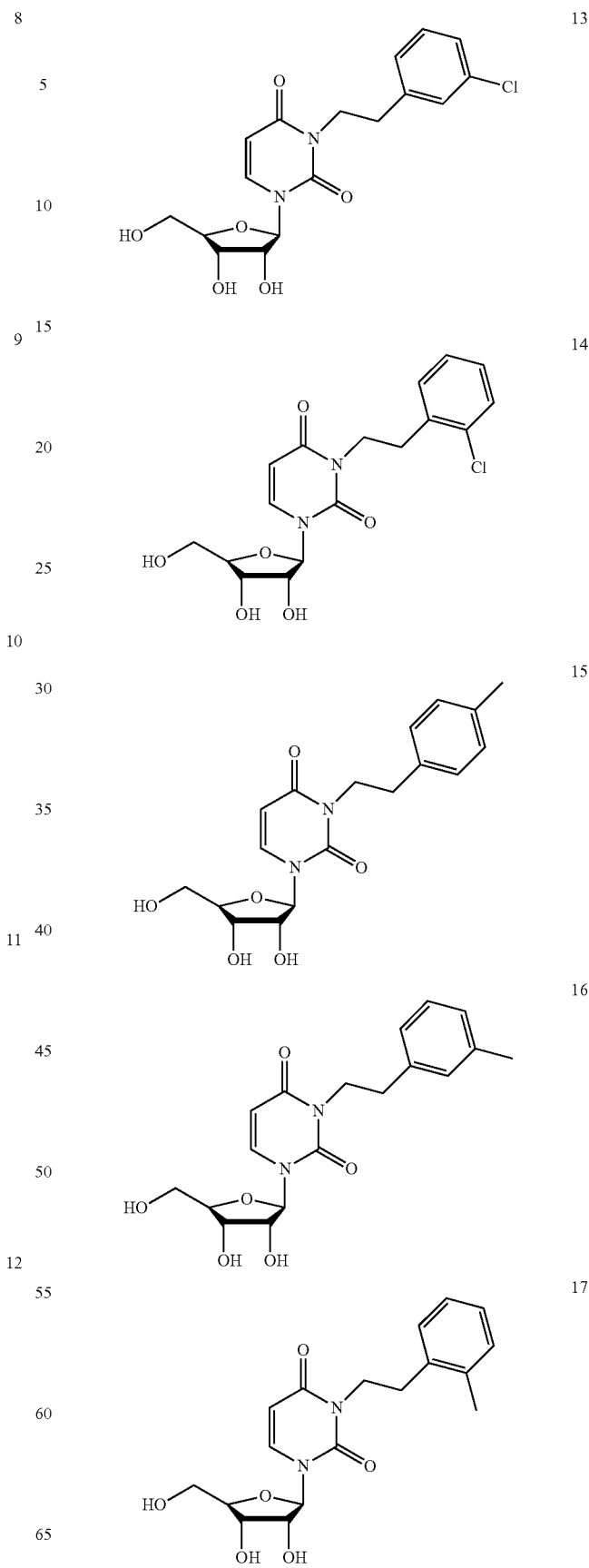

-continued
18
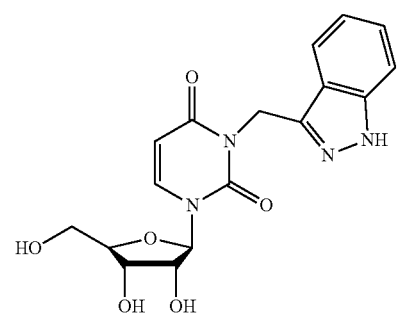
19
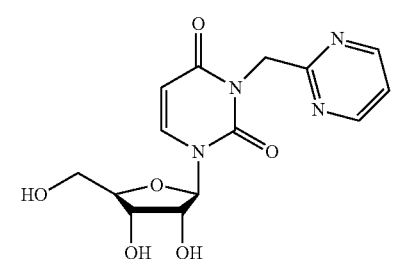
20
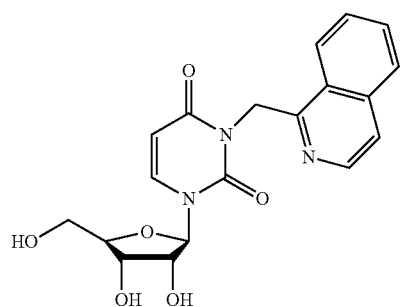
21
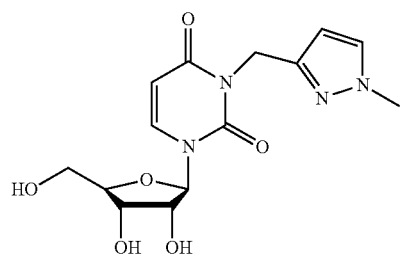
22
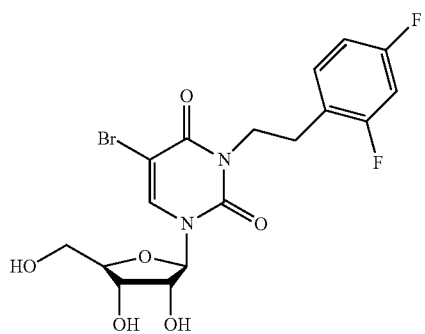
-continued
23
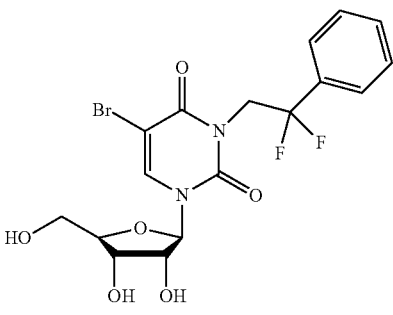
24
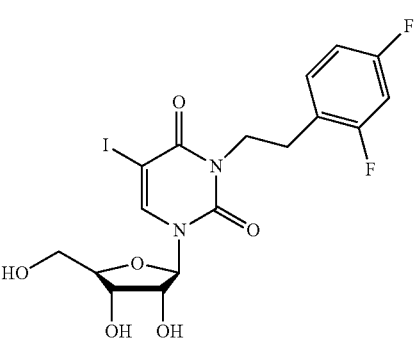
25
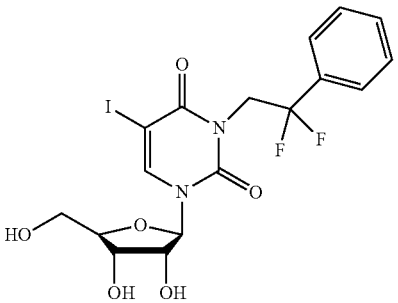
26
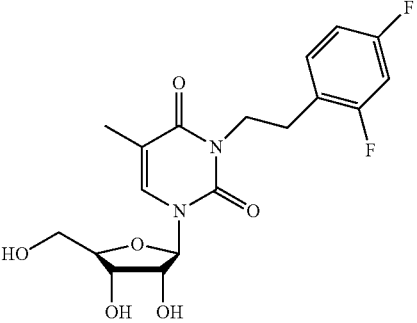
27
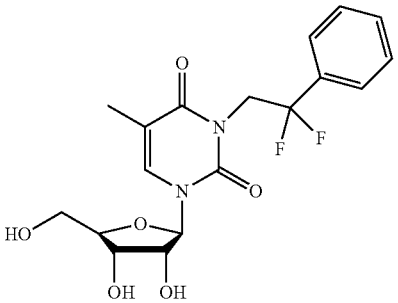

28
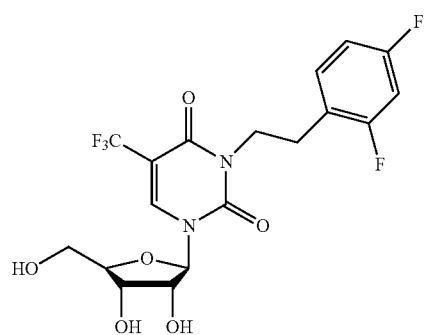
29
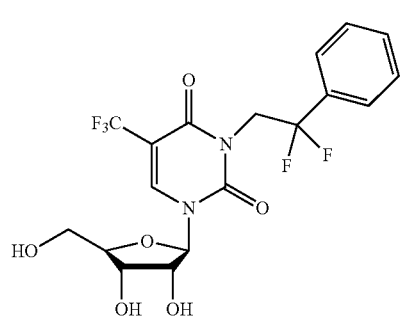
30
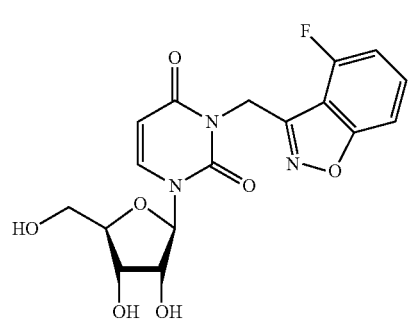
31
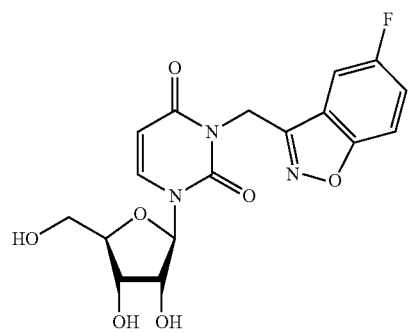
32
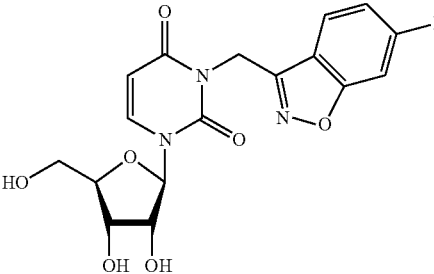
33
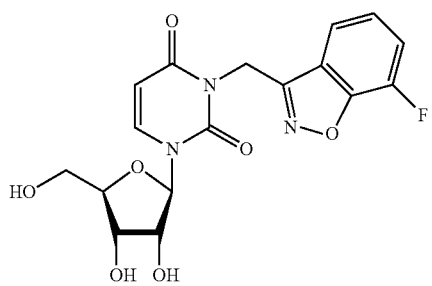
34
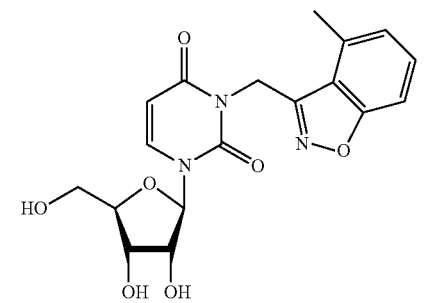
35
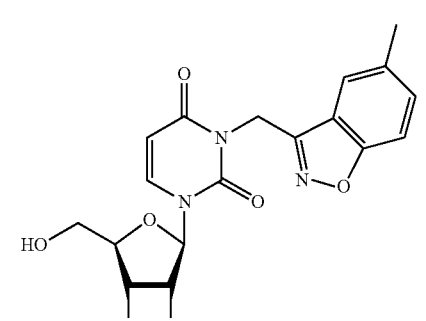
36
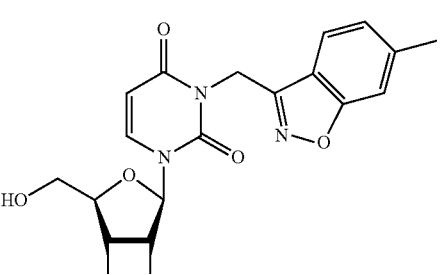
37
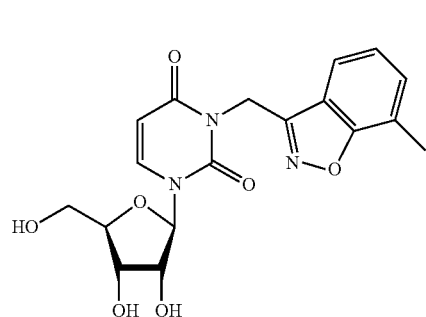

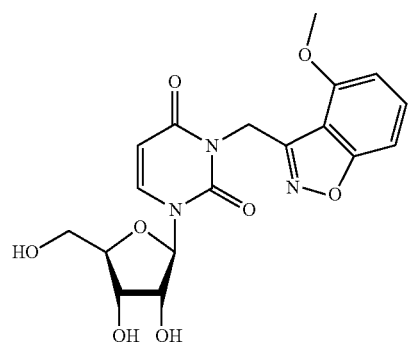
or a phosphorylated analog thereof; or a pharmaceutically acceptable salt thereof.
In some embodiments, the compound is selected from:
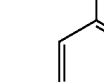
(see Beukers M W et al., (2004) "New, non-adenosine, high-potency agonists for the human adenosine $A_{2B}$ receptor with an improved selectivity profile compared to the reference agonist N-ethylcarboxamidoadenosine," *J. Med. Chem.*37(15):3707-3709);

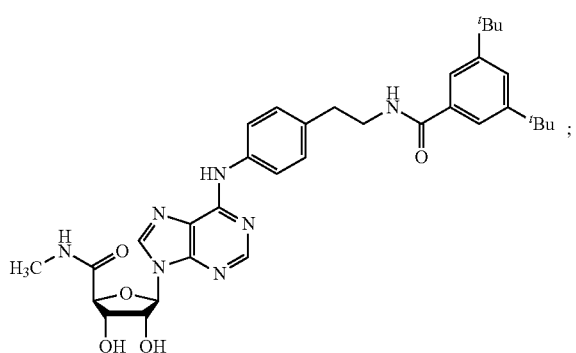

Devine 2010 #7b

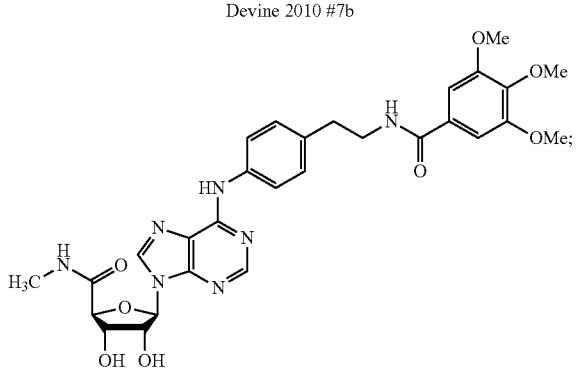

Devine 2010

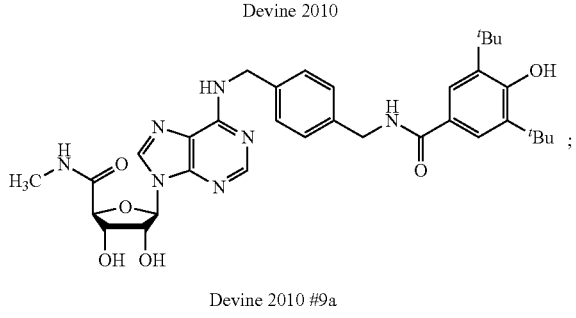

Devine 2010 #9a

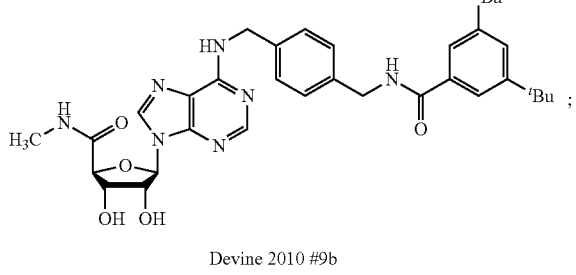

Devine 2010 #9b

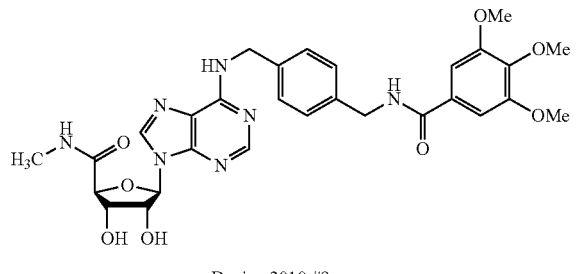

Devine 2010 #9c (see Devine S M et al. "Synthesis and Evaluation of new $A_3R$ agonists," Bioorg Med Chem 18, 3078-3087. 2010; and Muller C E, Jacobson K A. "Recent Developments in adenosine receptor ligands and their potential for novel drugs," Biochimica et Biophysica Acta 1808, 1290-1308. 2011);

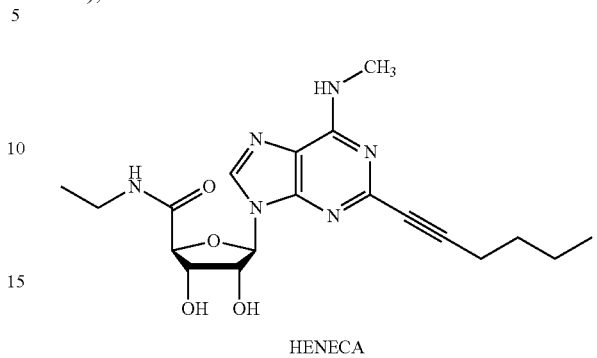

HENECA (see Ben D D et al. "Different efficacy of adenosine and NECA derivatives at the human $A_3$ receptor: Insight into the receptor activation switch," Biochem Pharm 87, 321-331. 2014; and Camaioni E, Di Francesco E, Vittori S, Volpini R, Cristalli G. "Adenosine receptor agonists: synthesis and biological evaluation of the diastereoisomers of 2-(3-hydroxy-3-phenyl-1-propyn-1-yl)NECA," Bioorg Med Chem 1997; 5:2267-75);

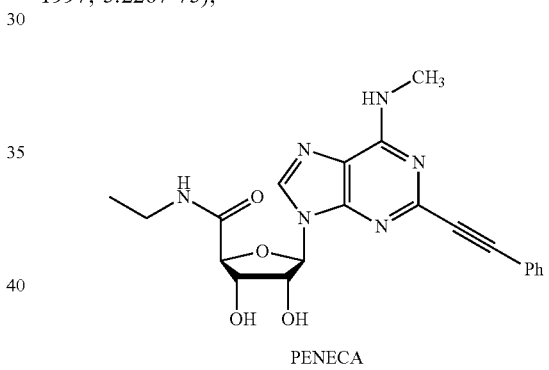

PENECA (see Klotz, K. N. "2-Substituted N-ethylcarboxamidoadenosine derivatives as high-affinity agonists at human $A_3$ adenosine receptors," Naunyn Schmiedebergs Arch Pharmacol. 1999 August; 360(2):103-8; and Cristalli G et al. (1995) "2-Aralkynyl and 2-heteroalkynyl derivatives of adenosine-5'-N-ethyluronamide as selective A2a adenosine receptor agonists," J Med Chem 38:1462-1472);

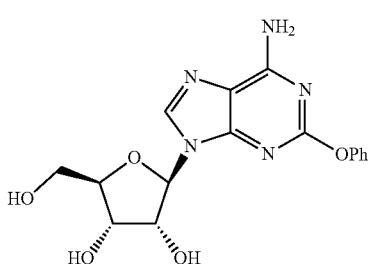 [SMILES: Nc1nc(Oc2ccccc2)nc2c1ncn2[C@@H]1O[C@H](CO)[C@@H](O)[C@H]1O]

(see Kim S et al. "3D quantitative SAR at $A_3R$," J Chem Inf. Model 47, 1225-1233 2007);

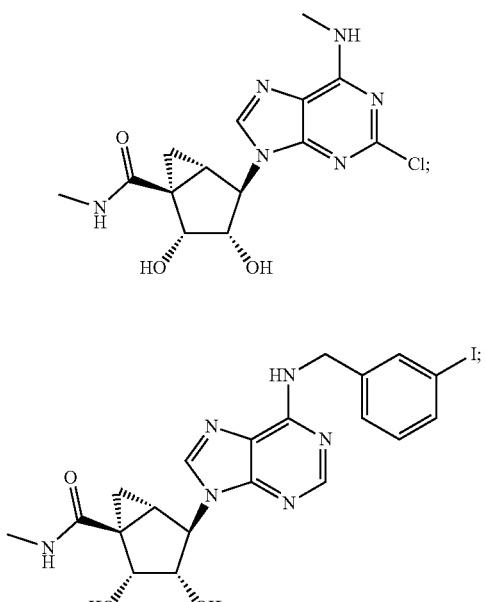

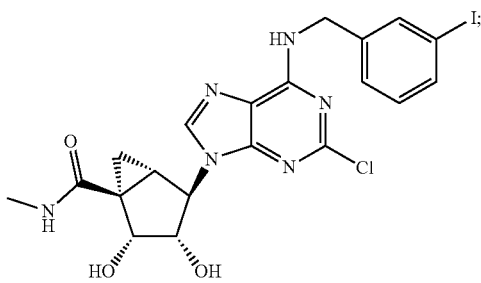

(MRS1898)

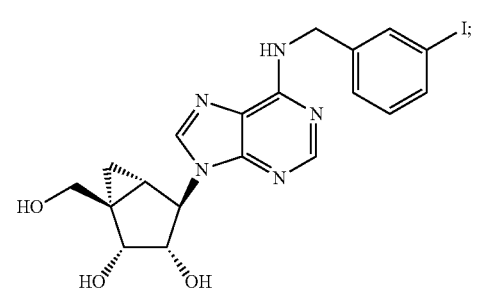

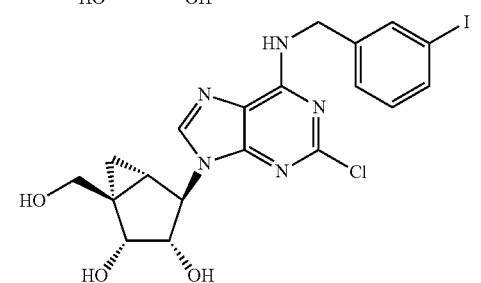

(see Lee, K. et al. "Ring-Constrained (N)-Methanocarba Nucleosides as Adenosine Receptor Agonists," *Bioorg Med Chem Lett* 2001, 11, 1333-1337);

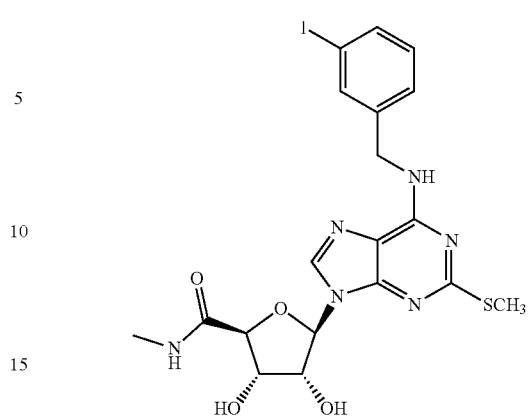

(see Kenneth A. Jacobson et al. Chapter 6. A3 Adenosine Receptor Agonists: History and Future Perspectives pp 96-97. Book—Springer: A3 Adenosine Receptors from Cell Biology to Pharmacology and Therapeutics, 2009);

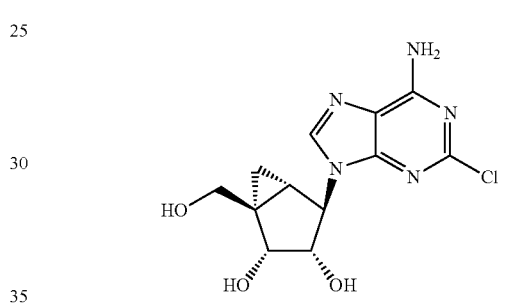

(see Lee K et al. "Ring-Constrained (N)-Methanocarba Nucleosides as Adenosine Receptor Agonists," *Bioorg Med Chem Lett* 2001, 11, 1333-1337; and Gao et al. "Structural Determinants of $A_3R$ Activation: Nucleoside Ligands at the Agonist/Antagonist Boundary," *J. Med. Chem.*, 2002, 45, 4471-4484);

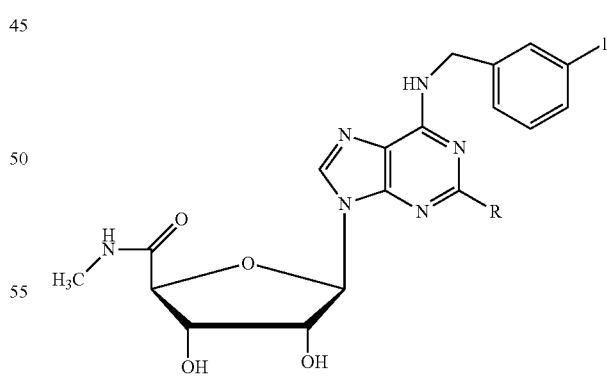

R = H: IB-MECA (CF101)
R = Cl: CHB-MECA (CF102)

(see Muller C E, Jacobson K A, "Recent Developments in adenosine receptor ligands and their potential for novel drugs," Biochimica et Biophysica Acta 2011, 1808, 1290-1308);

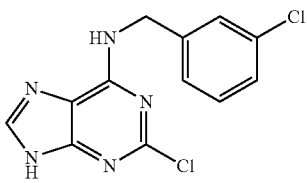 [SMILES: Clc1cccc(CNc2nc(Cl)nc3[nH]cnc23)c1]

(MRS5930; see Jacobson K A et al. "John Daly Lecture: Structure-guided Drug Design for Adenosine and P2Y Receptors," Comp. and Struct. Biotechnology Jour 13. 286-298. 2015);

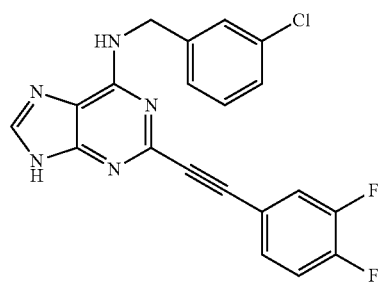 [SMILES: Fc1ccc(C#Cc2nc(NCc3cccc(Cl)c3)c3nc[nH]c3n2)cc1F]

(MRS5923; see Jacobson K A et al. "John Daly Lecture: Structure-guided Drug Design for Adenosine and P2Y Receptors," Comp. and Struct. Biotechnology Jour 13. 286-298. 2015);

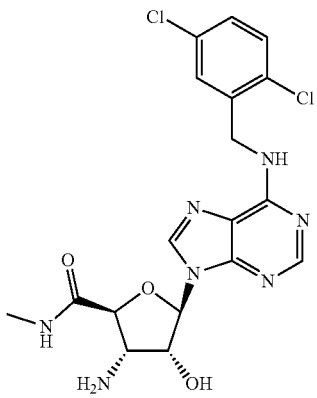 [SMILES: CNC(=O)[C@H]1O[C@@H](n2cnc3c(NCc4cc(Cl)ccc4Cl)ncnc32)[C@H](O)[C@@H]1N]

CP532,903 (see Tracey W R et al. "Novel n6-substituted adenosine 5'-N-methyluronamides with high selectivity for human $A_3R$ reduce ischemic myocardial injury," Am J Physiol Heart Circ Physiol 285. 2003; Muller C E, Jacobson K A, "Recent Developments in adenosine receptor ligands and their potential for novel drugs," Biochimica et Biophysica Acta 1808, 1290-1308. 2011; and Wan T C et al. "The $A_3R$ Agonist CP-532,903 Protects against Myocardial Ischemia/Reperfusion Injury," J. of Pharmacology and Exptl Therapies 324, 1. 2008);

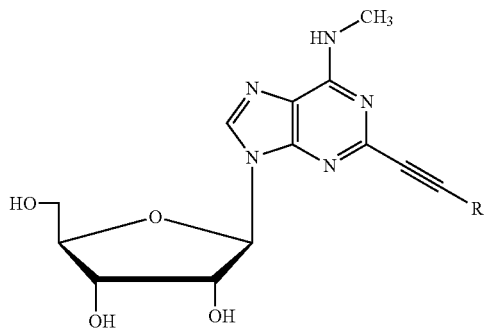

R = $nC_4H_9$: HEMADO
R = Ph: PEMADO (see Volpini R et al. "HEMADO as Potent and Selective Agonists of $hA_3R$," J Med Chem 45, 3271-3279. 2002; Muller C E et al. "Recent Developments in adenosine receptor ligands and their potential for novel drugs," Biochimica et Biophysica Acta 1808, 1290-1308. 2011; and Volpini R et al. "Synthesis and Evaluation of Potent and Highly Selective Agonists for $hA_3R$," J of Med Chem 52, 7897-7900. 2009);

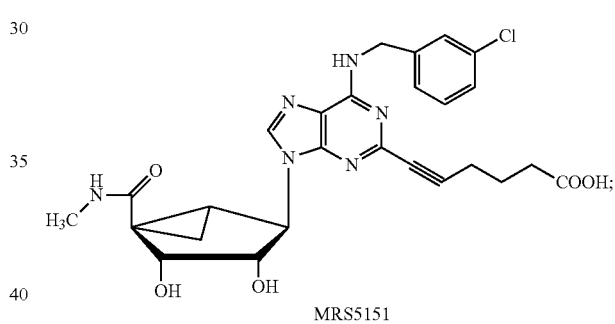

MRS5151

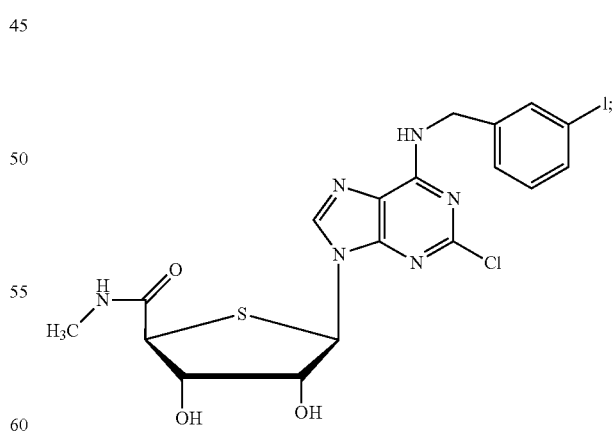

LJ529

(see Muller C E, Jacobson K A. "Recent Developments in adenosine receptor ligands and their potential for novel drugs," Biochimica et Biophysica Acta 1808, 1290-1308. 2011);

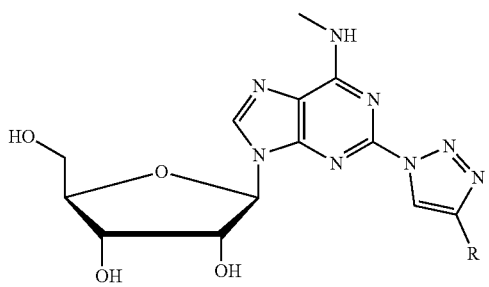

wherein R is H or cyclopentylmethyl;

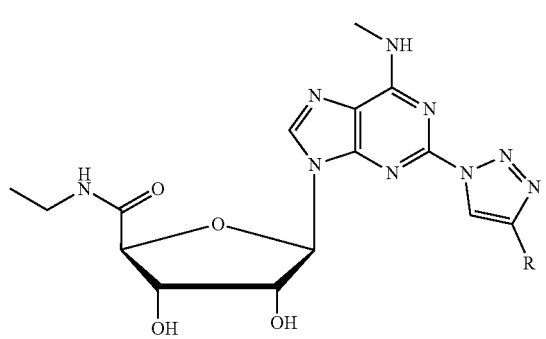

wherein R is H, butyl, or pyridin-2-yl (see Cosyn L. et al., "2-triazole-substituted adenosines," J Med Chem 2006. 49. 7373-7383);

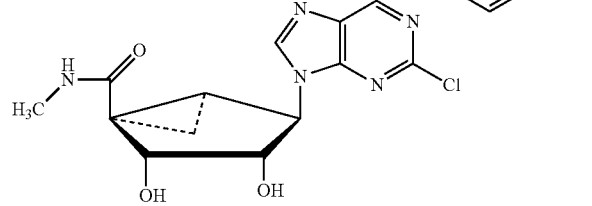

MRS3558 (CF502)

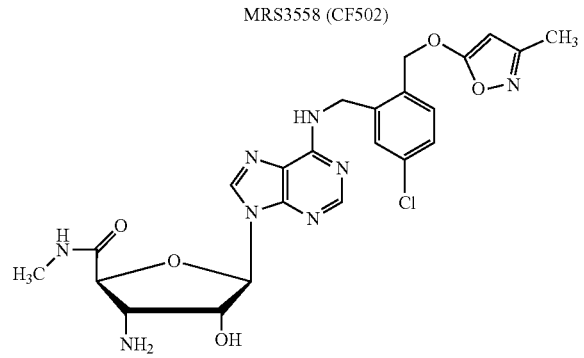

CP608,039

(see Muller C E, Jacobson K A. "Recent Developments in adenosine receptor ligands and their potential for novel drugs," Biochimica et Biophysica Acta 1808, 1290-1308. 2011);

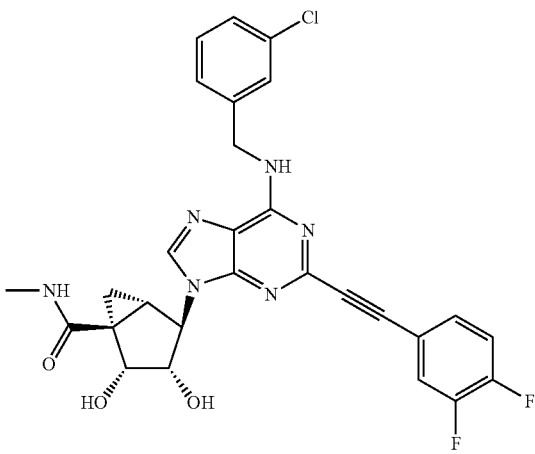

MRS5698

(see Jacobson K A et al. "John Daly Lecture: Structure-guided Drug Design for Adenosine and P2Y Receptors," Comp. and Struct. Biotechnology Jour 13. 286-298. 2015);

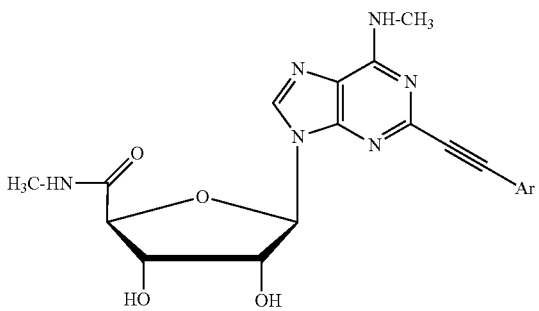

wherein Ar is selected from phenyl, p-CH$_3$CO-phenyl, p-fluorophenyl, or 2-pyridyl (see Volpini R et al. "Synthesis and Evaluation of Potent and Highly Selective Agonists for hA$_3$R," J Med Chem 52, 7897-7900. 2009);

AR132

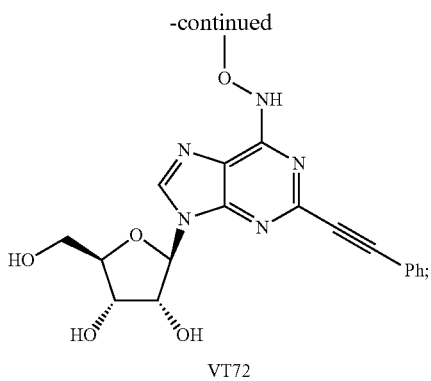

VT72

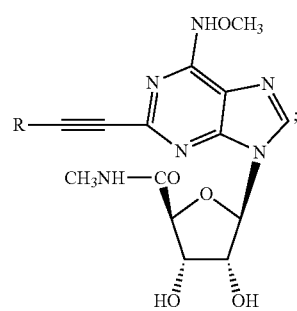

R = C₆H₅, VT158
R = 2-pyridinyl, VT160
R = p-C₆H₄COCH₃, VT163

(see Pugliese A M et al., "Role of A₃R on CA1 hippocampal neurotransmission during OGD," Biochem Pharmacology 74. 2007);

(see Klotz K N "Adenosine receptors and their ligands NS's," Arch Pharmacol. 362. 382-391. 2000); or a pharmaceutically acceptable salt thereof. In some embodiments, the compound is selected from a (N)-methanocarba nucleoside such as those disclosed above; or a pharmaceutically acceptable salt thereof.

In some embodiments, the compound is selected from:

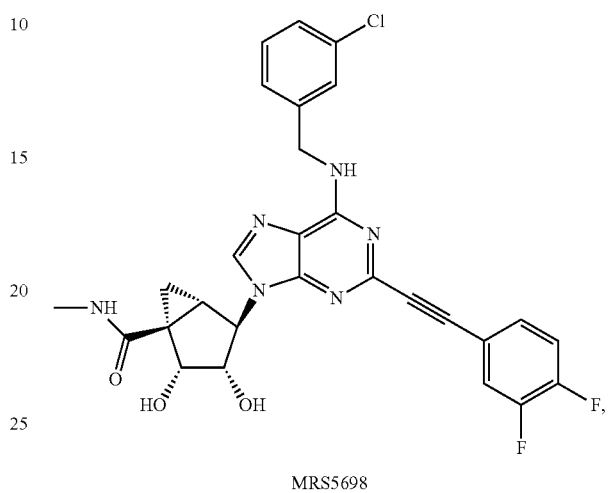

MRS5698

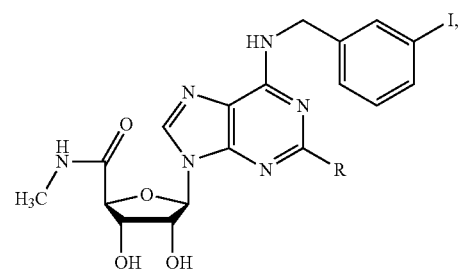

R = H: IB—MECA (CF101)
R = Cl: Cl—IB—MECA (CF102)

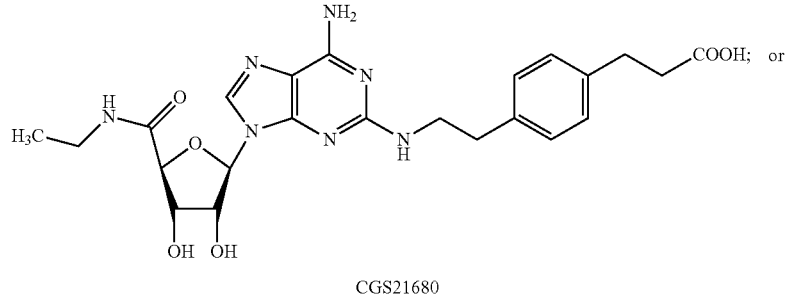

CGS21680

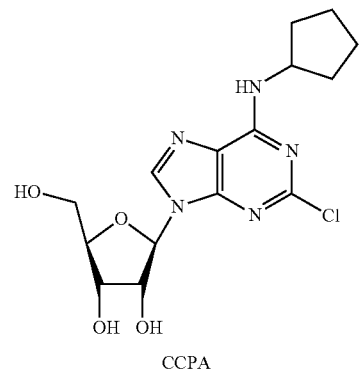

CCPA

-continued
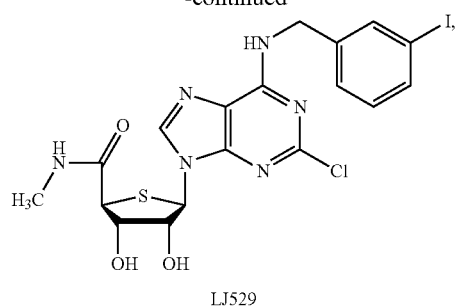
LJ529
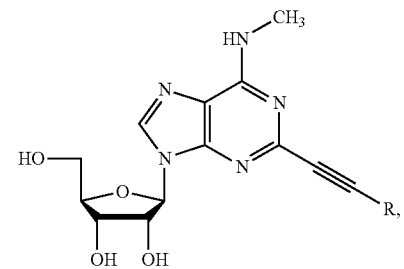
R = nC$_4$H$_9$: HEMADO
R = Ph: PEMADO
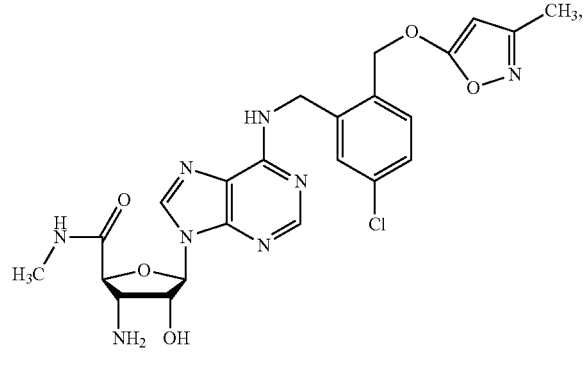
CP608,039
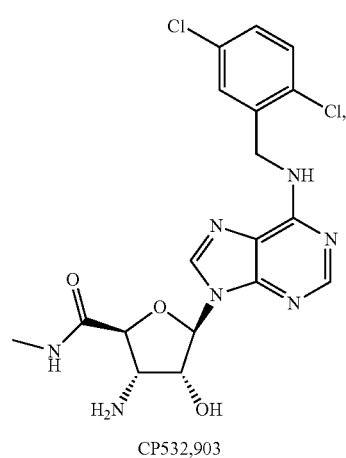
CP532,903
-continued
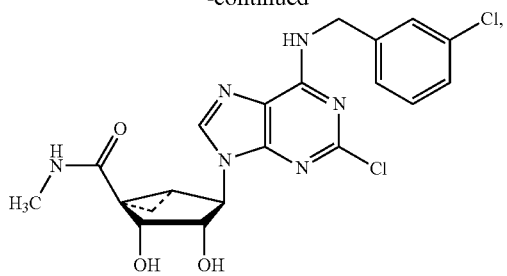
MRS3558 (CF502)
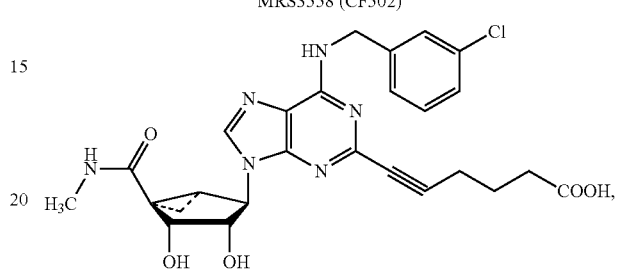
MRS5151
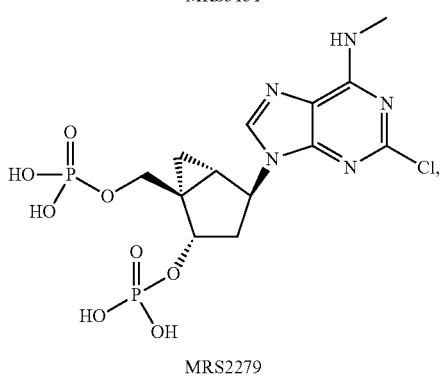
MRS2279
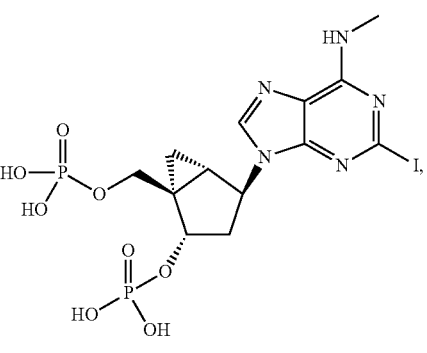
MRS2500
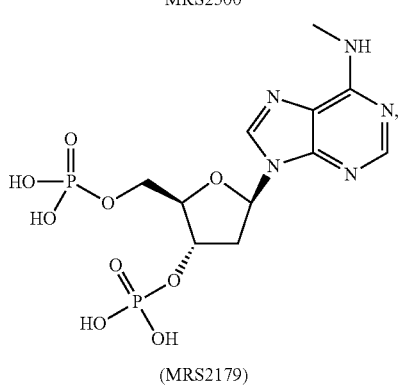
(MRS2179)

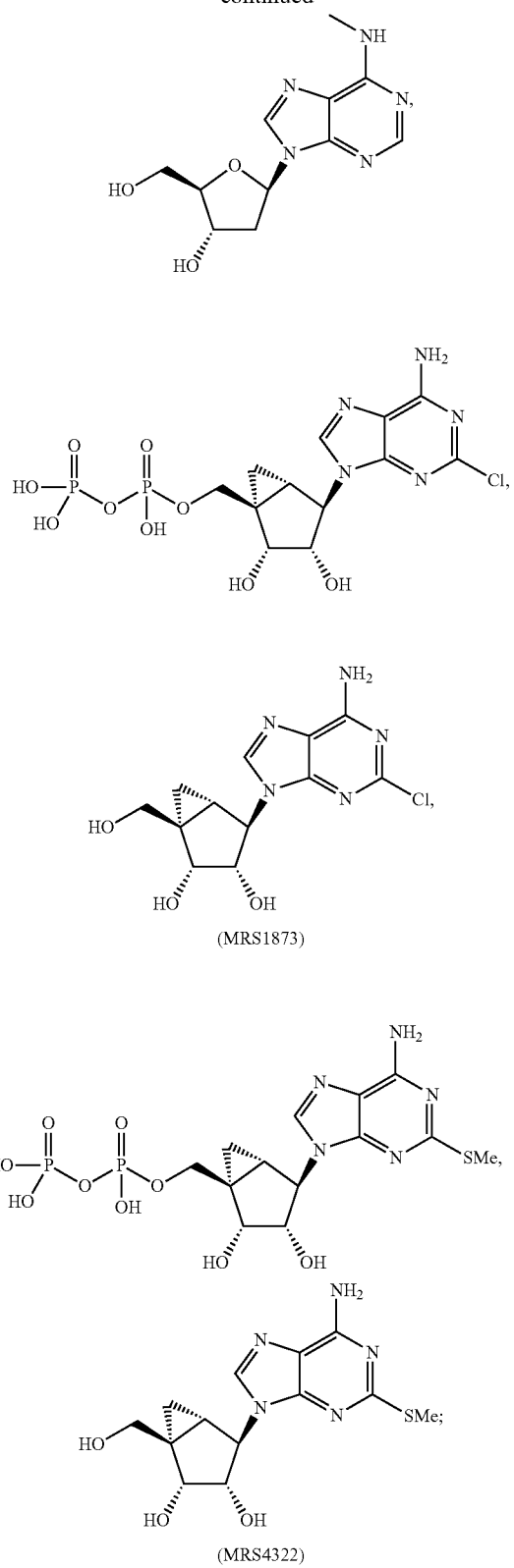

(MRS1873)

(MRS4322)

or a pharmaceutically acceptable salt thereof. In some embodiments, the compound is selected from a (N)-methanocarba nucleoside such as those disclosed above; or a pharmaceutically acceptable salt thereof.

In some embodiments, the compound is selected from

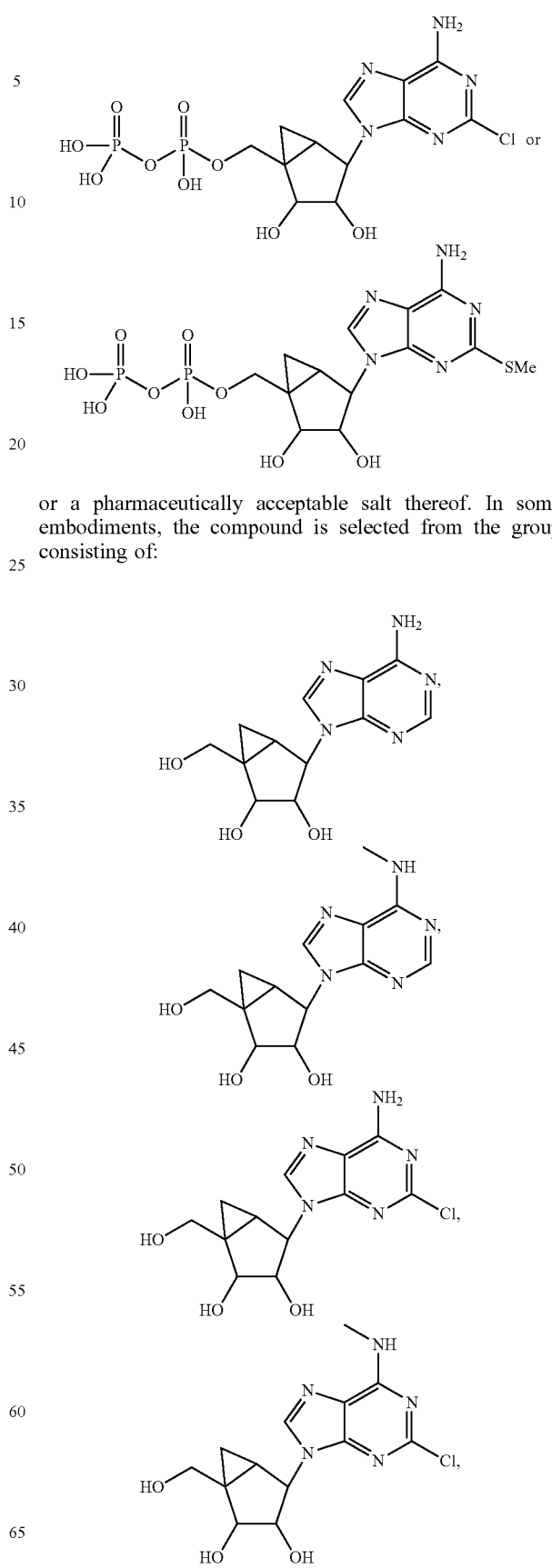

or a pharmaceutically acceptable salt thereof. In some embodiments, the compound is selected from the group consisting of:

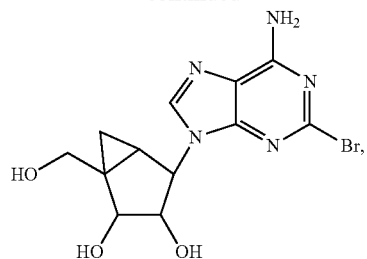
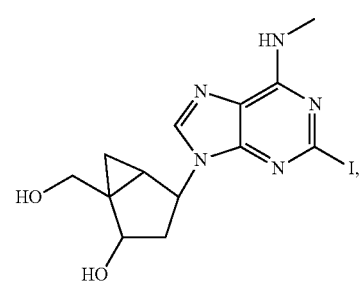
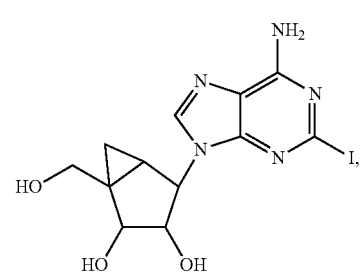
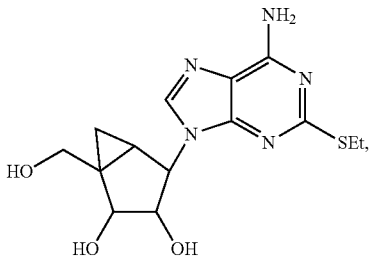
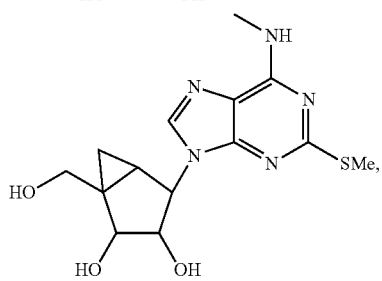
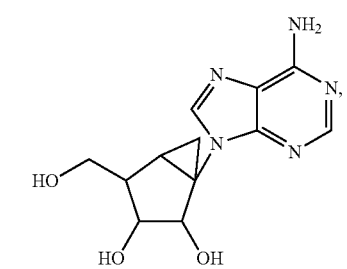
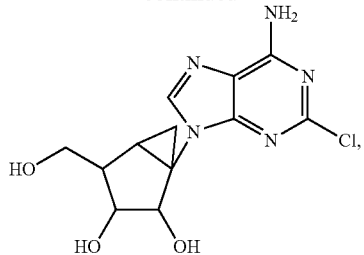
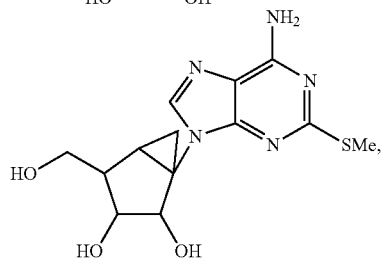
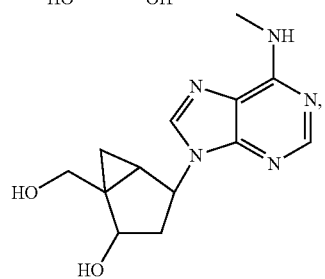
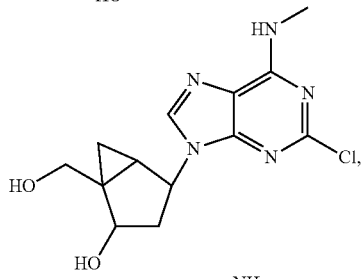
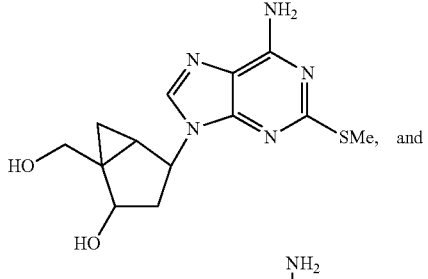
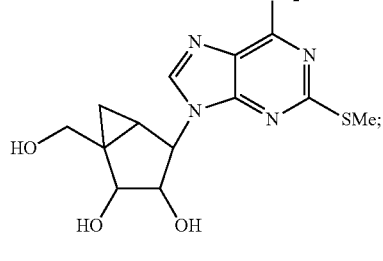
wherein each compound may be in the North or South conformation or the methanocarba sugar may be replaced with a D-ribosugar; or a pharmaceutically acceptable salt thereof; or a mono-, di-, or triphosphate thereof or pharmaceutically acceptable salt of the mono-, di-, or triphosphate. In some embodiments, the methanocarba sugar is a D-(N)- methanocarba sugar. In some embodiments, the methanocarba sugar is a D-(S)-methanocarba sugar.
In some embodiments, the compound is selected from:
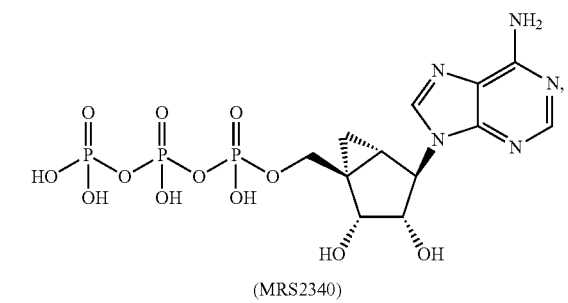
(MRS2340)
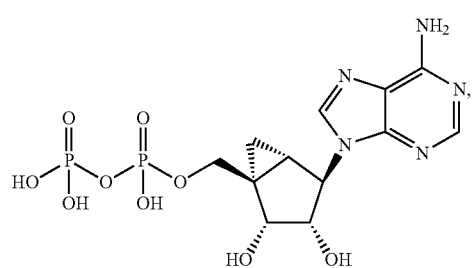
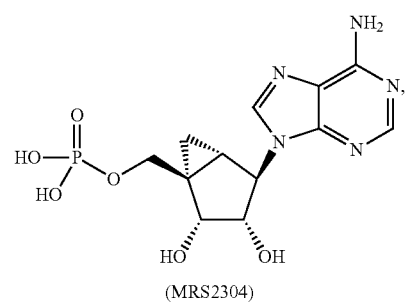
(MRS2304)
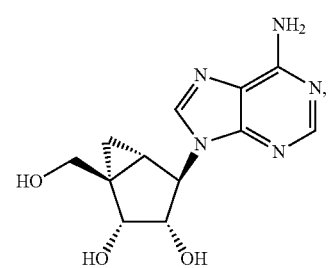
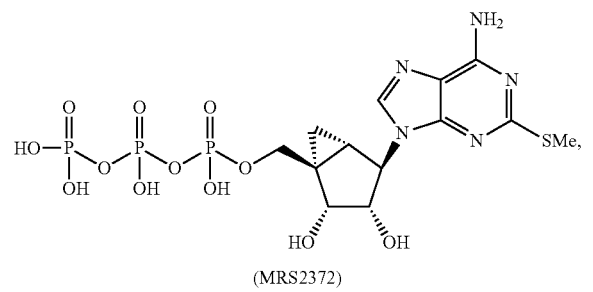
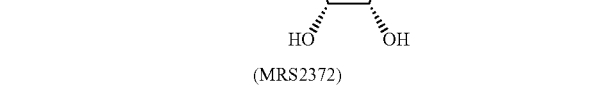
(MRS2372)
-continued
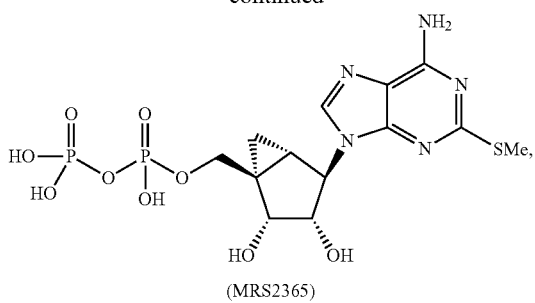
(MRS2365)
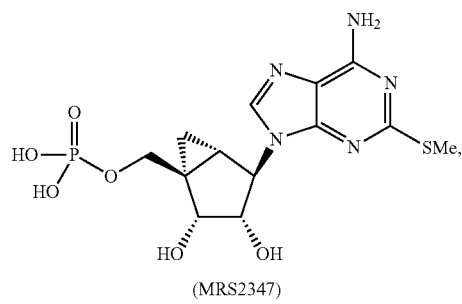
(MRS2347)
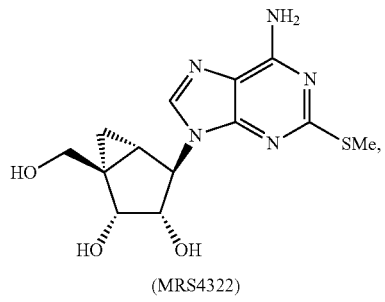
(MRS4322)
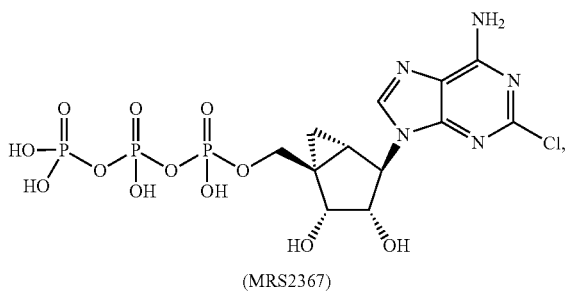
(MRS2367)
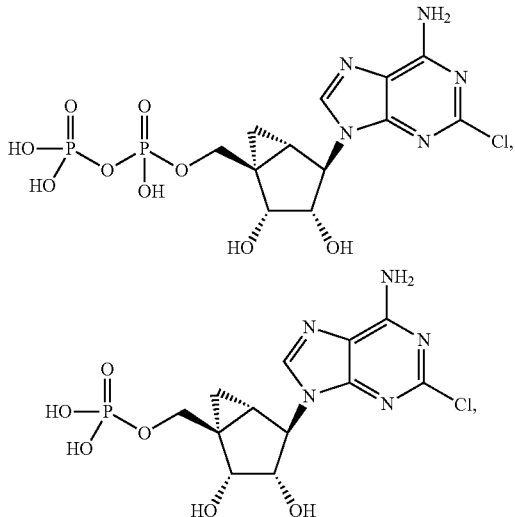
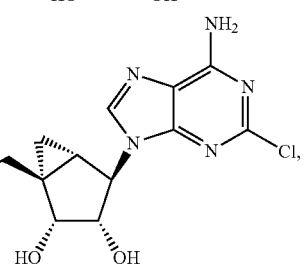

53
-continued
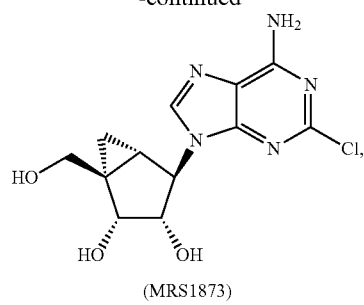
(MRS1873)
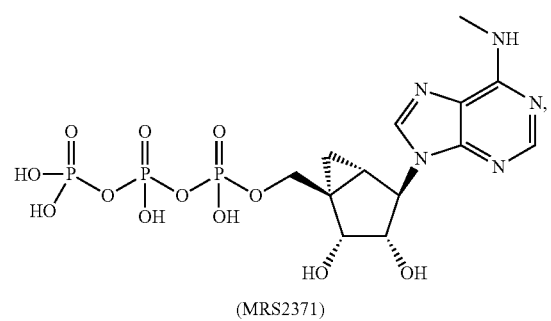
(MRS2371)
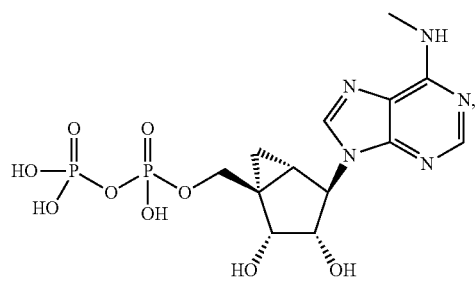
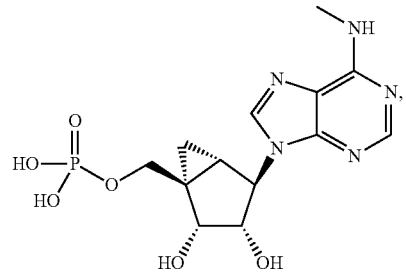
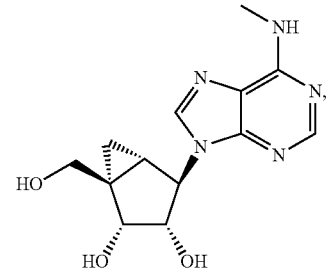
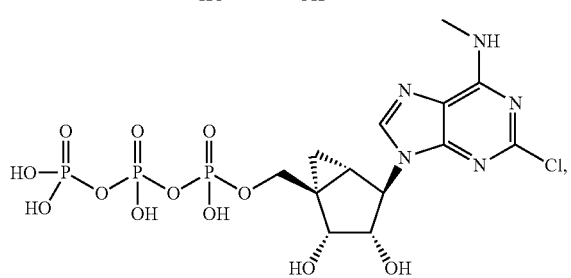
54
-continued
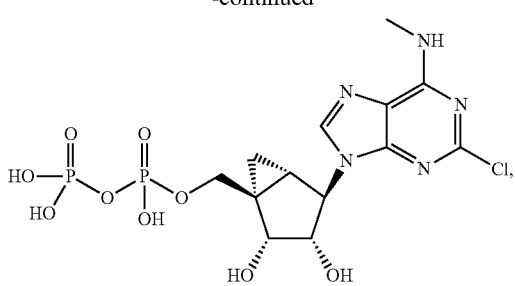
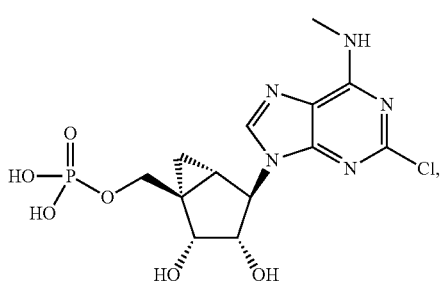
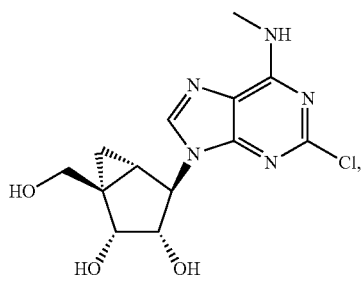
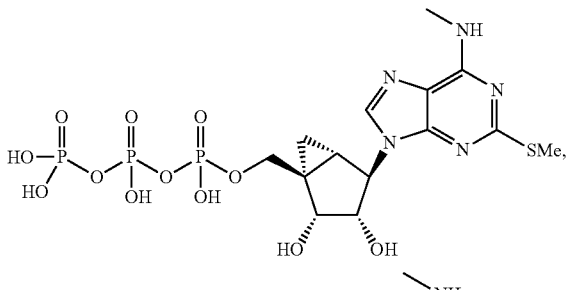
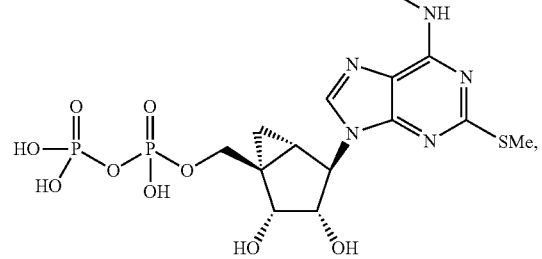
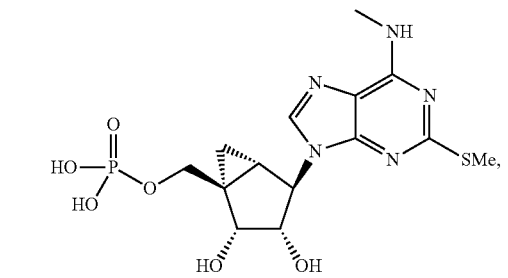

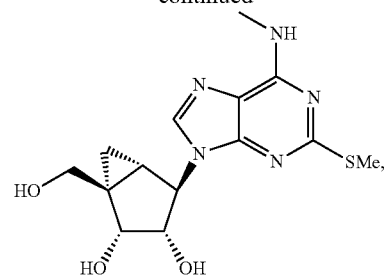
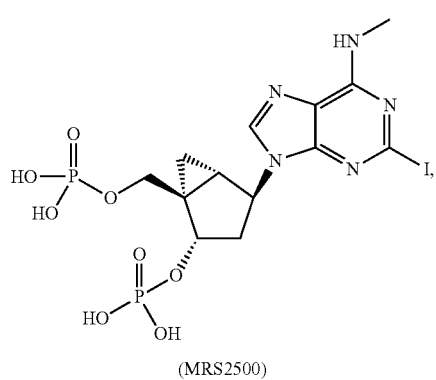
(MRS2500)
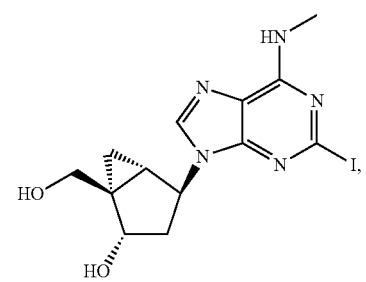
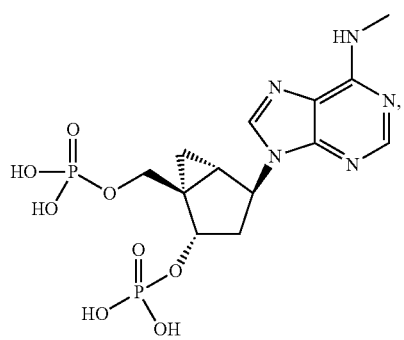
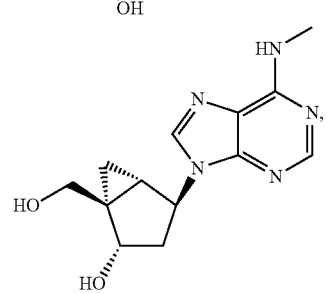
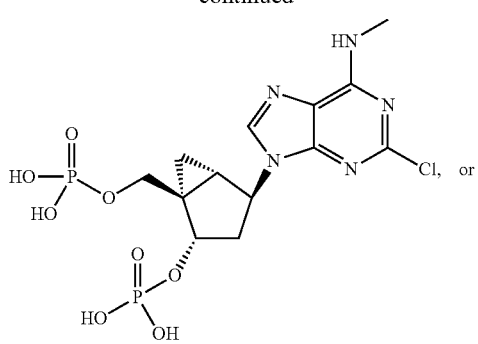
(MRS2279)
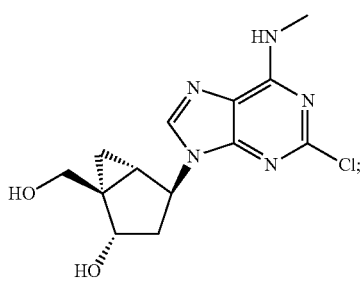
or a pharmaceutically acceptable salt thereof. In some embodiments, the compound is selected from a (N)-methanocarba nucleoside such as those disclosed above; or a pharmaceutically acceptable salt thereof.
In some embodiments, the compound is selected from
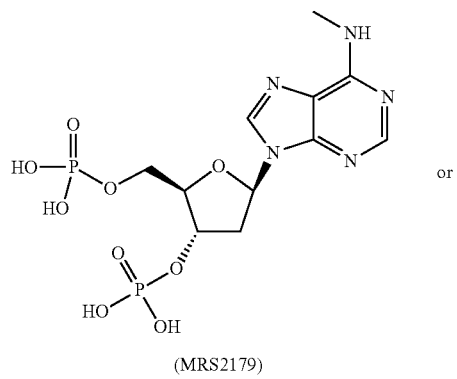
(MRS2179)
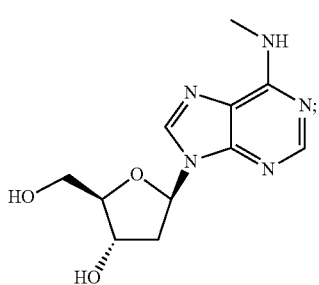
or a pharmaceutically acceptable salt thereof.

In some embodiments, the compound is selected from

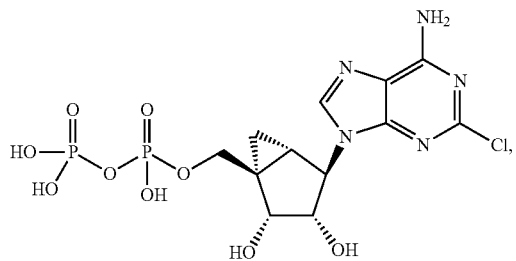

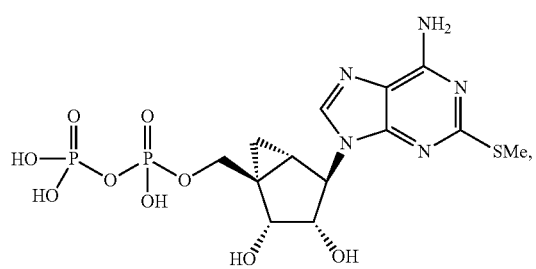

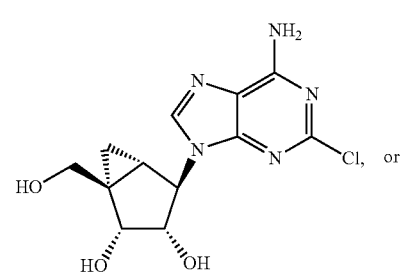

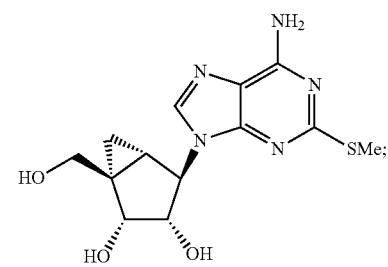

or a pharmaceutically acceptable salt thereof.
In some embodiments, the compound is

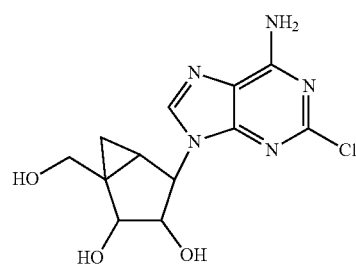 [SMILES: Nc1nc(Cl)nc2c1ncn2C1C(O)C(O)C2(CO)CC12]

or a pharmaceutically acceptable salt thereof. In some embodiments, the compound is

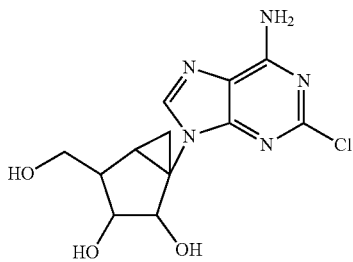 [SMILES: Nc1nc(Cl)nc2c1ncn2C12CC1C(CO)C(O)C2O]

or a pharmaceutically acceptable salt thereof. In some embodiments, the compound is

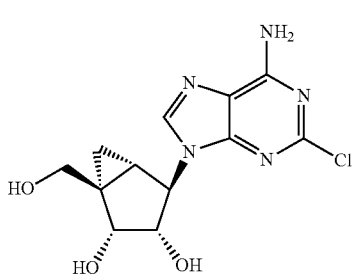 [SMILES: Nc1nc(Cl)nc2c1ncn2[C@H]1[C@H](O)[C@H](O)[C@]2(CO)C[C@H]12]

or a pharmaceutically acceptable salt thereof.
In some embodiments, the compound is

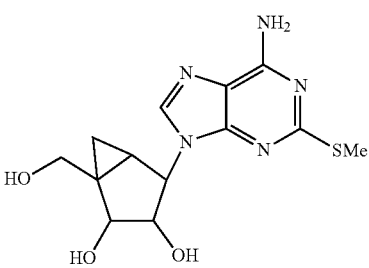 [SMILES: CSc1nc(N)c2ncn(C3C(O)C(O)C4(CO)CC34)c2n1]

or a pharmaceutically acceptable salt thereof. In some embodiments, the compound is

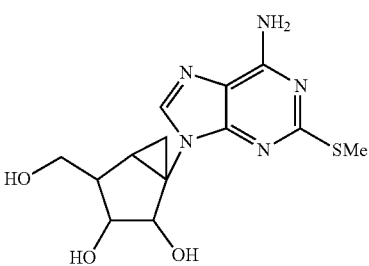 [SMILES: CSc1nc(N)c2ncn(C34CC3C(CO)C(O)C4O)c2n1]

or a pharmaceutically acceptable salt thereof. In some embodiments, the compound is

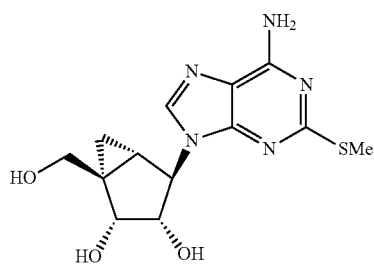 [SMILES: CSc1nc(N)c2ncn([C@H]3[C@H](O)[C@H](O)[C@]4(CO)C[C@H]34)c2n1]

or a pharmaceutically acceptable salt thereof. In some embodiments, the compound is

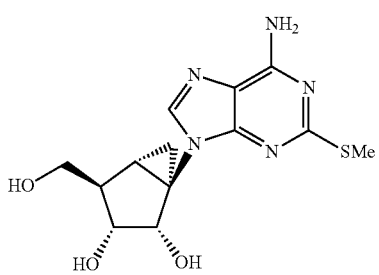 [SMILES: CSc1nc(N)c2ncn([C@]34C[C@H]3[C@H](CO)[C@@H](O)[C@H]4O)c2n1]

or a pharmaceutically acceptable salt thereof. In some embodiments, the compound is

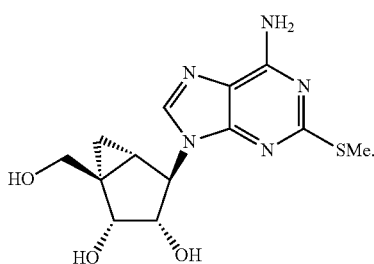 [SMILES: CSc1nc(N)c2ncn([C@H]3[C@H](O)[C@H](O)[C@]4(CO)C[C@H]34)c2n1]

In one aspect, the present invention provides a pharmaceutical composition comprising a disclosed compound or a pharmaceutically acceptable salt thereof and a pharmaceutically acceptable excipient. In some embodiments, the compound is

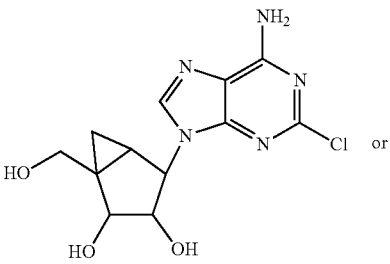

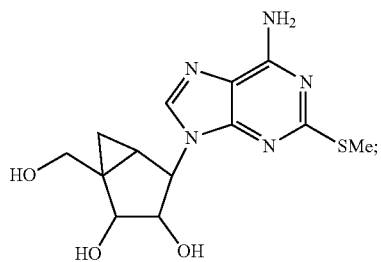

or a pharmaceutically acceptable salt thereof. In some embodiments, the compound is

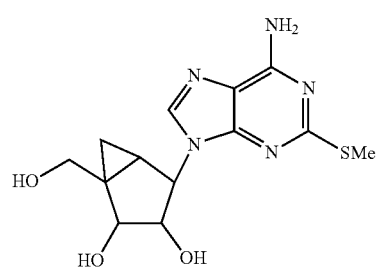 [SMILES: CSc1nc(N)c2ncn(C3C(O)C(O)C4(CO)CC34)c2n1]

or a pharmaceutically acceptable salt thereof. In some embodiments, the compound is

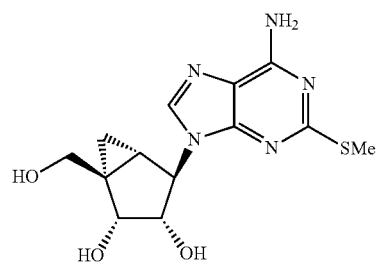 [SMILES: CSc1nc(N)c2ncn([C@H]3[C@H](O)[C@H](O)[C@]4(CO)C[C@H]34)c2n1]

or a pharmaceutically acceptable salt thereof. In some embodiments, the compound is

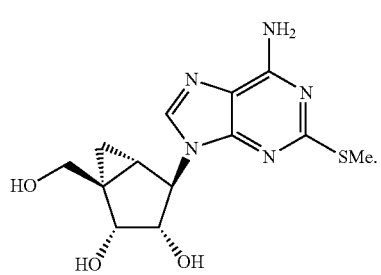 [SMILES: CSc1nc(N)c2ncn([C@H]3[C@H](O)[C@H](O)[C@]4(CO)C[C@H]34)c2n1]

Figure 15:
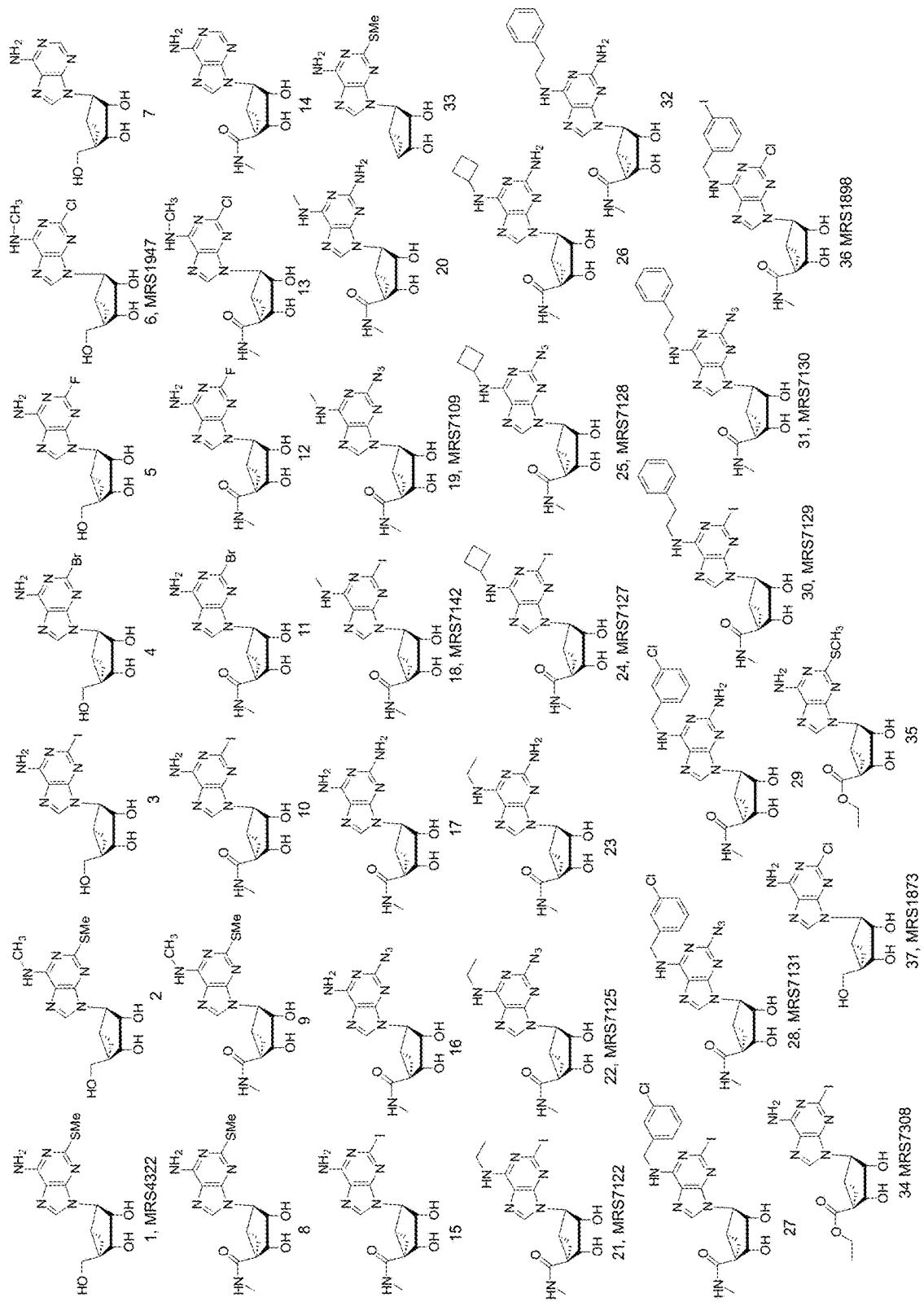
FIG. 15 shows the structures of certain compounds suitable for use in the claimed invention.

In some embodiments, the compound is selected from those in FIG. 15, or a pharmaceutically acceptable salt thereof. In some embodiments, the compound is selected from

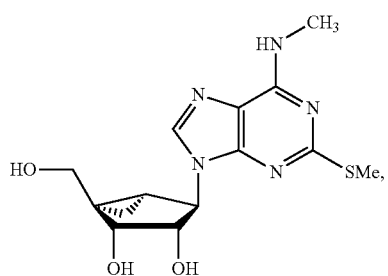
2
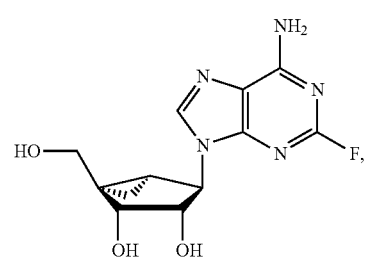
5
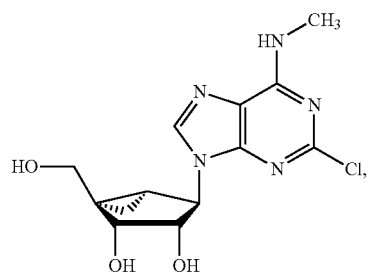
MRS1947
6
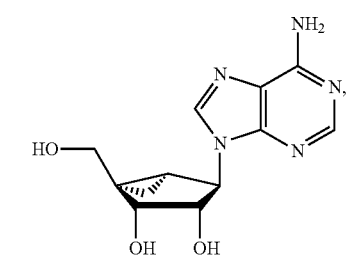
7
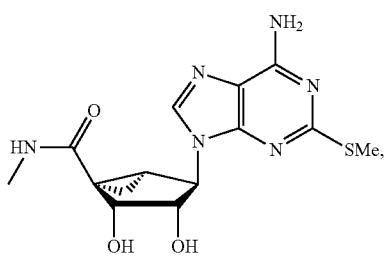
8
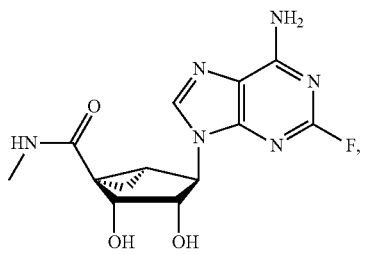
12
-continued
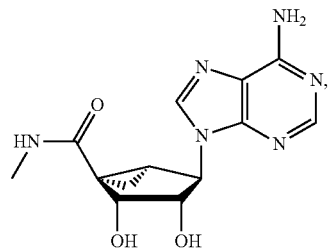
14
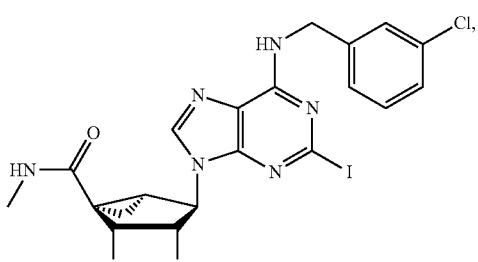
15
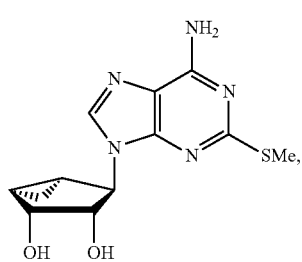
33
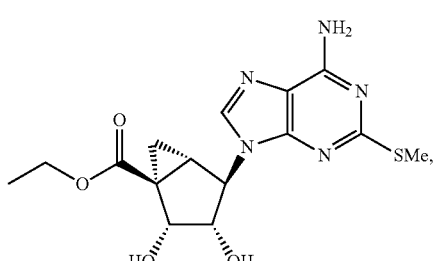
35
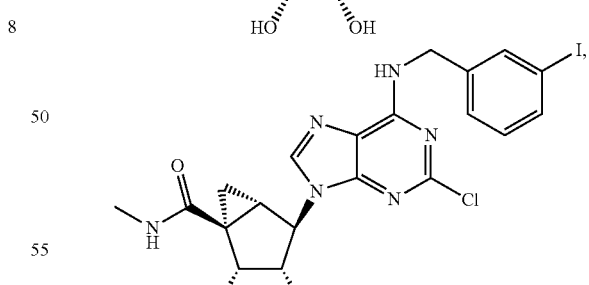
(MRS1898)
or MRS1873; or a pharmaceutically acceptable salt thereof.
In one aspect, the present invention provides a method of treating a brain or central nervous system (CNS) injury or condition selected from traumatic brain injury (TBI) or stroke, comprising administering to a patient in need thereof an effective amount of a compound selected from:

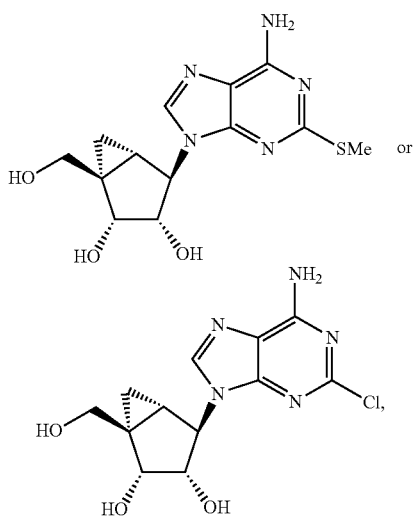

a pharmaceutically acceptable salt thereof, or a pharmaceutically acceptable composition comprising the same.

In some embodiments, the compound is

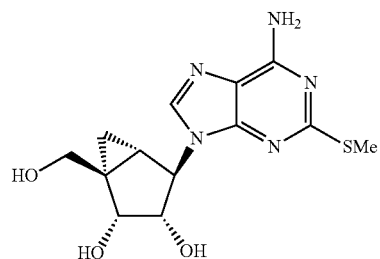 [SMILES: CSc1nc(N)c2ncn([C@H]3[C@H](O)[C@H](O)[C@]4(CO)C[C@H]34)c2n1]

or a pharmaceutically acceptable salt thereof.

In some embodiments, the compound is

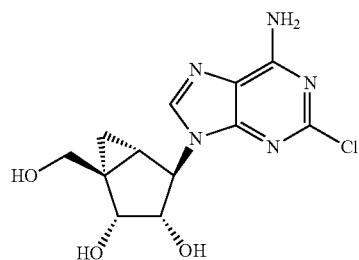 [SMILES: Nc1nc(Cl)nc2c1ncn2[C@H]1[C@H](O)[C@H](O)[C@]2(CO)C[C@H]12]

or a pharmaceutically acceptable salt thereof.

In some embodiments, the brain or central nervous system (CNS) injury or condition is TBI.

In some embodiments, the TBI is selected from concussion, blast injury, combat-related injury, or a mild, moderate or severe blow to the head.

In some embodiments, the compound is administered within 24 hours of the TBI or stroke.

In some embodiments, the compound is administered within 8 hours of the TBI or stroke.

In some embodiments, the compound is administered at least during the first 8-48 hours following the TBI or stroke.

In some embodiments, the brain or central nervous system (CNS) injury or condition is stroke.

In some embodiments, the compound is administered chronically to treat the stroke during the time period after the stroke has occurred as it resolves.

In some embodiments, neuroprotection or neurorestoration is increased in the patient as compared with an untreated patient.

In some embodiments, the compound is a biased partial agonist at a human $A_3$ adenosine receptor ($A_3R$).

In some embodiments, the $A_3R$ is partially agonized in a manner biased toward neuroprotective functions of the $A_3R$ receptor.

In some embodiments, the compound is administered orally, intravenously, or parenterally.

In one aspect, the present invention provides a method of increasing neuroprotection or neurorestoration in a patient who has suffered a TBI or stroke, comprising administering to a patient in need thereof an effective amount of a compound selected from

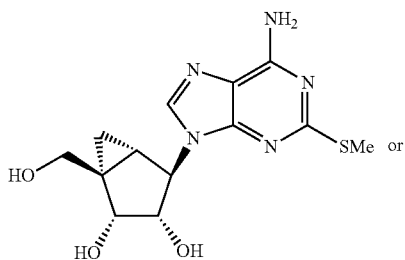

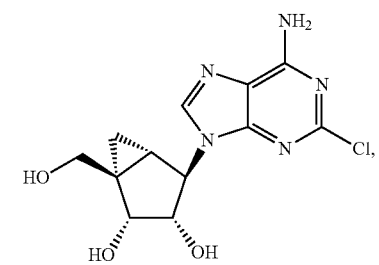

a pharmaceutically acceptable salt thereof, or a pharmaceutically acceptable composition comprising the same.

In some embodiments, the compound is

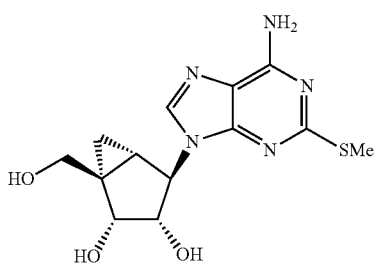 [SMILES: CSc1nc(N)c2ncn([C@H]3[C@H](O)[C@H](O)[C@]4(CO)C[C@H]34)c2n1]

or a pharmaceutically acceptable salt thereof.

In some embodiments, the compound is

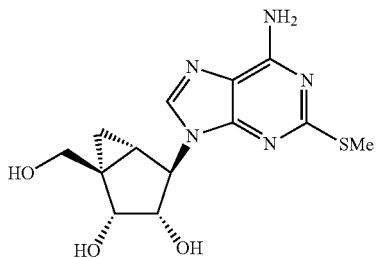

or a pharmaceutically acceptable salt thereof.

In some embodiments, the compound is

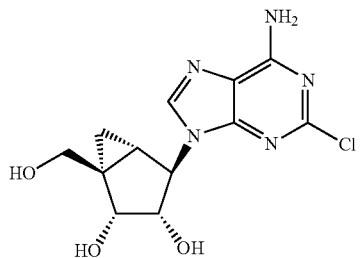 [SMILES: Nc1nc(Cl)nc2c1ncn2[C@H]1[C@H](O)[C@H](O)[C@]2(CO)C[C@H]12]

or a pharmaceutically acceptable salt thereof.

In some embodiments, the neuroprotection or neurorestoration decreases the recovery period after the TBI or stroke as compared with an untreated patient.

In some embodiments, the compound is a biased partial agonist at a human $A_3$ adenosine receptor ($A_3R$) and the $A_3R$ is partially agonized in a manner biased toward neuroprotective functions of the $A_3R$ receptor.

In some embodiments, the compound is administered orally, intravenously, or parenterally.

In some embodiments, the compound or pharmaceutically acceptable salt thereof has an unbound fraction in plasma of at least 0.7 or at least 0.08 unbound fraction in brain, or both.

In some embodiments, the compound or pharmaceutically acceptable salt thereof has an unbound fraction in plasma of at least 0.7 or at least 0.08 unbound fraction in brain, or both.

In one aspect, the present invention provides a method of treating an injury, disease, or condition selected from traumatic brain injury (TBI), stroke, a neurodegenerative condition, or a heart or cardiovascular disease, comprising administering to a patient in need thereof an effective amount of an agonist of an $A_3$ adenosine receptor ($A_3R$) selected from

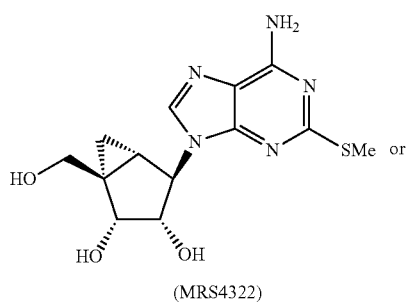
(MRS4322)

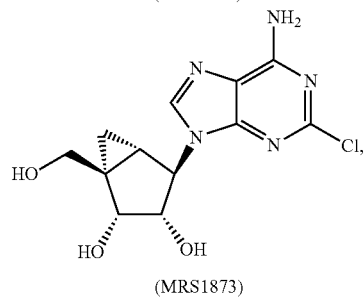
(MRS1873)

a pharmaceutically acceptable salt thereof, or a pharmaceutically acceptable composition comprising the same.

In some embodiments, the compound is

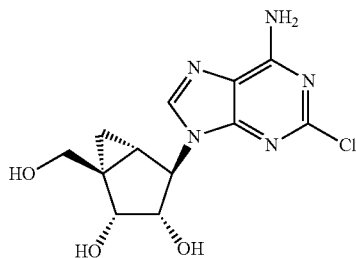 [SMILES: Nc1nc(Cl)nc2c1ncn2[C@H]1[C@H](O)[C@H](O)[C@]2(CO)C[C@H]12]

or a pharmaceutically acceptable salt thereof.

In some embodiments, the injury, disease, or condition is TBI.

In some embodiments, the TBI is selected from concussion, blast injury, combat-related injury, or a mild, moderate or severe blow to the head.

In some embodiments, the injury, disease, or condition is a stroke selected from ischemic stroke, hemorrhagic stroke, subarachnoid hemorrhage, cerebral vasospasm, or transient ischemic attacks (TIA).

In some embodiments, the neurodegenerative disease is selected from Alzheimer's Disease (AD), Parkinson's Disease (PD), Huntington's Disease (HD), Multiple Sclerosis (MS), amyotrophic lateral sclerosis (ALS), chronic traumatic encephalopathy (CTE), or a neurodegenerative condition caused by a virus, alcoholism, tumor, toxin, or repetitive brain injuries.

In some embodiments, the injury, disease, or condition is Parkinson's Disease.

In some embodiments, the injury, disease, or condition is Alzheimer's Disease, migraine, brain surgery, or a neurological side effect associated with cancer chemotherapy.

In some embodiments, the heart or cardiovascular disease is selected from cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis.

In some embodiments, the heart or cardiovascular disease is cardiac ischemia or myocardial infarction.

In some embodiments, the compound is administered chronically to treat the stroke, cardiac ischemia, or myocardial infarction during the time period after the injury has occurred as it resolves.

In some embodiments, neuroprotection or neurorestoration is increased in the patient as compared with an untreated patient.

In some embodiments, the $A_3R$ is agonized in a biased manner toward neuroprotective functions of the $A_3R$ receptor via preferential activation of intracellular calcium mobilization with less, or no, activation of other A₃R-mediated pathways, or via preferential activation of Gq11-mediated intracellular calcium mobilization, Gi-mediated modulation of cAMP production, or Gi-mediated phosphorylation of ERK1/2 and Akt.

In some embodiments, the A₃R is partially agonized in a manner biased toward cardioprotective functions of the A₃R receptor via preferential activation of intracellular calcium mobilization with less, or no, activation of other A₃R-mediated pathways, or via preferential activation of Gq11-mediated intracellular calcium mobilization, Gi-mediated modulation of cAMP production, or Gi-mediated phosphorylation of ERK1/2 and Akt.

In some embodiments, the method increases neuroprotection or neurorestoration in a patient who is suffering from a neurological side effect associated with or resulting from cancer chemotherapy or brain surgery.

In some embodiments, the compound is administered orally.

In one aspect, the present invention provides a method of increasing neuroprotection or neurorestoration in a patient who has suffered a TBI or stroke, thereby treating the TBI or stroke, comprising administering to a patient in need thereof an effective amount of an agonist of an A₃ adenosine receptor (A₃R) selected from

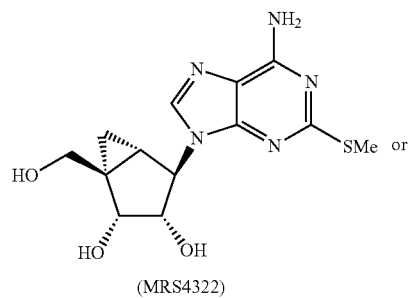
(MRS4322)

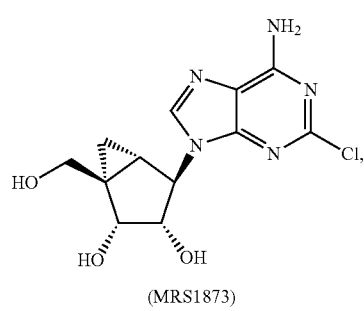
(MRS1873)

a pharmaceutically acceptable salt thereof, or a pharmaceutically acceptable composition comprising the same.

In one aspect, the present invention provides a method of increasing cardioprotection or regeneration of damaged heart tissue in a patient who has suffered a cardiac ischemia or myocardial infarction, thereby treating the cardiac ischemia or myocardial infarction, comprising administering to a patient in need thereof an effective amount of an agonist of an A₃ adenosine receptor (A₃R) selected from

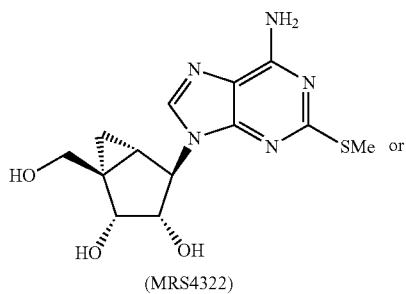
(MRS4322)

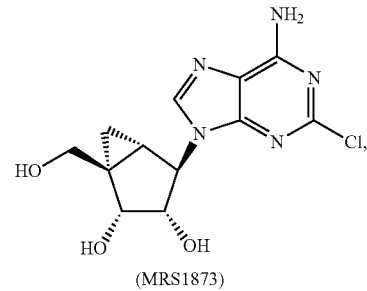
(MRS1873)

a pharmaceutically acceptable salt thereof, or a pharmaceutically acceptable composition comprising the same.

In some embodiments, the compound is

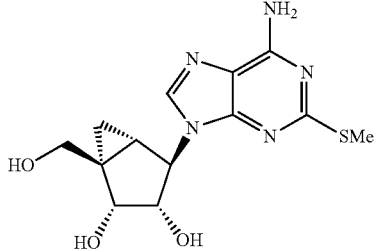 [SMILES: CSc1nc(N)c2ncn([C@H]3[C@H](O)[C@H](O)[C@]4(CO)C[C@H]34)c2n1]

or a pharmaceutically acceptable salt thereof.

In some embodiments, the compound is

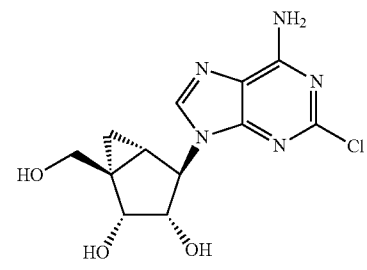 [SMILES: Nc1nc(Cl)nc2c1ncn2[C@H]1[C@H](O)[C@H](O)[C@]2(CO)C[C@H]12]

or a pharmaceutically acceptable salt thereof.

In some embodiments, the recovery period after the TBI, stroke, cardiac ischemia, or myocardial infarction is decreased as compared with an untreated patient.

In some embodiments, the A₃R is partially agonized in a manner biased toward neuroprotective functions of the A₃R receptor.

In some embodiments, the A₃R is partially agonized in a manner biased toward cardioprotective functions of the A₃R receptor.

In some embodiments, the compound is administered orally.

In some embodiments, the compound is a biased agonist of an $A_3R$ with improved cardioprotection function relative to a full $A_3R$ agonist.

In some embodiments, the compound is a biased agonist of an $A_3R$ with improved cardioprotection function relative to a full $A_3R$ agonist via preferential activation of one or more of the following $A_3R$-mediated pathways: activation of Gq11-mediated intracellular calcium mobilization, Gi-mediated modulation of cAMP production, Gi-mediated phosphorylation of ERK1/2 and Akt, or modulation of Beta-Arrestin activation.

In some embodiments, the compound is a biased agonist of an $A_3R$ with improved cardioprotection function relative to a full $A_3R$ agonist via preferential activation of intracellular calcium mobilization with less or no activation of the other $A_3R$-mediated pathways.

In some embodiments, the compound is a partial agonist of the $A_3R$ with improved cardioprotection function relative to a full $A_3R$ agonist.

The amount of a disclosed compound (i.e., active agent) that should be present in a composition for use a disclosed method or a disclosed pharmaceutical composition will generally be a therapeutically effective amount. A "therapeutically effective amount" or dose (or "effective amount") refers to that amount of the active agent sufficient to result in a desired therapeutic result, such as activation of neuroprotection, neuroregeneration, and/or improvement in cognitive or neurological function. Toxicity and therapeutic efficacy of compositions of active agents can be determined by procedures known in the art in cell cultures or experimental animals, e.g., for determining the $LD_{50}$ (the dose lethal to 50% of the test group) and the $ED_{50}$ (the dose therapeutically effective in 50% of the test group). The dose ratio between toxic and therapeutic effects is the therapeutic index and it can be expressed as the ratio $LD_{50}/ED_{50}$. Compositions which exhibit large therapeutic indices are advantageous. Data obtained from cell culture assays and animal studies can be used in formulating a range of dosages for use in humans. In some embodiments, the dosage of such compositions lies within a range of circulating concentrations that include the $ED_{50}$ with little or no toxicity. The dosage may vary within this range depending upon the dosage form employed and the route of administration utilized.

In some embodiments, the effective dose and/or desired therapeutic result are established by comparing the test subject or patient's cognitive function or another parameter for at least two measurements; however, more than two measurements may also be used. The initial cognitive function measurement establishes an initial baseline for the test subject or patient. The cognitive function can be measured using an established cognitive test such as the delayed verbal recall task of the revised Wechsler Memory Scale. A further test after treatment with the cognitive test will establish a second measurement. An effective amount is established when the comparison of the second measurement to the first measurement demonstrates an improvement of at least about 1%. In some embodiments, the improvement in cognitive function, as measured by the delayed verbal recall task of the revised Wechsler Memory Scale, is between about 1% and 20%. In some embodiments, the improvement is between about 1% and 10%. In some embodiments, the improvement is between about 1% and 5%. It is understood by one skilled in the art that other methods of determining cognitive function improvement are equally applicable as long as they do not measure stages of dementia.

Accordingly, the invention encompasses methods of improving cognitive or neurological function by administering an effective amount of a disclosed compound to a subject in need thereof, wherein the enhancement in neurological and cognitive function is measured as a score increase between 1% and 20% in the in the delayed verbal recall task score of the revised Wechsler Memory Scale.

Disclosed methods of treatment may encompass administration of a disclosed compound as needed to obtain the desired therapeutic effect. The composition can be administered as long as necessary to maintain the desired therapeutic effect. In some embodiments, the compound is administered between about one and 12 months. In some embodiments, the compound is administered between one and six months. In some embodiments, the compound is administered between one and three months.

In one aspect of the invention, a disclosed compound is administered in an amount between about 5 mg/day and 10 g/day. In some embodiments, each dose of the compound is in an amount between about 5 mg/dose and 10 g/dose. For example, satisfactory results are obtained by oral administration of a disclosed compound of the invention at dosages between about 0.05 and 10 mg/kg/day, between about 0.1 and 7.5 mg/kg/day, between about 0.1 and 2 mg/kg/day, or 0.5 mg/kg/day administered once or, in divided doses, 2 to 4 times per day. For parenteral administration, for example by i.v. drip or infusion, dosages between about 0.01 and 5 mg/kg/day, between about 0.05 and 1.0 mg/kg/day and between about 0.1 and 1.0 mg/kg/day can be used. Suitable daily dosages for patients are thus between about 2.5 and 500 mg p.o., between about 5 and 250 mg p.o., between about 5 and 100 mg p.o., or between about 0.5 and 250 mg i.v., between about 2.5 and 125 mg i.v. and between about 2.5 and 50 mg i.v.

3. Uses, Formulation and Administration

Pharmaceutically Acceptable Compositions

According to another embodiment, the invention provides a composition comprising a disclosed compound and a pharmaceutically acceptable carrier, adjuvant, or vehicle. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

In other embodiments, pharmaceutically acceptable compositions of this invention are formulated for intravenous (IV) administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the treatment of various diseases and conditions, such as brain injuries and neurodegenerative conditions, and the various methods disclosed herein.

The activity of a compound utilized in the present invention may be assayed in vitro, in vivo or in a cell line. In vitro assays include assays that determine modulation or binding to a protein. Detailed conditions for assaying a compound are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of a disclosed disease or condition, or associated condition or symptom. The exact amount required will vary from subject to subject, depending on the species, age, and general condition of the subject, the severity of the disease or condition, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, in some embodiments a mammal, or in certain other embodiments a human.

Pharmaceutically acceptable compositions of this invention can be administered to humans and other animals orally, sublingually, rectally, parenterally, intracisternally, intravaginally, intraperitoneally, topically (as by powders, ointments, or drops), intraocularly (such as eye drops), bucally, as an oral or nasal spray, or the like, depending on the severity of the disease or condition being treated. In certain embodiments, the compounds of the invention may be administered orally or parenterally at dosage levels of about 0.01 mg/kg to about 50 mg/kg or from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a)

fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

As depicted in the Examples below, in certain exemplary embodiments, compounds are prepared and used according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The contents of each document cited in the specification are herein incorporated by reference in their entireties.

EXEMPLIFICATION

Example 1: Pharmacokinetics of MRS4322 Following Intraperitoneal Administration to Mice Purpose This study was designed to determine the plasma and brain concentrations of MRS4322 following intraperitoneal administration of a dose used in mouse photothrombosis and traumatic brain injury models.

Methods

Chemicals: MRS4322 was obtained courtesy Dr. Ken Jacobson of the National Institute of Diabetes, Digestive and Kidney Diseases (Bethesda, MD). Analytical-grade tolbutamide was obtained from commercial supplies at Seventh Wave Laboratories (Maryland Heights, MO). All other chemicals were obtained from Sigma-Aldrich (St. Louis, MO).

Animals: Female C576BL/6J mice weighing approximately 0.02 kg were used for this study, supplied by the University of Texas Health Sciences Center (San Antonio, TX). All studies were conducted under approved University of Texas Health Sciences Center IACUC protocols.

Drug Administration: MRS4322 was solubilized in DMSO and then diluted in saline to prepare dosing solution. Final dosing solution concentration of MRS4322 was 100 µM. A 100 µL volume of dosing solution was administered intraperitoneally to each mouse per 20 gram body weight; MRS4322 was administered intraperitoneally at 0.16 mg/kg or 0.5 µmol/kg. Three mice were administered MRS4322 for each sampling timepoint.

Tissue Sampling: Blood and brain samples were obtained at 0, 0.083, 0.25, 0.5, 1, 2 and 8 hours post-dose. At each timepoint, mice (3/timepoint) were euthanized in a carbon monoxide chamber. Whole blood was obtained by cardiac puncture into Microtainer tubes containing heparin and immediately centrifuged for preparation of plasma; plasma was stored at −80° C. At each timepoint, whole brain samples were obtained by decapitation, rinsed in ice-cold phosphate-buffered saline and weighed. Brain samples were then immediately flash-frozen in liquid nitrogen and stored at −80° C.

Bioanalysis

Plasma and brain concentrations of MRS4322 were determined by LC-MS/MS utilizing tolbutamide as an internal standard. The following table outlines the LC and MS/MS conditions employed:

TABLE 1

Bioanalytical Methods for MRS4322 Plasma and Brain Concentration Determinations
Bioanalytical Methods System Components

| Module | Manufacturer | Model |
|---|---|---|
| HPLC | Shimadzu | Prominence LC-20AD Binary Pumps |
| Autosampler | Leap | Prominence Sil-30AC |
| Mass Spectrometer | AB Sciex | 4000 Qtrap |

HPLC Method

| Column | Phenomenex Kinetex C18 (2.1 × 50 mm, 2.6 μm) |
|---|---|
| Elution | Gradient, 0.4 mL/min Mobile Phase A: 0.1% Formic Acid Mobile Phase B: 0.1% Formic Acid in Acetonitrile |

MS Detection and Calibration for MRS4322 in Mouse Plasma

Peak Name: Tolbutamide
Use as Internal Standard
Q1/Q3 Masses:
271.20/155.20 Da
Peak Name: MRS4322
Internal Standard:
Tolbutamide
Q1/Q3 Masses:
324.10/182.00 Da

| Fit | Linear | Weighting | 1/(x * x) |
|---|---|---|---|
| Intercept | 0.000447 | | |
| Slope | 0.00141 | | |
| Correlation coefficient | 0.9996 | | |
| Use Area | | | |

TABLE 1-continued

Bioanalytical Methods for MRS4322 Plasma and Brain Concentration Determinations
Bioanalytical Methods MS Detection and Calibration for MRS4322 in Mouse Brain Homogenate Peak Name: Tolbutamide
Use as Internal Standard
Q1/Q3 Masses:
271.20/155.20 Da
Peak Name: MRS4322
Internal Standard:
Tolbutamide
Q1/Q3 Masses:
324.10/182.00 Da

| Fit | Linear | Weighting | 1/(x * x) |
|---|---|---|---|
| Intercept | 0.0000465 | | |
| Slope | 0.000883 | | |
| Correlation coefficient | 0.9996 | | |
| Use Area | | | |

For each tissue matrix, standard curves were created and LLOQ/ULOQ concentrations determined. The calibration range for the MRS4322 plasma concentration standard curve was 2.42-242 ng/mL. The calibration range for MRS4322 brain concentrations was 2.41-233 ng/mL.

For bioanalysis of brain concentrations of MRS4322, brain samples were homogenized in ice-cold phosphate-buffered saline in a 4× dilution. Aliquots of the resulting diluted brain homogenate were treated with acetonitrile and analyzed by LC-MS/MS. Because of the 4× homogenate dilution, the calibration range of the MRS4322 brain standard curve was translated to 9.64-932 ng/gm. In several samples, MRS4322 was detectable but fell below the brain LLOQ of 9.64 ng/gm but were above background; in these cases the final reported brain concentration was extrapolated based on MS peak heights.

Results

Figure 1B:
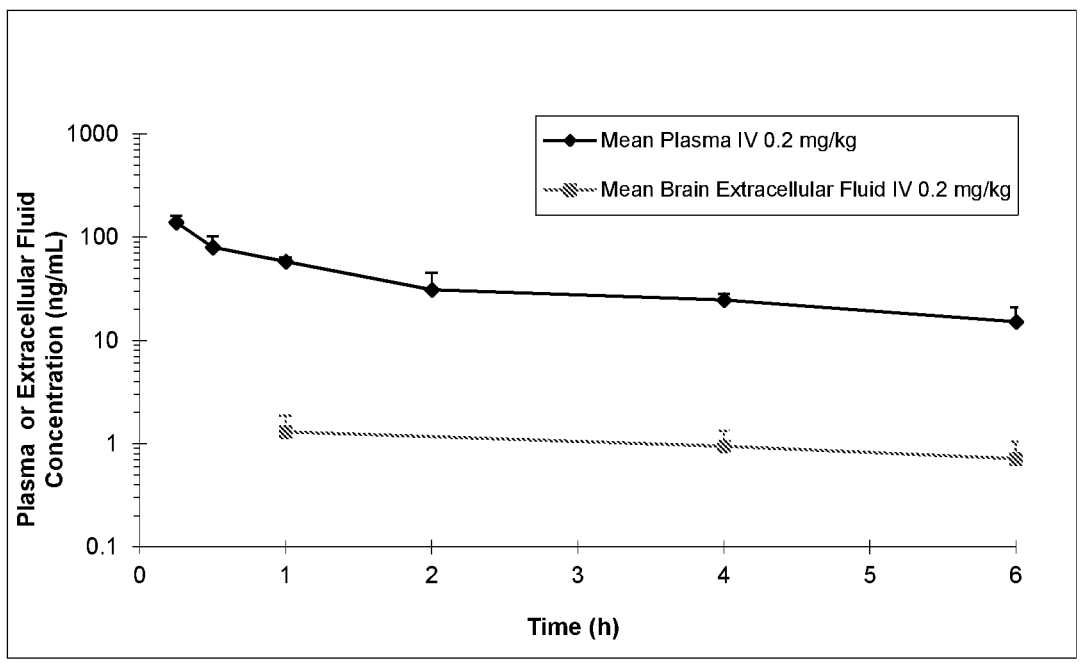
FIG. 1B shows plasma and brain extracellular fluid concentration-time profiles of MRS4322 in neonatal pigs following intravenous administration.
Figure 16:
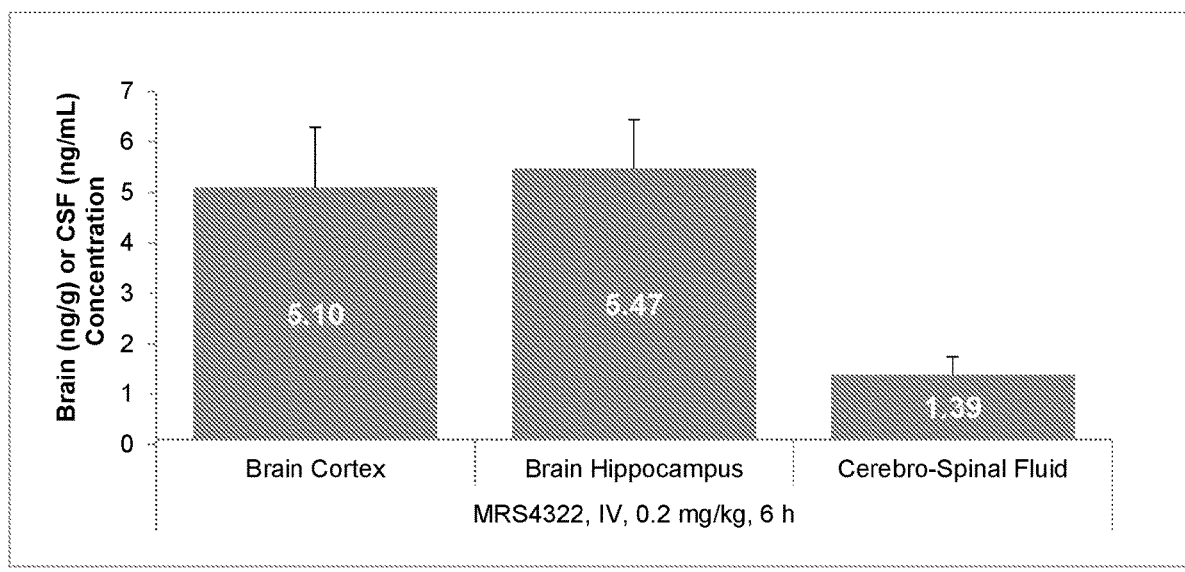
FIG. 16 shows brain and cerebrospinal fluid concentration-time profiles of MRS4322 in neonatal pigs following intravenous administration. Following intravenous administration to neonatal pigs, MRS4322 concentrations were detectable in plasma, brain, brain extracellular fluid and cerebrospinal fluid samples.

Following intraperitoneal administration to mice, MRS4322 concentrations were detectable in both plasma and brain samples (FIG. 1A and Table 2). Note that as described in Example 11 below and shown in FIGS. 1B and 16, MRS4322 concentrations were detectable in neonatal pig plasma and brain samples. Following intravenous administration to neonatal pigs, MRS4322 concentrations were detectable in plasma, brain, brain extracellular fluid and cerebrospinal fluid samples (FIG. 1B and FIG. 16, Table 13).

TABLE 2

Plasma and Brain Concentrations of MRS4322 in Mice Following Intraperitoneal Administration

| Group | Matrix | Test Article | Dose (mg/kg) | Time (h) | A | B | C | Mean | SD | N |
|---|---|---|---|---|---|---|---|---|---|---|
| | | | | | Plasma Concentration (ng/mL) by Subject | | | | | |
| 1 | Plasma | MRS4322 | 0.16 | 0 | BLQ | BLQ | BLQ | BLQ | — | 0 |
| | | | | 0.083 | 40.2 | 42.5 | 65.8 | 49.5 | 14.2 | 3 |
| | | | | 0.25 | 37.5 | 41.6 | 46.3 | 41.8 | 4.40 | 3 |
| | | | | 0.5 | 14.8 | 26.8 | 21.6 | 21.1 | 6.00 | 3 |
| | | | | 1 | 7.35 | 4.23 | 85.0* | 5.79 | NA | 2 |
| | | | | 2 | 0.539† | 0.638† | 1.15† | 0.776 | 0.328 | 3 |
| | | | | 8 | BLQ | BLQ | BLQ | BLQ | — | 0 |
| | | | | | Brain Concentration (ng/g) by Subject | | | | | |
| 1 | Brain | MRS4322 | 0.16 | 0 | BLQ | BLQ | BLQ | BLQ | — | 0 |
| | | | | 0.083 | 2.04† | 2.18† | 2.55† | 2.11 | 0.100 | 3 |
| | | | | 0.25 | 3.08† | 3.03† | 3.43† | 3.06 | 0.0400 | 3 |

TABLE 2-continued

Plasma and Brain Concentrations of MRS4322 in
Mice Following Intraperitoneal Administration

| Group | Matrix | Test Article | Dose (mg/kg) | Time (h) | A | B | C | Mean | SD | N |
|---|---|---|---|---|---|---|---|---|---|---|
| | | | | 0.5 | 1.77† | 3.00† | 1.81† | 2.39 | 0.870 | 3 |
| | | | | 1 | BLQ | BLQ | BLQ | BLQ | — | 0 |
| | | | | 2 | BLQ | BLQ | BLQ | BLQ | — | 0 |
| | | | | 8 | BLQ | BLQ | BLQ | BLQ | — | 0 |

BLQ = Below the Lower Limit of Quantitation (2.40 ng/mL for plasma, 9.64 ng/g for Brain due to 4x dilution)
*Animal F at 1 hour value of 85.0 was considered an outlier and was excluded from summary statistics
†Calculated concentrations were <LLOQ. Values reported are extrapolated Plasma concentrations allowed initial estimates of $T_{max}$, $C_{max}$, half-life and AUC (Table 3).

TABLE 3

Plasma Pharmacokinetics of MRS4322 in Mice Following Intraperitoneal Administration

| Group | Matrix | Analyte | Dose (mg/kg) | Animal ID | $C_{max}$ (ng/mL) | $T_{max}$ (hr) | $AUC_{last}$ (hr*ng/mL) | $AUC_{INF}$ (hr*ng/mL) | Half-life (hr) |
|---|---|---|---|---|---|---|---|---|---|
| 1 | Plasma | MRS4322 | 0.16 | A | 40.2 | 0.083 | 24.2 | 24.4 | 0.306 |
| | | | | B | 42.5 | 0.083 | 27.5 | 27.8 | 0.288 |
| | | | | C | 65.8 | 0.083 | 37.6 | 38.2 | 0.337 |
| | | | | N | 3 | 3 | 3 | 3 | 3 |
| | | | | Mean | 49.5 | 0.083 | 29.8 | 30.1 | 0.310 |
| | | | | SD | 14.2 | 0.000 | 7.01 | 7.19 | 0.0247 |
| | | | | CV % | 28.6 | 0.0 | 23.5 | 23.8 | 8.0 |

Note:
BLQ values were converted to zero, extrapolated values were included, and Animal F at 1 hour was excluded for PK analyses Although brain concentrations were detectable, data was insufficient for estimation of half-life or other pharmacokinetic parameters other than Cmax and Tmax. However, based on the available plasma and brain data, it was estimated that the brain/plasma ratio of total drug was approximately 0.06 based on mean Cmax concentrations in plasma and brain.

These results confirm that circulating plasma concentrations of MRS4322 are detectable following intraperitoneal administration to mice under the dosing conditions used in models of photothrombosis and traumatic brain injury, and that MRS4322 distributes to the brain under these dosing conditions.

Example 2: Pharmacokinetics of MRS4322 Following Intraperitoneal Administration of MRS2365 to Mice Purpose This study was designed to determine the plasma and brain concentrations of MRS4322 following intraperitoneal administration of the $P2Y_1$ agonist MRS2365 at a dose used in mouse photothrombosis and traumatic brain injury models.

Methods

Chemicals: MRS4322 was obtained courtesy Dr. Ken Jacobson of the National Institute of Diabetes, Digestive and Kidney Diseases (Bethesda, MD). MRS2365 was obtained from Tocris Biosciences (Bristol, UK). Analytical-grade tolbutamide was obtained from commercial supplies at Seventh Wave Laboratories (Maryland Heights, MO). All other chemicals were obtained from Sigma-Aldrich (St. Louis, MO).

Animals: Female C576BL/6J mice weighing approximately 0.02 Kg were used for this study, supplied by the University of Texas Health Sciences Center (San Antonio, TX). All studies were conducted under approved University of Texas Health Sciences Center IACUC protocols.

Drug Administration: MRS2365 was solubilized in phosphate-buffered saline and then diluted in phosphate-buffered saline to prepare dosing solution. Final dosing solution concentration of MRS2365 was 100 μM. A 100 μL volume of dosing solution was administered intraperitoneally to each mouse per 20 gram body weight; MRS2365 was administered intraperitoneally at 0.5 μmol/kg or 0.24 mg/kg. Three mice were administered MRS2365 for each sampling timepoint.

Tissue Sampling: Blood and brain samples were obtained at 0, 0.083, 0.25, 0.5, 1, 2 and 8 hours post-dose. At each timepoint, mice (3/timepoint) were euthanized in a carbon monoxide chamber. Whole blood was obtained by cardiac puncture into Microtainer tubes containing heparin and immediately centrifuged for preparation of plasma; plasma was stored at −80° C. At each timepoint, whole brain samples were obtained by decapitation, rinsed in ice-cold phosphate-buffered saline and weighed. Brain samples were then immediately flash-frozen in liquid nitrogen and stored at −80° C.

Bioanalysis: Previous studies had demonstrated that no detectable circulating and brain concentrations of MRS2365 were observed following intraperitoneal or intravenous administration, so this study focused only on the detection and quantitation of its metabolite MRS4322. Plasma and brain concentrations of MRS4322 were determined by LC-MS/MS utilizing tolbutamide as an internal standard. The following table outlines the LC and MS/MS conditions employed:

TABLE 4

Bioanalytical Methods for MRS4322 Plasma and
Brain Concentration Determinations
Bioanalytical Methods

| System Components | | |
|---|---|---|
| Module | Manufacturer | Model |
| HPLC | Shimadzu | Prominence LC-20AD Binary Pumps |
| Autosampler | Leap | Prominence Sil-30AC |
| Mass Spectrometer | AB Sciex | 4000 Qtrap |

| HPLC Method | |
|---|---|
| Column | Phenomenex Kinetex C18 (2.1 × 50 mm, 2.6 μm) |
| Elution | Gradient, 0.4 mL/min<br>Mobile Phase A: 0.1% Formic Acid<br>Mobile Phase B: 0.1% Formic Acid in Acetonitrile |

MS Detection and Calibration for MRS4322 in Mouse Plasma

Peak Name: Tolbutamide
Use as Internal Standard
Q1/Q3 Masses:
271.20/155.20 Da
Peak Name: MRS4322
Internal Standard:
Tolbutamide
Q1/Q3 Masses:
324.10/182.00 Da

| Fit | Linear | Weighting | 1/x |
|---|---|---|---|
| Intercept | 0.000704 | | |
| Slope | 0.00151 | | |
| Correlation coefficient | 0.9998 | | |
| Use Area | | | |

TABLE 4-continued

Bioanalytical Methods for MRS4322 Plasma and
Brain Concentration Determinations
Bioanalytical Methods MS Detection and Calibration for MRS4322 in Mouse Brain Homogenate Peak Name: Tolbutamide
Use as Internal Standard
Q1/Q3 Masses:
271.20/155.20 Da
Peak Name: MRS4322
Internal Standard:
Tolbutamide
Q1/Q3 Masses:
324.10/182.00 Da

| Fit | Linear | Weighting | 1/x |
|---|---|---|---|
| Intercept | 0.000209 | | |
| Slope | 0.000864 | | |
| Correlation coefficient | 1.00 | | |
| Use Area | | | |

For each tissue matrix, standard curves were created and LLOQ/ULOQ concentrations determined. The calibration range for the MRS4322 plasma concentration standard curve was 2.26-241 ng/mL. The calibration range for MRS4322 brain concentrations was 2.35-242 ng/mL.

For bioanalysis of brain concentrations of MRS4322, brain samples were homogenized in ice-cold phosphate-buffered saline in a 4× dilution. Aliquots of the resulting diluted brain homogenate were treated with acetonitrile and analyzed by LC-MS/MS. Because of the 4× homogenate dilution, the calibration range of the MRS4322 brain standard curve was translated to 9.40-968 ng/gm. In several samples, MRS4322 were detectable but fell below the brain LLOQ of 9.40 ng/gm but were above background; in these cases the final reported brain concentration was extrapolated based on MS peak heights.

Results

Figure 2:
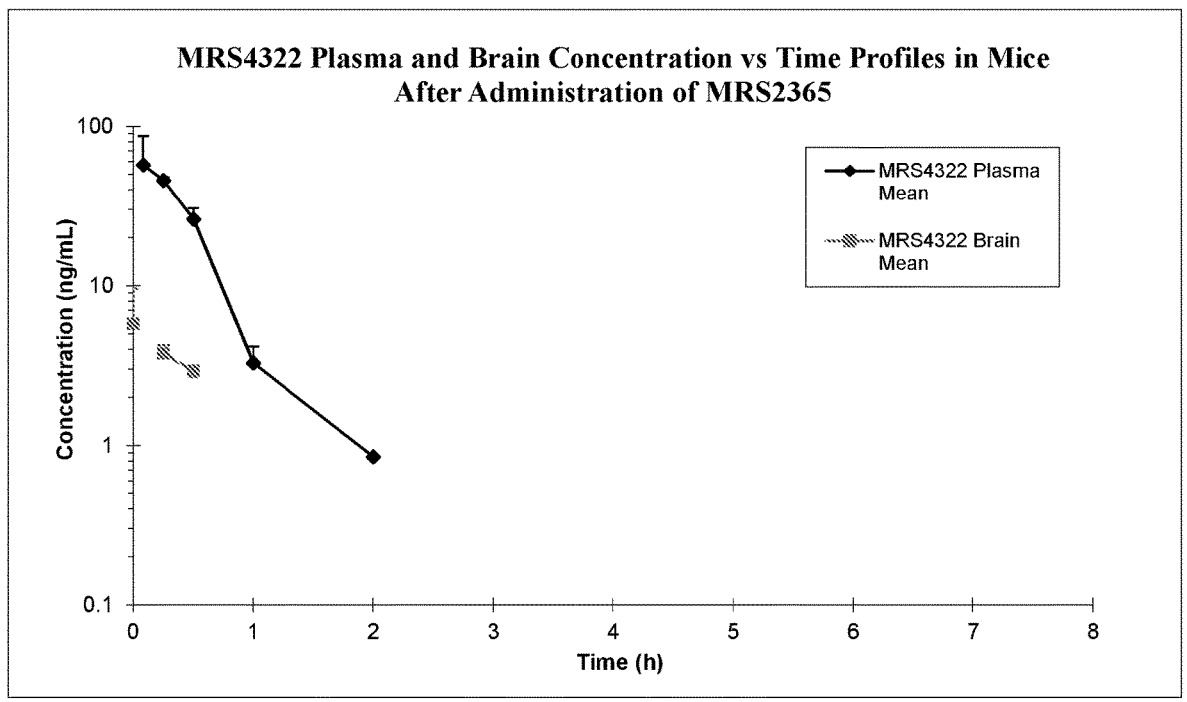
FIG. 2 shows plasma and brain concentration-time profiles of MRS4322 in mice following intraperitoneal administration of MRS2365.

Following intraperitoneal administration of MRS2365 to mice, MRS4322 concentrations were detectable in both plasma and brain samples (FIG. 2 and Table 5).

TABLE 5

Plasma and Brain Concentrations of MRS4322 in Mice
Following Intraperitoneal Administration of MRS2365

| Group | Matrix | Test Article | Dose (mg/kg) | Time (h) | Plasma Concentration (ng/mL) by Subject | | | | | |
|---|---|---|---|---|---|---|---|---|---|---|
| | | | | | A | B | C | Mean | SD | N |
| 1 | Plasma | MRS4322 | 0.24 | 0 | BLQ | BLQ | BLQ | BLQ | — | 0 |
| | | MRS2365 | 0.083 | | 24.5 | 64.1 | 82.8 | 57.1 | 29.8 | 3 |
| | | | 0.25 | | 46.5 | 43.2 | 47.4 | 45.7 | 2.20 | 3 |
| | | | 0.5 | | 22.3 | 25.1 | 31.0 | 26.1 | 4.40 | 3 |
| | | | 1 | | 2.30 | 4.02 | 3.53 | 3.28 | 0.890 | 3 |
| | | | 2 | | BLQ | 1.02* | 0.680* | 0.850 | NA | 2 |
| | | | 8 | | BLQ | BLQ | BLQ | BLQ | — | 0 |

| Group | Matrix | Test Article | Dose | Time (h) | Brain Concentration (ng/g) by Subject | | | | | |
|---|---|---|---|---|---|---|---|---|---|---|
| | | | | | A | B | C | Mean | SD | N |
| 1 | Brain[a] | MRS4322 | 0.24 | 0 | 2.76* | 10.0 | 4.61* | 5.79 | 3.76 | 3 |
| | | MRS2365 | | 0.083 | BLQ | BLQ | BLQ | BLQ | — | 0 |
| | | | | 0.25 | 3.92* | 3.26* | 4.16* | 3.78 | 0.470 | 3 |
| | | | | 0.5 | 3.19* | 2.80* | 2.70* | 2.90 | 0.260 | 3 |
| | | | | 1 | BLQ | BLQ | BLQ | BLQ | — | 0 |

TABLE 5-continued

Plasma and Brain Concentrations of MRS4322 in Mice
Following Intraperitoneal Administration of MRS2365

| | 2 | BLQ | BLQ | BLQ | BLQ | — | 0 |
| | 8 | BLQ | BLQ | BLQ | BLQ | — | 0 |

BLQ = Below the Lower Limit of Quantitation (2.26 ng/mL for plasma; 9.40 ng/g for Brain due to 4-fold dilution)
*Projected values; these values were below the limit of quantitation
$^a$It appears possible that the 0 and 0.083 samples were mislabeled upon receipt Plasma concentrations allowed initial estimates of Tmax, Cmax, half-life and AUC (Table 6).

TABLE 6

Plasma Pharmacokinetics of MRS4322 in Mice Following Intraperitoneal Administration of MRS2365

| Group | Matrix | Analyte | Dose (mg/kg) | Animal ID | $C_{max}$ (ng/mL) | $T_{max}$ (hr) | $AUC_{last}$ (hr*ng/mL) | $AUC_{INF}$ (hr*ng/mL) | Half-life (hr) |
|---|---|---|---|---|---|---|---|---|---|
| 1 | Plasma | MRS4322 | 0.24 | $A^a$ | 46.5 | 0.25 | 21.7 | 22.3 | 0.17 |
| | | MRS2365 | | B | 64.1 | 0.08 | 30.0 | 30.5 | 0.34 |
| | | | | C | 82.8 | 0.08 | 34.8 | 35.1 | 0.28 |
| | | | | N | 3 | 3 | 3 | 3 | 3 |
| | | | | Mean | 64.5 | 0.14 | 28.8 | 29.3 | 0.27 |
| | | | | SD | 18.2 | 0.10 | 6.65 | 6.51 | 0.09 |
| | | | | CV % | 28.2 | 69.5 | 23.1 | 22.2 | 33.1 |

BLQ values were converted to zero; extrapolated values were included for PK analyses.

Although brain concentrations were detectable, data was insufficient for estimation of half-life or other pharmacokinetic parameters other than Cmax and Tmax. However, based on the available plasma and brain data, it was estimated that the brain/plasma ratio of total drug was approximately 0.10 based on mean Cmax concentrations in plasma and brain.

These results confirm that circulating plasma concentrations of MRS4322 are detectable following intraperitoneal administration of the P2Y$_1$ agonist MRS2365 to mice under the dosing conditions used in models of photothrombosis and traumatic brain injury, and that MRS4322 distributes to the brain under these dosing conditions.

MRS4322 plasma and brain concentrations were determined in two different studies, following intraperitoneal administration of MRS4322 itself (see Example 1) and following intraperitoneal administration of the P2Y$_1$ agonist MRS2365. In both of these studies, MRS4322 or MRS2365 were administered at equimolar doses of 0.5 μmol/kg. Comparing the results of both studies, the observed plasma concentrations of MRS4322 were virtually identical and brain concentrations of MRS4322 were very similar (compare FIGS. 1 and 2). There was no statistically significant difference in the half-life and AUC values for MRS4322 following administration of equimolar doses of MRS4322 or MRS2365. These data indicate that following intraperitoneal administration to mice, MRS2365 is rapidly and completely metabolized to MRS4322, resulting in MRS4322 plasma and brain pharmacokinetics very similar to those following intraperitoneal administration of MRS4322 itself.

Example 3: Plasma and Brain Binding of MRS4322 in Mice

Purpose

This study was designed to determine the plasma and brain free fraction of MRS4322 in mice and compare free fractions to those of a prototypical adenosine A$_3$ receptor agonist, MRS5698. MRS5698 has the following chemical structure:

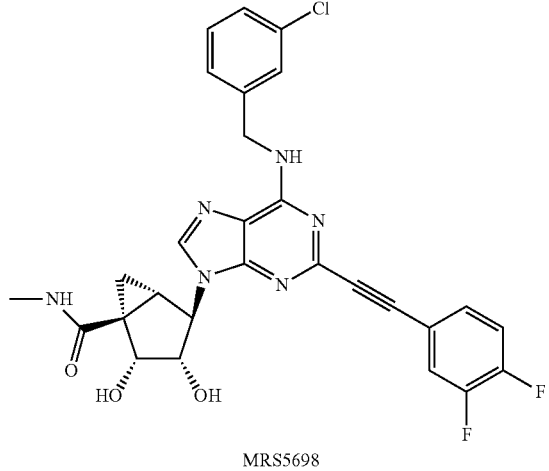 [SMILES: CNC(=O)[C@@]12C[C@@H]1[C@@H](n1cnc3c(NCc4cccc(Cl)c4)nc(C#Cc4ccc(F)c(F)c4)nc31)[C@H](O)[C@@H]2O]

MRS5698

Methods

Chemicals: MRS4322 was obtained courtesy Dr. Ken Jacobson of the National Institute of Diabetes, Digestive and Kidney Diseases (Bethesda, MD). MRS5698 was acquired from Tocris Biosciences (Bristol, UK). Analytical-grade sulfamethoxazole and warfarin were obtained from commercial supplies at Seventh Wave Laboratories (Maryland Heights, MO). All other chemicals were obtained from Sigma-Aldrich (St. Louis, MO).

Animals and Tissue Preparation: Plasma from male CD-1 mice was obtained from BioreclamationIVT (Westbury, NY) and stored at −80° C. until use. Male CD-1 mouse brains were obtained from BioreclamationIVT (Westbury, NY).

Plasma ultrafiltrate blank samples were prepared by thawing frozen plasma and then pre-warming plasma in a humidified 5% CO$_2$ chamber at 37° C. for 60 minutes. Aliquots of 800 μL were transferred to Centrifree Centrifugal Filters (Ultracel regenerated cellulose (NMWL 30,000 amu) Lot R5JA31736) and centrifuged at 2900 RPM at 37° C. for 10 minutes; plasma water filtrates were collected and used in preparation of standards, blanks and QC standards.

Brains were weighed and homogenized with 1:9 phosphate-buffered saline, pH 7.4 using an Omni tissue homogenizer. Brains from four mice were homogenized, pooled and mixed to form one sample.

Plasma Binding Determination: MRS4322, MRS5698, sulfamethaxazole and warfarin were solubilized in DMSO and then diluted in 1:1 acetonitrile:water to prepare 100 μM dialysis stock solutions. Sulfamethaxazole and warfarin were utilized as study standards with known plasma binding values. Plasma samples were pre-warmed for 60 minutes in a humidified, 5% $CO_2$ incubator maintained at 37° C. Three mL aliquots of pre-warmed plasma were each spiked with MRS4322, MRS5698, sulfamethaxazole or warfarin using 100 μM stock solutions for each compound resulting in final test concentrations of 1 μM. Spiked plasma samples were incubated on a rotary mixer in a humidified 5% $CO_2$ chamber at 37° C. for a minimum of 60 minutes. After 60 minutes, three 800 μL aliquots of each sample were added to Centrifree centrifugal filters. The filters were subjected to centrifugation at 2900 rpm for 10 minutes at 37° C. Three 100 μL aliquots of residual plasma were collected along with ultrafiltrate for bioanalysis.

Brain Binding Determination: MRS4322, MRS5698, sulfamethoxazole and warfarin were solubilized in DMSO and diluted in 1:1 acetonitrile:water to prepare 100 μM dialysis stock solutions. Pooled homogenized brains were pre-warmed for 60 minutes in a humidified, 5% $CO_2$ incubator maintained at 37° C. Three mL aliquots of brain homogenate were each spiked with MRS4322, MRS5698, sulfamethaxazole or warfarin using the 100 μM stock solutions for each compound resulting in final spiked concentrations of 1 μM. Spiked pooled brain homogenates were placed on a Nutator mixer in a humidified, 5% $CO_2$ incubator at 37° C. for 60 minutes. After 60 minutes, three 800 μL aliquots of each sample were added to Centrifree centrifugal filters. The filters were subjected to centrifugation at 2900 rpm for 10 minutes at 37° C. Aliquots of residual brain homogenate and ultrafiltrate were collected for bioanalysis.

Bioanalysis

Plasma and brain concentrations of MRS4322 and MRS5698 in spiked plasma, brain homogenates and associated ultrafiltrates were determined by LC-MS/MS utilizing tolbutamide as an internal standard. Associated concentrations of sulfamethaxazole and warfarin were also determined by LC-MS/MS using standard conditions (data not shown). The following tables outline the LC and MS/MS conditions employed (Tables 7 and 8). Bioanalytical methods were identical for all matrices; standard curve statistics (e.g. Fit, Intercept, Slope, Correlation Coefficient) were determined for each matrix but were not significantly different and thus are not shown for each matrix.

TABLE 7

Bioanalytical Methods for MRS4322 for Determination of Plasma, Brain Homogenate, Plasma Ultrafiltrate and Brain Homogenate Ultrafiltrate Concentrations
Bioanalysis of Plasma, Brain Homogenates, Plasma Ultrafiltrate and Brain Homogenate Ultrafiltrate Samples

| System Components | | |
|---|---|---|
| Module | Manufacturer | Model |
| HPLC | Shimadzu | Prominence LC20AD Binary Pumps |
| Autosampler | CTC Leap | HTC PAL |
| Mass Spectrometer | AB Sciex | API 4000 |

| HPLC Method | |
|---|---|
| Column | Phenomenex Kinetex C18 (2.1 × 50 mm, 2.6 μm) |
| Elution | Gradient, 0.4 mL/min Mobile Phase A: 0.1% Formic acid in Water Mobile Phase B: 0.1% Formic acid in Acetontrile |

| Mass Spectrometer Conditions for MRS4322 | | |
|---|---|---|
| Peak Name: MRS4322 Q1/Q3 Masses: 324.10/182.00 Da Peak Name: Tolbutamide Q1/Q3 Masses: 271.20/155.20 Da | | |
| Fit | Linear | Weighting 1/x |
| Intercept | 0.0181 | |
| Slope | 0.00192 | |
| Correlation coefficient | 0.9988 | |

TABLE 8

Bioanalytical Methods for MRS5698 for Determination of Plasma, Brain Homogenate, Plasma Ultrafiltrate and Brain Homogenate Ultrafiltrate Concentrations

| System Components | | |
|---|---|---|
| Module | Manufacturer | Model |
| HPLC | Shimadzu | Prominence LC20AD Binary Pumps |
| Autosampler | CTC Leap | HTC PAL |
| Mass Spectrometer | AB Sciex | API 4000 |

| HPLC Method | |
|---|---|
| Column | Phenomenex Kinetex C18 (2.1 × 50 mm, 2.6 μm) |
| Elution | Gradient, 0.4 mL/min Mobile Phase A: 0.1% Formic acid in Water Mobile Phase B: 0.1% Formic acid in Acetontrile |

| Mass Spectrometer Conditions for MRS5698 |
|---|
| Peak Name: MRS5698 Q1/Q3 Masses: 565.10/395.90 Da Peak Name: Tolbutamide Q1/Q3 Masses: 271.20/155.20 Da |

TABLE 8-continued

Bioanalytical Methods for MRS5698 for Determination of Plasma, Brain Homogenate, Plasma Ultrafiltrate and Brain Homogenate Ultrafiltrate Concentrations

| Fit | Linear | Weighting | 1/x |
|---|---|---|---|
| Intercept | 0.107 | | |
| Slope | 0.00786 | | |
| Correlation coefficient | 0.9986 | | |

For each tissue matrix, standard curves were created and LLOQ/ULOQ concentrations determined. The calibration range for the MRS4322 and MRS5698 plasma concentration standard curves was 400-1200 nM. The calibration range for MRS4322 and MRS5698 plasma ultrafiltrate standard curves was 100-1200 nM. The calibration range for MRS4322 brain homogenate and brain homogenate ultrafiltrate standard curves were 400-1200 nM and 100-1200 nM, respectively. The calibration range for MRS5698 brain homogenate and brain homogenate ultrafiltrate standard curves were 400-1200 nM and 1-500 nM, respectively.
Results Plasma binding and free fraction were determined for MRS4322 and MRS5698 utilizing plasma ultrafiltration. Plasma binding was 25.8% for MRS4322; associated free fraction was 0.742 (Table 9).

MRS5698 concentrations were not detected in the plasma ultrafiltrate; MRS5698 was completely recovered in the residual spiked plasma samples obtained from the donor side of the Centrifree devices (data not shown). This indicates that the low MRS5698 ultrafiltrate concentrations were not due to low analytical recovery of the compound. Overall, these data are consistent with the high protein binding (99.88%) of MRS5698 in mouse plasma and tissue reported in the literature (Tosh, D. K. et al. Purinergic Signalling (2015) 11:371-387). Binding of the study standards sulfamethaxazole and warfarin were consistent with literature values.

TABLE 9

Fraction Unbound and Binding of MRS4322 and MRS5698 in Mouse Plasma

| | Fraction Unbound | | % Bound | | |
|---|---|---|---|---|---|
| Substrate | Mean | SD | Mean | SD | N |
| MRS4322 | 0.742 | 0.065 | 25.8 | 6.5 | 3 |
| MRS5698 | * | * | * | * | 3 |
| Sulfamethoxazole | 0.345 | 0.027 | 65.5 | 2.7 | 3 |
| Warfarin | 0.0485 | 0.0031 | 95.1 | 0.3 | 3 |

* Plasma ultrafiltrate concentrations of MRS5698 were BLQ

Brain binding and free fraction were determined for MRS4322 and MRS5698 utilizing brain homogenate ultrafiltration. Brain binding was 87% for MRS4322; associated free fraction was 0.13 (Table 10).

MRS5698 concentrations were not detected in the brain homogenate ultrafiltrate. For estimation purposes, the MRS5698 brain homogenate ultrafiltrate LLOQ was utilized to calculate a brain binding value. The resulting brain binding value was 99.99%. Overall, these data are consistent with the high protein binding (99.88%) of MRS5698 in mouse plasma and tissue reported in the literature (Tosh, D. K. et al. Purinergic Signalling (2015) 11:371-387). Binding of the study standards sulfamethaxazole and warfarin were consistent with literature values.

TABLE 10

Fraction Unbound and Binding of MRS4322 and MRS5698 in Mouse Brain Homogenates

| | | Fraction Unbound | | % Bound | | |
|---|---|---|---|---|---|---|
| Assay | Substrate | Mean | SD | Mean | SD | N |
| 1 | MRS4322 | 0.130 | 0.010 | 87.0 | 1.0 | 3 |
| | MRS5698 | <0.000122* | — | >99.99* | — | 3 |
| | Sulfamethoxazole | 0.431 | 0.049 | 56.9 | 4.9 | 3 |
| | Warfarin | 0.208 | 0.038 | 79.2 | 3.8 | 3 |

*MRS5698 was not detected in ultrafiltrate; assay LLOQ was utilized to calculate an estimated binding value Overall, these data indicate that MRS4322 has a substantially higher free fraction and lower protein binding than the adenosine $A_3$ agonist MRS5698 in both plasma and brain. These data indicate that for a given total plasma or brain concentration, substantially higher concentrations of MRS4322 would be available to interact with effector sites than would be available for MRS5698.

Example 4: In Vitro Stability and Metabolism of MRS2365 in Mouse and Human Blood and Plasma Purpose This study was designed to determine the in vitro stability and metabolic fate of the $P2Y_1$ agonist MRS2365 in mouse and human blood and plasma.
Methods Chemicals: MRS2365 was obtained from Tocris Biosciences (Bristol, UK). MRS4322 was obtained courtesy Dr. Ken Jacobson of the National Institute of Diabetes, Digestive and Kidney Diseases (Bethesda, MD). All other chemicals were obtained from Sigma-Aldrich (St. Louis, MO). Enalapril and procaine were used as plasma and blood stability standards for mouse and human, respectively.

Tissue Preparation: Plasma from male CD-1 mice and humans was obtained from BioreclamationIVT (Westbury, NY) and stored at −80° C. until use. Whole blood was obtained from male CD-1 mice and human volunteers at Seventh Wave Laboratories (Maryland Heights, MO). Plasma and blood samples were prepared using either EDTA (1 mM) or lithium heparin as anticoagulants.

Figure 3:
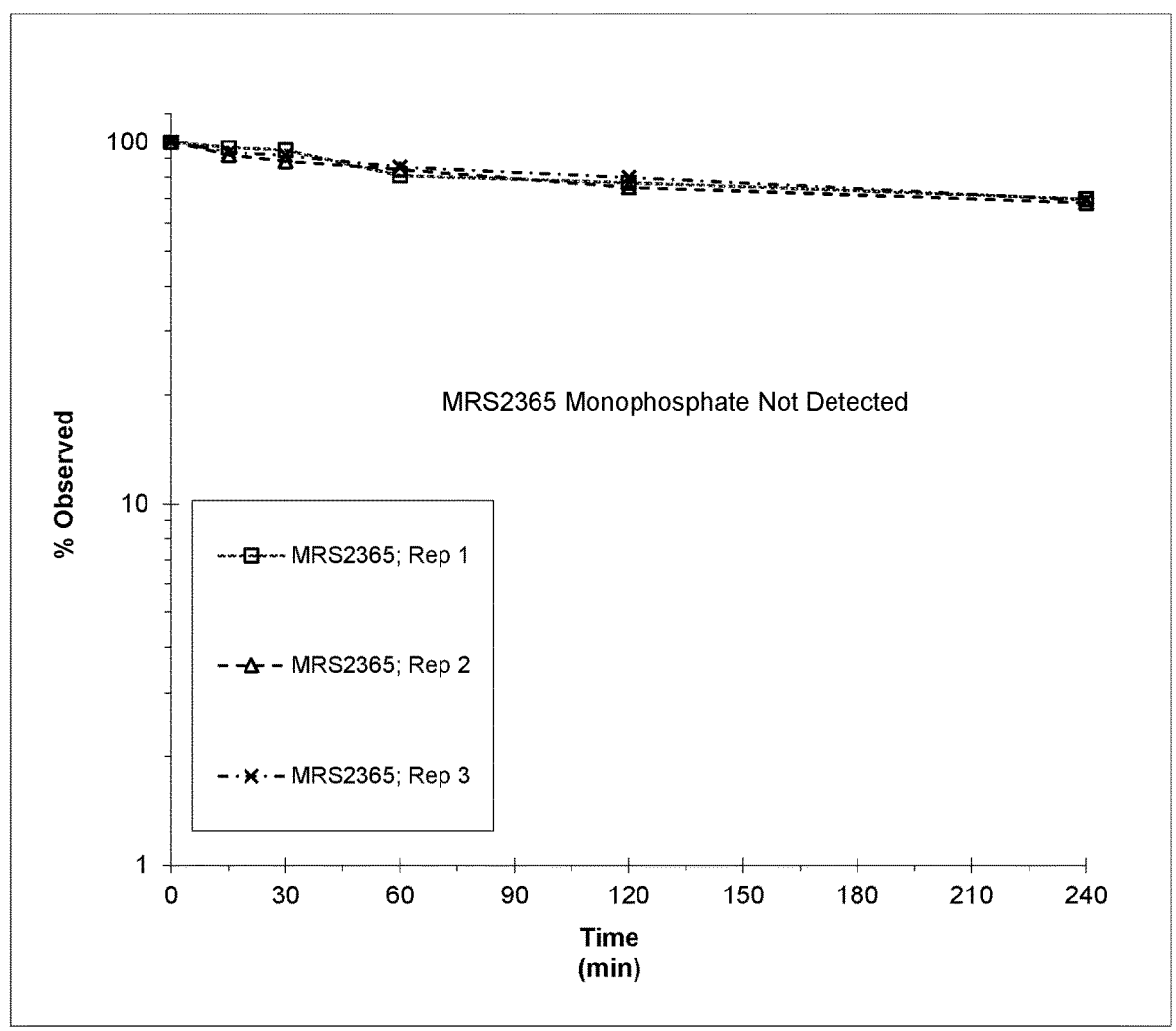
FIG. 3 shows in vitro stability of MRS2365 in EDTA-treated mouse plasma.
Figure 4:
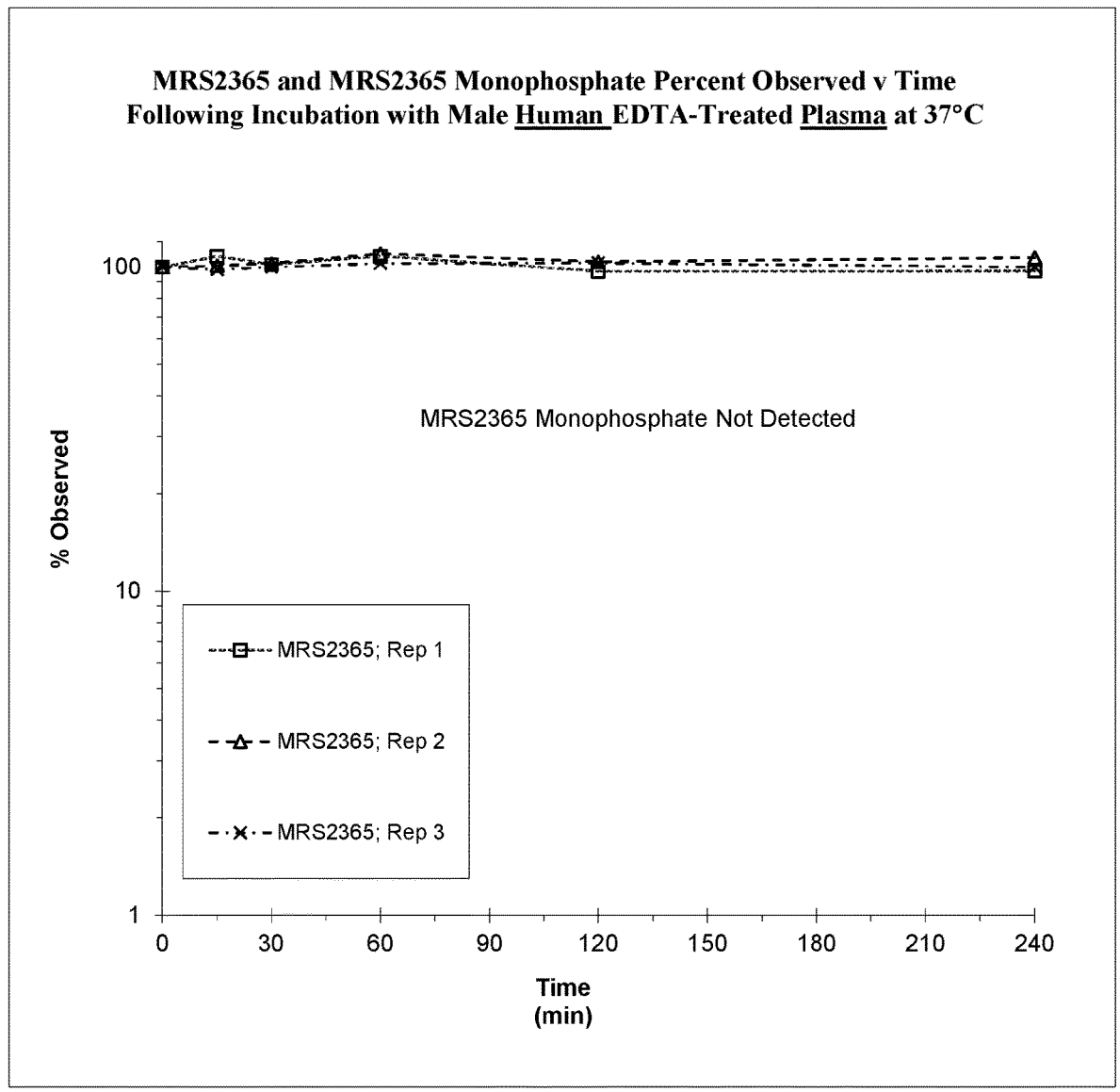
FIG. 4 shows in vitro stability of MRS2365 in EDTA-treated human plasma.
Figure 7:
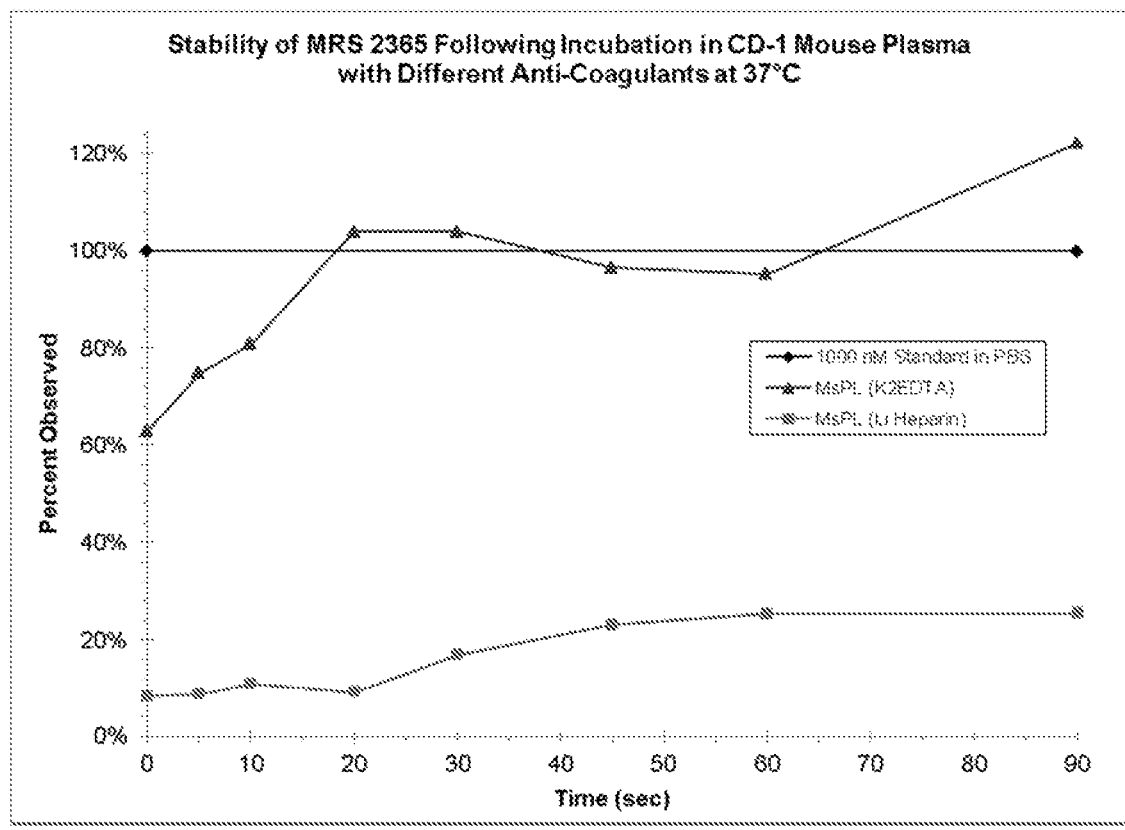
FIG. 7 shows in vitro stability of MRS2365 in EDTA- and Heparin-treated mouse plasma over a 90-second incubation period.
Figure 8:
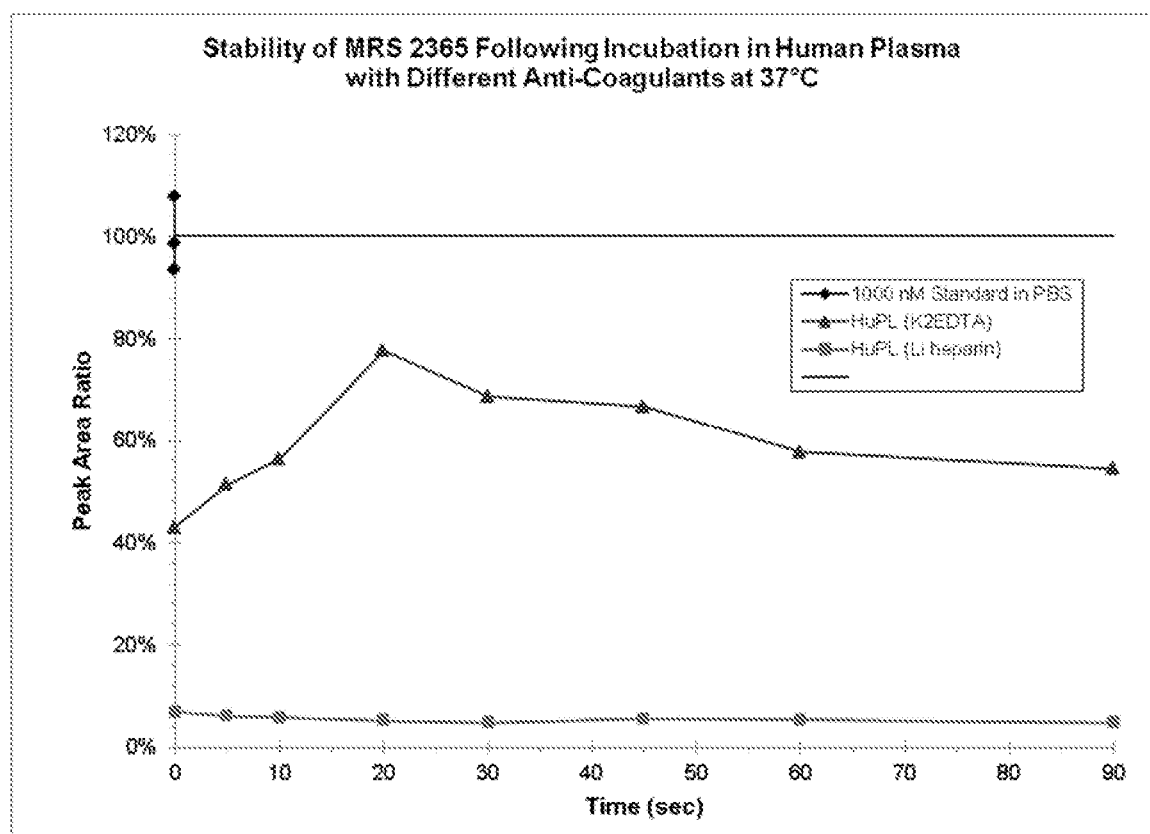
FIG. 8 shows in vitro stability of MRS2365 in EDTA- and Heparin-treated human plasma over a 90-second incubation period.
Figure 9:
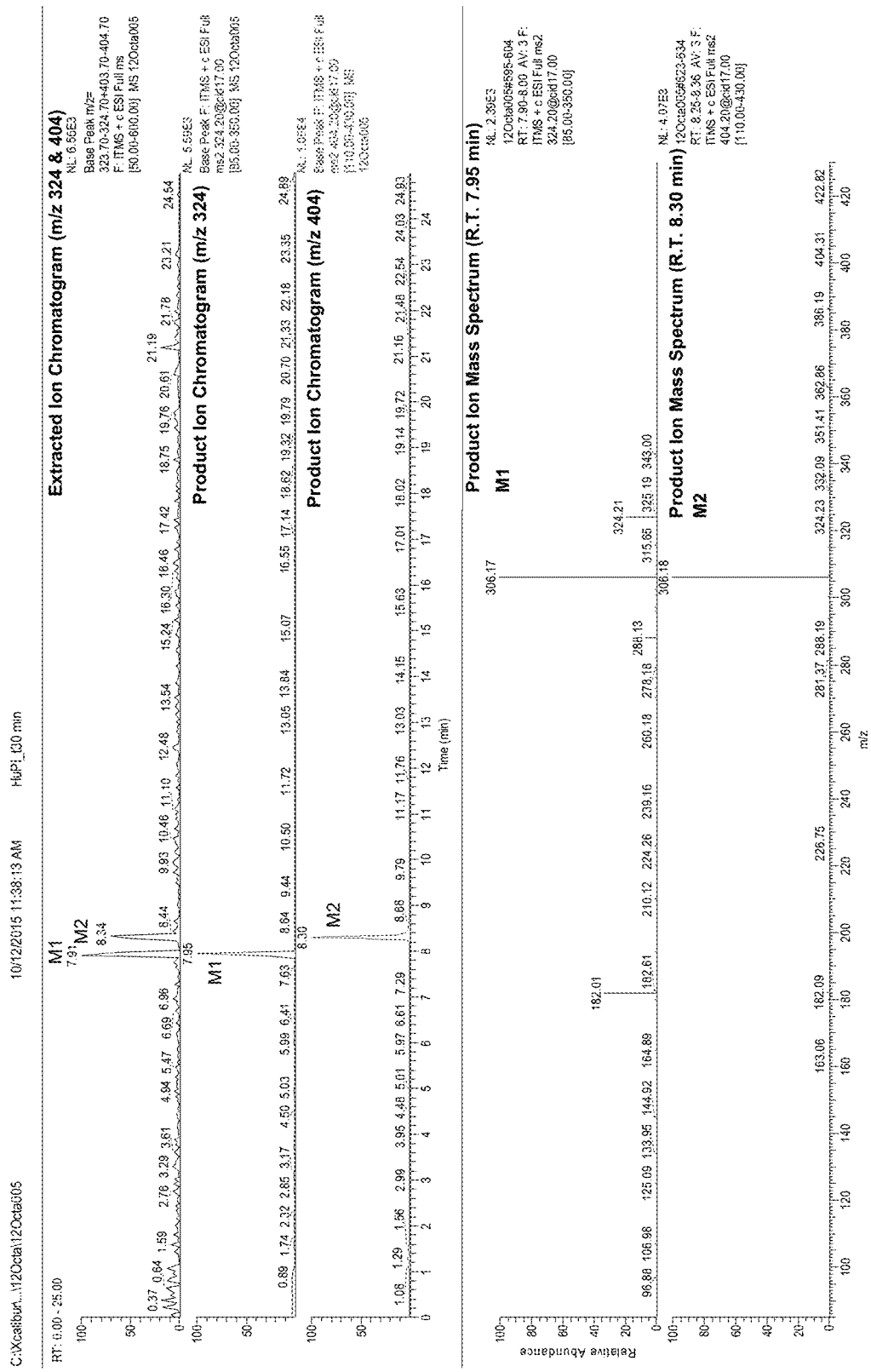
FIG. 9 shows positive-ion LC/MS-MS ion chromatograms and product ion spectra of MRS2365 metabolites in heparinized human plasma following a 30-minute incubation.

Plasma Stability Determination: MRS2365, enalapril and procaine were solubilized in phosphate-buffered saline, pH 7.4. Plasma samples (prepared from blood with either EDTA or lithium heparin as anticoagulant) were pre-warmed for 60 minutes in a humidified, 5% $CO_2$ incubator maintained at 37° C. Stability incubations were initiated with the addition of MRS2365 (1 µM final concentration). Initial assessments of stability in EDTA-generated plasma utilized incubation timepoints of 0, 10, 30, 60, 120 and 240 minutes (FIGS. 3 and 4). Subsequent studies comparing EDTA- and heparin-generated plasma utilized incubation timepoints of 0, 1, 2.5, 5, 7.5, 10 and 30 minutes (FIG. 7). Additional plasma stability incubations comparing EDTA- and heparin-generated plasma were performed using timepoints of 0, 5, 10, 20, 30, 45, 60 and 90 seconds (FIG. 8). For metabolite scouting analyses, MRS2365 was incubated in heparinized human plasma at a concentration of 100 µM for 10 or 30 minutes (FIG. 9). In all studies, plasma was immediately placed in microtainer tubes, frozen on dry ice and stored at −80° C. until analysis.

Figure 5:
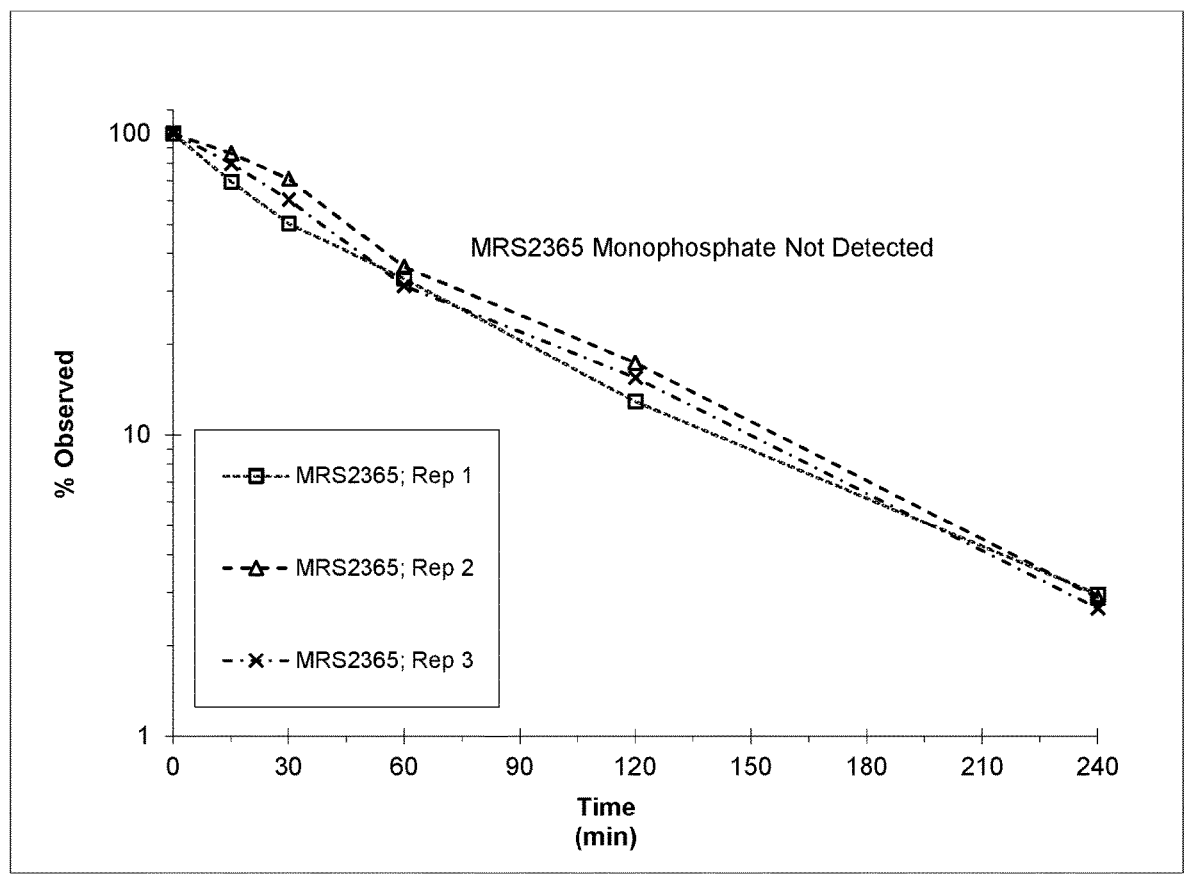
FIG. 5 shows in vitro stability of MRS2365 in EDTA-treated mouse whole blood.
Figure 6:
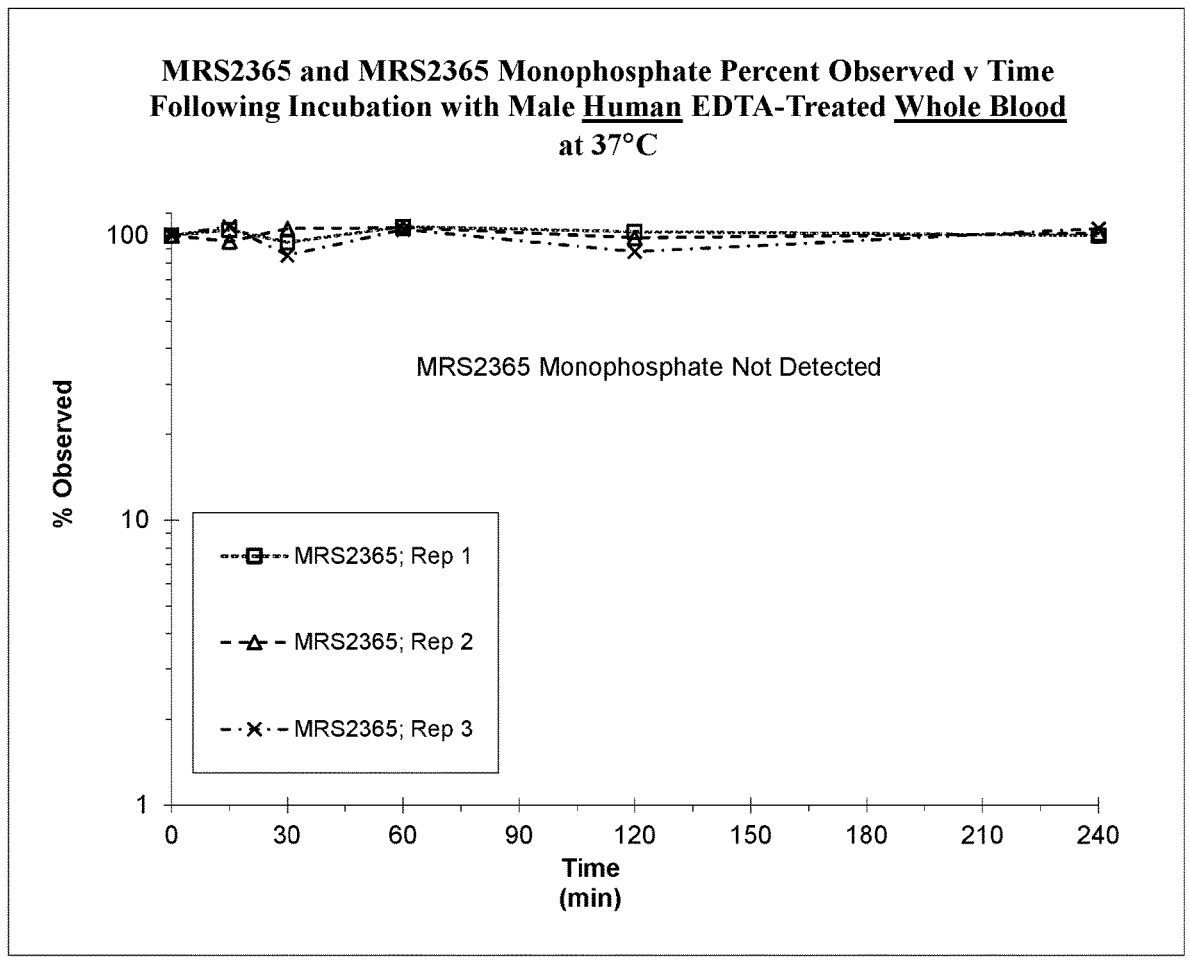
FIG. 6 shows in vitro stability of MRS2365 in EDTA-treated human whole blood.
Figure 10:
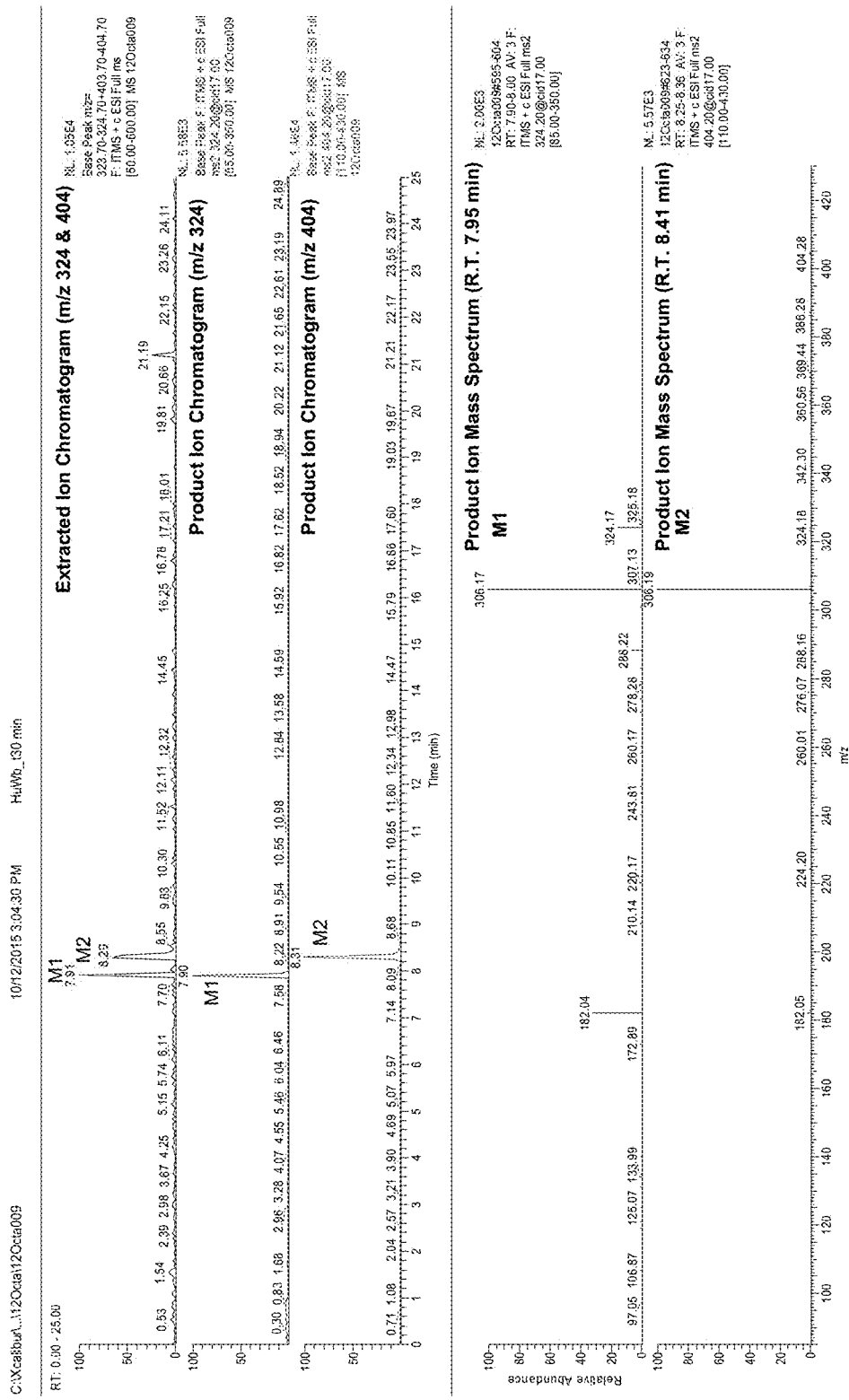
FIG. 10 shows positive-ion LC/MS-MS ion chromatograms and product ion spectra of MRS2365 metabolites in heparinized human whole blood following a 30-minute incubation.
Figure 11:
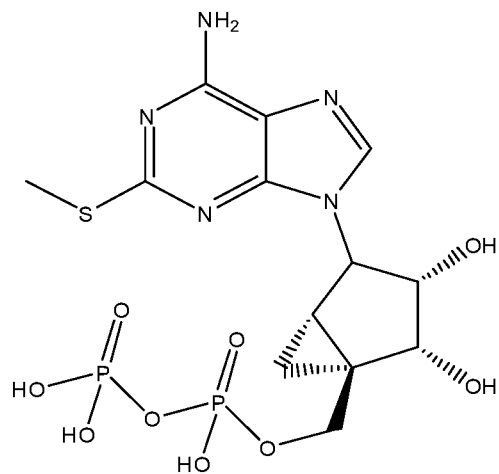
FIG. 11 shows a scheme representing metabolites of MRS2365 detected by positive- and negative-ion LC/MS-MS in heparinized human plasma and whole blood. Two metabolites of MRS2365 were observed following incubation at 100 μM in human whole blood and plasma (lithium heparin as anti-coagulant): M2, identified as the partially dephosphorylated metabolite of MRS2365 (i.e. with one phosphate group remaining, MRS2347); and M1, identified as the fully dephosphorylated metabolite of MRS2365 (i.e. MRS4322).
Figure 11:
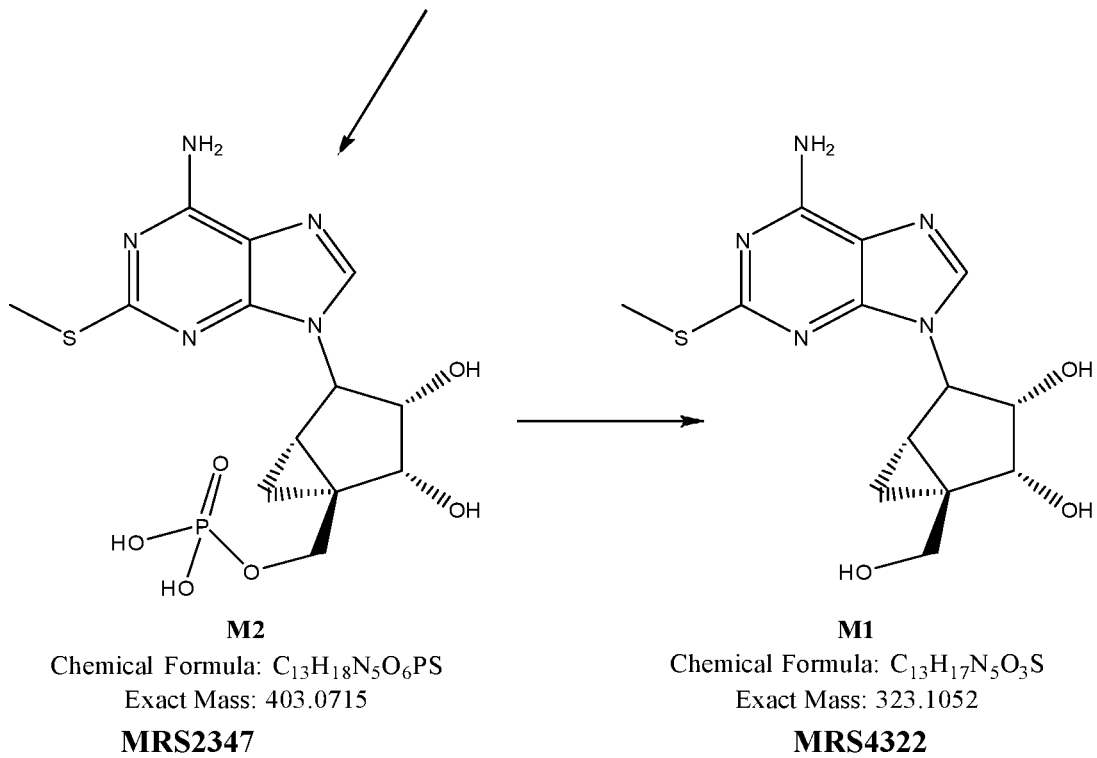

Blood Stability Determination: MRS2365, enalapril and procaine were solubilized in phosphate-buffered saline, pH 7.4. Blood samples (EDTA- or lithium heparin-treated) were pre-warmed for 60 minutes in a humidified, 5% $CO_2$ incubator maintained at 37° C. Stability incubations were initiated with the addition of MRS2365 (1 µM final concentration) (FIGS. 5 and 6). Blood sample aliquots were obtained at 0, 1, 2.5, 7.5, 10 and 30 minutes and placed in microtainer tubes. For metabolite scouting analyses, MRS2365 was incubated in heparinized human whole blood at a concentration of 100 µM for 10 or 30 minutes (FIG. 10). In all studies, plasma was immediately prepared by centrifugation at 4° C., placed in microtainer tubes, frozen on dry ice and stored at –80° C. until analysis.

Bioanalysis

Plasma and blood concentrations of MRS2365 were determined by LC-MS/MS utilizing tolbutamide as an internal standard. The following table outlines the LC and MS/MS conditions employed (Table 11). Bioanalytical methods were identical for all matrices; standard curve statistics (e.g. Fit, Intercept, Slope, Correlation Coefficient) were determined for each matrix but were not significantly different and thus are not shown for each matrix.

TABLE 11

Bioanalytical Methods for MRS2365 for
Determination of Plasma and Blood Concentrations
in In Vitro Stability Determinations
Bioanalysis Methods - Plasma and Blood

| System Components | | |
|---|---|---|
| Module | Manufacturer | Model |
| HPLC | Shimadzu | Prominence |
| Autosampler | Leap | CTC Pal |
| Mass Spectrometer | AB Sciex | API 4000 |

| HPLC Method | |
|---|---|
| Column | Luna C18 (2.1 × 50 mm, 2.6 µm) |
| Elution | Gradient, 0.4 mL/min |
| | Mobile Phase A: 2 mM Ammonium acetate, pH 7.65 |
| | Mobile Phase B: 2 mM Ammonium acetate in Acetonitrile |

MS Detection and Calibration for MRS2365 in Plasma and Blood

Peak Name: Tolbutamide
Use as Internal Standard
Q1/Q3 Masses:
269.00/170.00 Da
Peak Name: MRS2365
Internal Standard:
Tolbutamide
Q1/Q3 Masses:
482.11/384.00 Da

| Fit | Linear | Weighting | 1/(x * x) |
|---|---|---|---|
| Intercept | 0.00004 | | |
| Slope | 0.00002 | | |
| Correlation coefficient | 0.9854 | | |
| Use Area | | | |

For each tissue matrix, standard curves were created and LLOQ/ULOQ concentrations determined. The calibration range for MRS2365 plasma and blood concentration standard curves was 5-5000 ng/mL. Quality control samples were utilized at concentrations of 32, 160, 800 and 4000 ng/mL.

Plasma and blood samples were also qualitatively analyzed for MRS2365 metabolites utilizing a LC-MS/MS-based "metabolite scouting" protocol. From review of the metabolic pathways of other nucleotides (e.g. ATP, ADP), it was hypothesized that the most likely metabolites of MRS2365 would be the dephosphorylated (i.e., monophosphate) metabolite (MRS2347, mw=403.07) and/or the completely dephosphorylated riboside metabolite (MRS4322, mw=323.10). Blood and plasma samples were analyzed by both positive- and negative-ion LC/MS-MS for parent compound and metabolites as it was anticipated that the phosphorylated compounds would preferentially generate negative ions while the riboside MRS4322 would preferentially generate positive ions. In positive-ion mode, extracted ion chromatograms monitored masses in the range of 323.7-324.7 and 403.7-404.7 to scout for MRS4322 and MRS2347, respectively. Any ion peaks in these ranges were further analyzed to generate product ion spectra for these ion chromatogram peaks. In negative-ion mode, extracted ion chromatograms monitored masses in the range of 321.70-322.70, 401.70-402.70 and 481.70-482.70 to scout for MRS4322, MRS2347 and MRS2365, respectively; peaks were further analyzed to generate product ion spectra. Because authentic standards of MRS4322 and MRS2347 were unavailable, only qualitative identification of metabolites could be made as ion peak heights/areas could not be compared due to potential differences in ionization efficiency.

Results

Two time course protocols were utilized in assessing the plasma stability of MRS2365 in mouse and human plasma. Preliminary data were generated with EDTA-prepared plasma over a 240 minute time course. A subsequent study utilized timepoints from 1-30 minutes post-incubation, and the final study utilized a shorter time course of 5-90 seconds post-incubation. In all protocols, plasma stability was analyzed in plasma prepared from blood with either EDTA or lithium heparin as the anticoagulant. In vitro stability data for enalapril (mouse) and procaine (human) in plasma and whole blood were consistent with published values (data not shown).

In plasma stability studies utilizing EDTA-prepared plasma, MRS2365 was essentially stable over the course of the incubation out to 240 minutes post-incubation (FIGS. 3 and 4). Half-life values could not be calculated over the time course of the incubation, and thus were >240 minutes. In subsequent metabolite scouting analyzes, neither MRS2347 nor MRS4322 could be detected. These data suggested that MRS2365 was stable in vitro in mouse and human plasma.

Similar observations were made when the stability of MRS2365 was assessed in mouse and human whole-blood that had been treated with EDTA as the anticoagulant (FIGS. 5 and 6). In those studies, the half-life of MRS2365 in EDTA-treated mouse whole blood was 47 minutes, suggesting that EDTA did not completely inhibit clearance of MRS2365 in this matrix. However, MRS2365 was again completely stable in EDTA-treated human whole blood, with an estimated half-life of >240 minutes. No metabolites were detected in these whole blood studies.

These data were inconsistent with initial in vivo pharmacokinetic assessments of MRS2365 in mice that utilized heparin as a blood anticoagulant for plasma preparation, in which MRS2365 appeared to be rapidly cleared at a rate approximating cardiac output, suggesting extensive extrahepatic clearance of the compound. It is known that EDTA chelates divalent cations that are required for the enzymatic activity of ectonucleotidases, enzymes responsible for the dephosphorylation of nucleotides, that are present both on the surface of cell membranes and circulating in blood and plasma (See Ziganshin et al. Pflugers Arch. (1995) 429:412-418). Thus, it was possible that the primary metabolic pathway of the P2Y$_1$ agonist nucleotide analog MRS2365 was completely inhibited by the EDTA used to prepare the plasma and whole blood for studies described above.

To investigate this possibility, additional stability studies were conducted to compare the stability of MRS2365 in plasma that had been generated by either EDTA or lithium heparin, the latter being an anticoagulant with no reported inhibitory effects on ectonucleotidases. Studies were first conducted with heparinized plasma and whole blood over a time course of 0-30 minutes. Quantitation of MRS2365 concentrations revealed extremely low concentrations of MRS2365 at all timepoints, with insufficient data to calculate an in vitro half-life (data not shown). Since low/undetectable MRS2365 concentrations were observed at even the shortest timepoints in this study (0 and 1 minutes), the study was repeated with a significantly shorter time course (0-90 seconds) to compare in vitro stability in both EDTA- and heparin-treated plasma and to attempt to calculate an in vitro half-life. In this shorter study, MRS2365 was relatively stable in EDTA-treated mouse and human plasma (FIGS. 5 and 6); variability in MRS2365 concentrations were likely due to incomplete mixing at the initiation of the short timecourse and variability in sampling multiple timepoints over the course of the 90 second incubation period. However, in heparin-treated plasma, MRS2365 concentrations were extremely low at even the shortest (0 and 5 seconds) timepoints. MRS2365 was completely stable when incubated in phosphate-buffered saline.

Together, these data suggest that although MRS2365 is inherently stable in solution, it is rapidly degraded in mouse and human plasma and blood by a process that is inhibited by EDTA. Considering that MRS2365 is a nucleotide analog and EDTA is a known inhibitor of ectonucleotidases that dephosphorylate nucleotides, these data strongly suggest that MRS2365 is susceptible to rapid dephosphorylation in plasma and whole blood, consistent with the in vivo pharmacokinetic data generated for MRS2365 in mouse.

To further investigate the possibility of dephosphorylation of MRS2365 as the cause of instability in mouse and human plasma and whole blood, metabolite scouting was conducted in heparinized human plasma and blood following incubation of MRS2365 at 100 µM for 10 or 30 minutes; the higher substrate concentration was used to ensure detection of any metabolites formed. Representative ion chromatograms and product ion spectra under positive-ionization conditions are illustrated (FIGS. 7 and 8); negative-ionization chromatograms and product ion spectra yielded similar results (data not shown). Although the lack of chemical standards prevented the determination of absolute concentrations of metabolites, the relative abundances of metabolite M1 increased compared to metabolite M2 from 10 to 30 minutes post-incubation. Metabolites M2 and M1 parent ion chromatograms and resulting product ion spectra under both ionization conditions were consistent with the mass and structure of the dephosphorylated monophosphate metabolite MRS2347 and the fully dephosphorylated riboside metabolite MRS4322, respectively (FIG. 9). The detection of both metabolites and the increase in abundance of metabolite M1 (MRS4322) relative to metabolite M2 (MRS2347) suggested a stepwise dephosphorylation of MRS2365 in human plasma and blood, progressing through the monophosphorylated intermediate MRS2347 that is then further dephosphorylated to the unphosphorylated riboside MRS4322.

Together, these data support the hypothesis that MRS2365 is rapidly metabolized in plasma and blood by circulating ectonucleotidases that dephosphorylate the parent compound, ultimately resulting in the unphosphorylated riboside MRS4322. This process is inhibited by EDTA, an agent known to chelate divalent cations that are required for ectonucleotidase activity.

Example 5: Neuroprotective Efficacy of MRS4322 after TBI in Mice

Purpose

This study was designed to determine the neuroprotective efficacy of MRS4322 in mice subjected to traumatic brain injury (TBI) and to compare free mice treated with MRS2365 and an adenosine A$_3$ receptor full agonist, Cl-IB-MECA.

Methods

Chemicals: MRS4322 was obtained courtesy Dr. Ken Jacobson of the National Institute of Diabetes, Digestive and Kidney Diseases (Bethesda, MD). Cl-IB-MECA is commercially available from Tocris Biosciences (Bristol, UK) and several other vendors. All other chemicals were obtained from Sigma-Aldrich (St. Louis, MO).

Animals and traumatic brain injury (TBI): TBI was performed with a controlled closed skull injury model as described in Talley-Watts et al. 2012 (*J. Neurotrauma* 30, 55-66). Following the method described therein, a pneumatic impact device was used to generate a moderate TBI leaving the skull and dura matter intact. To achieve this, C57BL/6 mice were anesthetized with isoflurane (3% induction, 1% maintenance) in 100% oxygen. A body temperature of 37° C. was maintained using a temperature-controlled heated surgical table. A small midline incision was made on the scalp using aseptic surgical techniques. A 5 mm stainless steel disc was positioned on the skull and fixed using superglue on the right parietal bone between bregma and lamda over the somatosensory cortex. The mouse was then positioned on a stage directly under the pneumatic impact tip. A calibrated impact was delivered at 4.5 m/s at a depth of 2 mm which generates a moderate injury in the mouse. Scalp incisions were closed using 4-0 nylon braided suture and antibiotic ointment applied to the incision. Mice were placed in a Thermo-Intensive Care Unit (Braintree Scientific model FV-1; 37° C.; 27% 02) and monitored until fully awake and moving freely. Thirty minutes following injury or sham (uninjured), mice were treated with either vehicle (saline) or drugs (MRS4322, Cl-IB-MECA or MRS2365). Doses of MRS4322, Cl-IB-MECA and MRS2365 were 0.16, 0.24 and 0.2 mg/kg, respectively, each equivalent to equimolar doses of approximately 0.5 µmol/kg.

Western Blot Analysis for GFAP: At selected survival times, mice were anesthetized under isoflurane and sacrificed. The brain was removed and placed on ice for dissection into impacted and non-impacted brain hemispheres. The isolated tissue was rapidly homogenized in chilled homogenization buffer (0.32 M Sucrose, 1 mM EDTA, 1 M Tris-HCL pH=7.8) on ice using a Wheaton glass dounce (20 strokes). The homogenate was transferred to a 2 mL tube and centrifuged at 1000 g for 10 minutes at 4° C. and the supernatant was collected and analyzed. Protein concentration was determined by the BCA assay using a 1:50 dilution. 100 µg of protein was removed as an aliquot for each sample and Laemmli buffer containing β-mercaptoethanol added and the sample placed in a heat block for 3 minutes at 95° C. Samples were loaded on a 12% gel and ran at 80 V for 20 minutes followed by 40 minutes at 130 V. Samples were transferred to nitrocellulose membrane at 100 V for 1 hour. The membrane was blocked with 5% milk in TBS-T for 30 minutes. GFAP (1:1000-Imgenex IMG-5083-A) was added and placed at 4° C. overnight. The membrane was washed with TBS-T three times for 10 minutes. Secondary antibody for GFAP (Donkey anti-rabbit HRP conjugated (Immuno-Jackson Laboratories; 711-035-152; 1:20000) was applied at room temperature for 1 hour. The membranes were washed with TB S-T for 15 minutes (3 times) and developed using the Western Lightning Plus-ECL kit (PerkinElmer, Inc.) following manufacturer's directions.

Results

Figure 12:
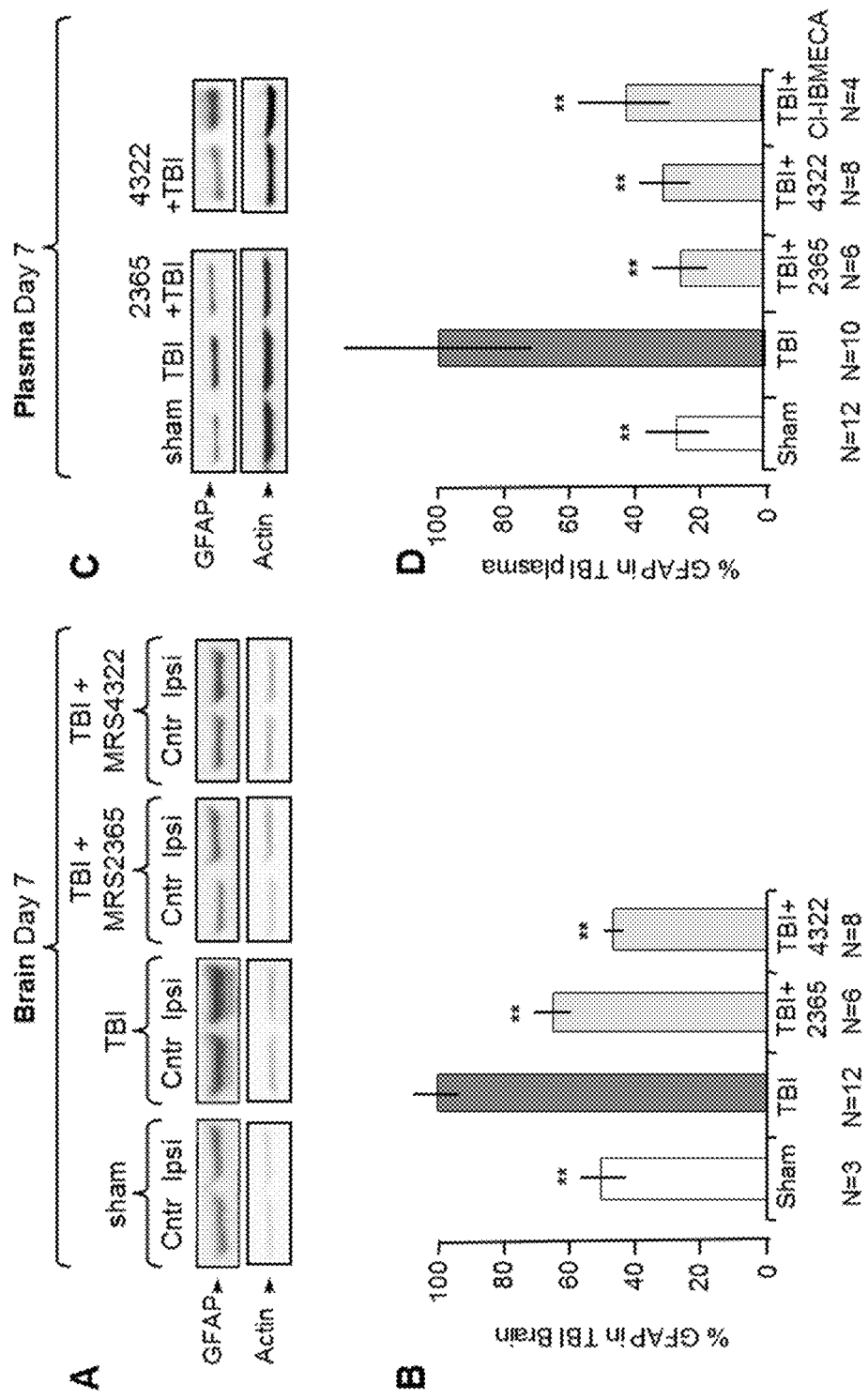
FIG. 12A-D shows the results of MRS4322, Cl-IB-MECA and MRS2365 treatments on mice exposed to TBI or sham (control experiment). TBI normally induces increases in GFAP expression. Mice underwent sham or TBI (on Ipsilateral side of brain) and received treatments as labeled 30 min post-TBI. Plasma was obtained from mice at 7 days post-injury, then the mice were sacrificed to obtain brain homogenates from the ipsilateral ("Ipsi") and contralateral ("Cntr") hemispheres (middle third). Western blot analysis were normalized to actin.

MRS4322 reduces GFAP expression in the mouse brains following TBI. Glial Fibrillary acidic protein (GFAP) expression was used as a biomarker for reactive gliosis after TBI (Talley-Watts et al. 2012; Sofroniew, 2005). We performed Western blot analysis for GFAP expression in Sham, TBI or TBI retreated (MRS4322 or MRS2365) mice sacrificed at 7 days post-injury. First, western blot analysis confirmed that TBI induced a significant increase in GFAP expression, both in the Ipsilateral (where the impact was centered) and contralateral sides of the brain at 7 days post-injury (FIG. 12A). GFAP expression was significantly lower in blots from mice treated with MRS4322 or MRS2365, which were injected within 30 minutes of the initial trauma (FIG. 12A). For loading controls, beta-actin western blots were used and shown below the respective lanes. Western blots shown in FIG. 12A were all obtained from a representative experiment and were run on the same gel. Data averaged from 3 separate experiments and showing the relative change in GFAP/actin ratios (band intensities measured in Image J software) are presented as mean+/−SEM in FIG. 12B. Values have been normalized to TBI levels at day 7 (100%) in order to consolidate the data. The total number of mice for a given experimental treatment is indicated by N in FIG. 12B.

MRS4322 and an Adenosine A3 Receptor agonist reduce GFAP expression in the mouse plasma following TBI. GFAP levels in the plasma have also been used as a biomarker for TBI, due to the breakdown of the blood brain barrier (BBB) after a trauma. Consequently, we also collected plasma samples at day 7 from TBI mice. Similar to brain tissue, we found that GFAP levels were easily detected at day 7 by western blot analysis (FIG. 12C). More importantly, we found that western blots obtained the plasma of TBI-mice treated with either MRS4322 or Cl-IB-MECA (Adenosine $A_3$ receptor agonist) exhibited significantly reduced levels of GFAP relative to actin (FIG. 12C). Histogram plots of the average GFAP/actin ratios for each experimental condition are presented in FIG. 12D. The total number of mice per experimental treatment is indicated by the value N.

MRS4322 is a low-affinity (4900 nM) agonist of the $A_3$ receptor in the mouse. Conversely, Cl-IB-MECA is a high-affinity (0.18 nM) agonist in the mouse—the differences in affinity of these two compounds is approximately 25,000-fold. However, in the mouse photothrombotic stroke and TBI models, MRS4322 demonstrates significant efficacy that is blocked by the A3 antagonist MRS1523, whereas Cl-IB-MECA is either inactive (stroke) or weakly active (TBI, FIG. 12). This is clearly a non-obvious result from the perspective of receptor affinity. Our current explanation for this finding is based on proprietary ADME/PK data we have generated for MRS4322 and Cl-IB-MECA. Cl-IB-MECA is a lipophilic compound (c Log P approx 2.5) that is highly bound to plasma proteins (free fraction 0.002) and highly bound nonspecifically to brain tissue (free fraction 0.002). MRS4322 is a very hydrophilic compound (c Log P<0) that has a very large unbound fraction in plasma (0.74) and brain (0.13). Only unbound drug is available for distribution across membranes and interaction with receptors. Thus, despite its lower receptor affinity, the fraction of MRS4322 available to interact with the A3 receptor in these mouse models is at least 1000-fold higher than that of Cl-IB-MECA. We believe that these significant differences in compound physicochemical properties and ADME/PK characteristics contribute to the non-obvious efficacy of MRS4322 as compared to Cl-IB-MECA (and MRS5698, another lipophilic and highly-bound/high-affinity full $A_3R$ agonist) in these mouse models.

Biased Agonism. The adenosine $A_3$ receptor is a G protein-coupled pleiotropic receptor, i.e. agonism of this receptor potentially activates multiple downstream pathways via multiple G proteins as well as Beta-arrestin. Pathways that are activated by $A_3$ receptor agonism have currently been identified, but may not be limited to, Gq11-mediated intracellular calcium mobilization, Gi-mediated modulation of cAMP production, and Gi-mediated phosphorylation of ERK1/2 and Akt. One aspect of our discoveries is in the $A_3$-mediated mobilization of intracellular calcium resulting in promotion of mitochondrial ATP production in astrocytes.

An emerging concept in receptor pharmacology is biased agonism. This concept states that for pleiotropic receptors there are actually different classes of agonists, some of which may activate all downstream pathways while others demonstrate bias in activating a subset of the downstream pathways. In drug discovery and receptor pharmacology, biased agonism introduces the possibility of increased specificity in pathway activation with fewer off-target effects, i.e. fewer side-effects. There is evidence for biased agonism for the $A_3$ receptor. However, prototypical high-affinity agonists such as Cl-IB-MECA and MRS5698 are full agonists that do not demonstrate biased activation of the aforementioned downstream pathways. Accordingly, and without wishing to be bound by any particular theory, it is believed that MRS4322 is a biased agonist that preferentially activates intracellular calcium mobilization with less/no activation of the other $A_3$-mediated pathways. This finding explains the MRS4322 efficacy observed in mouse stroke and TBI models relative to the full/unbiased agonists Cl-IB-MECA and MRS5698.

Example 6: Neuroprotective Efficacy of MRS4322 After Stroke in Mice

Purpose

This study was designed to determine the neuroprotective efficacy of MRS4322 in mice subjected to stroke and compare mice treated with MRS2365, with and without the $A_3$ receptor antagonist MRS1523, and in comparison to full $A_3R$ agonists MRS5698 and Cl-IB-MECA. MRS1523 has the following structure:

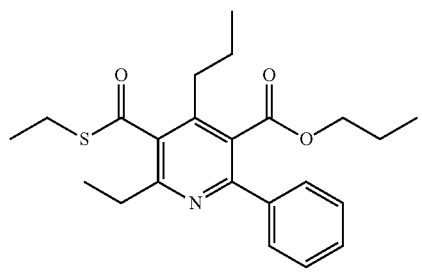

MRS1523

Methods

Chemicals: MRS4322 was obtained courtesy of Dr. Ken Jacobson of the National Institute of Diabetes, Digestive and Kidney Diseases (Bethesda, MD). Cl-IB-MECA, MRS5698 and MRS2365 are commercially available from Tocris Bioscience (Bristol, UK) and several other vendors. All other chemicals were obtained from Sigma-Aldrich (St. Louis, MO).

Photothrombosis-induced Stroke: Photothrombosis was performed as described in Zheng et al 2010 (PloS One 5 (12): e14401). In brief, Rose Bengal is a fluorescent dye that when injected into the vasculature and excited, generates singlet oxygen that damages the endothelial wall and induces a local thrombosis (clot). Using this technique, mice were given a 0.1 mL tail-vein injection of sterilized Rose Bengal (RB, Sigma, U.S.A.) in artificial cerebral spinal fluid (aCSF). The RB concentration was 20 mg/mL. A cortical region was centered in the imaging field and illuminated with a green laser (543 nm, 5 mW) using a 0.8-NA 40× water-immersion objective (Nikon, Tokyo). The clot formation was monitored in real time until the targeted vessel or downstream capillaries were firmly occluded. Stable clots were subsequently identified by a non-fluorescent vessel segmentation ending with highly fluorescent regions. In control experiments, either laser illumination or Rose Bengal itself did not lead to clot formation. Treatments, MRS4322 (0.16 mg/kg; 0.5 µmol/kg) or MRS2365 (0.24 mg/kg; 0.5 µmol/kg) were introduced via intraperitoneal injections (i.p.). For experiments with $A_3$ receptor antagonist MRS1523, mice were administered intraperitoneal injections (2 mg/kg) at the 0 and 2 hour timepoints to ensure receptor antagonism throughout the course of the study.

Animals and Photothrombosis-induced Stroke: Stroke was performed as described in Zheng et al 2010 (PloS One 5 (12): e14401). Female C57Bl/6 mice (4-6 months) were used in this study. From the methods of this manuscript: Mice were anesthetized at 3% isoflurane with 100% oxygen and subsequently maintained at 1% isoflurane through a nosecone. Depth of anesthesia was monitored and regulated according to vital signs, pinch withdrawal and eye blinks. Body temperature was maintained at 37° C. by a feedback-controlled heating pad (Gaymar T/Pump). Vital signs including oxygen saturation, respiratory rate, and heart rate were continuously monitored by using the MouseOx system (STARR Life Sciences). The hair on each mouse's head was trimmed and a small incision was made in the scalp to expose the skull. A custom-made stainless steel plate was glued to the skull with VetBond Tissue Adhesive (3M, St Paul, MN). A cranial thinned-skull imaging window was created over the right primary somatosensory cortex (~1.5 mm posterior to Bregma and 2 mm lateral from midline) depending on the experiment. In brief, a large region of the skull was first thinned with the electric drill and then further thinned with a surgical blade. The final thickness of the thinned skull was approximately 50 µm. After the cranial imaging window was created, mice were transferred to microscope stage and used for photothrombosis or imaging experiments. For the repeat imaging experiments, the plate was carefully detached from the skull and the scalp was sutured (Ethicon 6-0 sild suture). After each experiment, the mice were either returned to cages until the next timepoint or sacrificed. All procedures were approved by the Institutional Animal Care and Use Committee (IACUC) at University of Texas Health Science Center at San Antonio. Thirty minutes following stroke or sham (uninjured), mice were treated with either vehicle (saline) or drugs (MRS4322, MRS2365, MRS5698 or Cl-IBMECA).

Post photothrombotic infarction evaluation. The size of cerebral infarcts was evaluated using 2,3,5-Triphenyltetrazolium chloride (TTC) staining as described in Zheng et al 2010 (PloS One 5 (12): e14401). In brief, RB-induced lesions in brain slices were stained with TTC. TTC is a colorless dye that stains healthy brain tissue red when reduced by the mitochondrial enzyme succinyl dehydrogenase (Bederson J B et al., 1986). The absence of staining in necrotic tissue is then used to define the area of a brain infarction. Mice were sacrificed by cervical dislocation, their brains removed and then placed in ice cold HBSS for 3 minutes. The brain was subsequently transferred to a brain mold (KOPF), sliced into 1 mm sections and immersed in 2% TTC (5 min) at 37° C. The sections were fixed in 10% buffered formaldehyde solution overnight at 4° C. Slices were imaged on a flatbed scanner (HP scanjet 8300) for analysis of the lesion size at 1200 dpi.

Results

Figure 13:
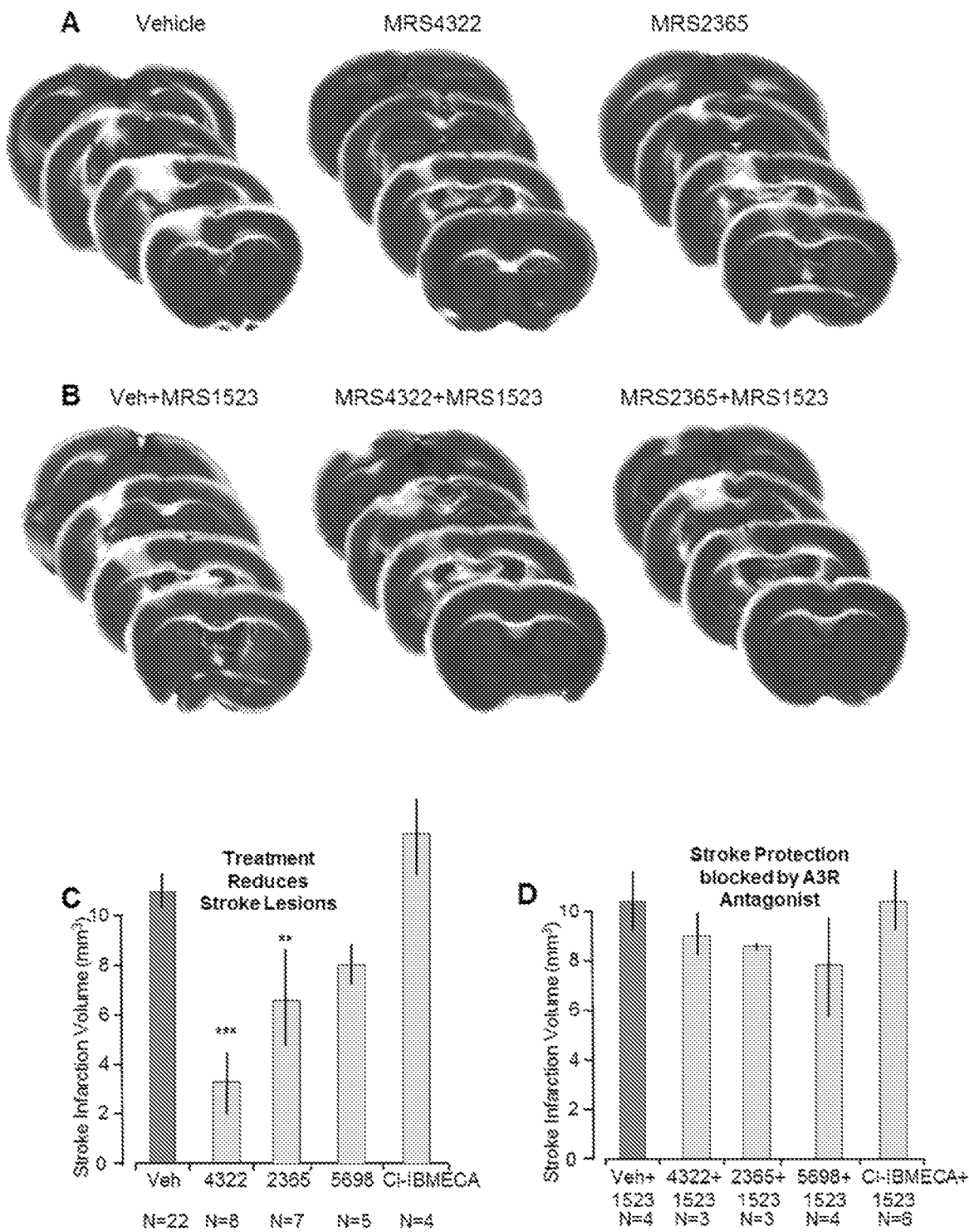
FIG. 13A-D shows the results of photothrombosis-induced stroke infarction experiments and the effects of administering MRS4322 and/or the specific adenosine type $A_3$ receptor antagonist MRS1523. MRS4322 reduced the effects of stroke infarction, but these effects were reversed by MRS1523.

MRS4322 treatment reduces brain infarctions after stroke. Multivessel photothrombotic strokes were induced in mice using tail-vein injected in conjunction with RB as described above. Within 30 minutes of clot formation, mice were injected intraperitoneally with either vehicle (saline control), MRS4322 (0.16 mg/kg; 0.5 µmol/kg) or MRS2365 (0.24 mg/kg; 0.5 µmol/kg). Twenty-four hours after the initial stroke, the brain infarction size was evaluated with TTC staining as described above. Representative TTC-stained brain slices are presented in FIG. 13A. We found that both MRS4322 and MRS2365 significantly reduced the size of the brain infarction. A histogram plot of the average size of brain infarctions for vehicle, MRS4322, MRS2365, MRS5698 or Cl-IBMECA-treated mice is presented in FIG. 13C. These data are pooled from 2 independent experiments. N refers to the total number of mice tested.

The $A_3$ Receptor Antagonist MRS1523 inhibits neuroprotection of MRS4322 and MRS2365 treatments after stroke. Multivessel photothrombotic strokes were induced in mice as described above. However, in this experiment, mice were treated with intraperatoneal injections of the $A_3$ receptor antagonist, MRS1523 (2 mg/kg) at the 0 and 2 hour timepoints to ensure receptor antagonism. Mice were then injected with either vehicle, MRS4322, MRS2365, MRS5698 or Cl-IBMECA within 30 minutes of clot formation at the concentrations described above. Twenty-four hours later, brain infarction sizes were evaluated with TTC staining. Representative TTC-stained brain slices are presented in FIG. 13B. We found that the size of brain infarctions in mice pretreated with MRS1523 were not reduced by treatments with either MRS4322 or MRS2365, or MRS5698. A histogram plot of the average size of brain infarctions for these experiments is presented in FIG. 13D. Data are pooled from 2 independent experiments. N refers to the total number of mice tested.

Example 7: Neuroprotective Efficacy of MRS1873 after Stroke in Mice

Purpose

This study was designed to determine the neuroprotective efficacy of MRS1873, which is the corresponding 2-chloro analog of MRS4322. Experiments were performed in mice subjected to stroke and compared mice treated with MRS4322 and vehicle treated.

Methods

Chemicals: MRS1873 and MRS4322 were obtained courtesy Dr. Ken Jacobson of the National Institute of Diabetes, Digestive and Kidney Diseases (Bethesda, MD). MRS1873 has the following structure:

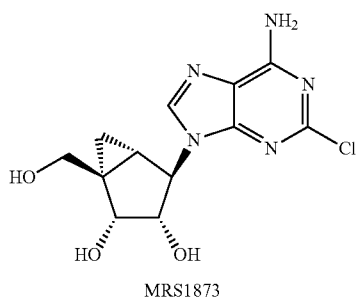 [SMILES: Nc1nc(Cl)nc2c1ncn2[C@H]1[C@H](O)[C@H](O)[C@]2(CO)C[C@H]12]

MRS1873

Photothrombosis-induced Stroke: Photothrombosis was performed as described in Zheng et al. 2010 (PloS One 5 (12): e14401). In brief, Rose Bengal is a fluorescent dye that when injected into the vasculature and excited, generates singlet oxygen that damages the endothelial wall and induces a local thrombosis (clot). Using this technique, mice were given a 0.1 ml tail-vein injection of sterilized Rose Bengal (RB, Sigma, U.S.A.) in artificial cerebral spinal fluid (aCSF). The RB concentration was 20 mg/ml. A cortical region was centered in the imaging field and illuminated with a green laser (543 nm, 5 mW) using a 0.8-NA 40× water-immersion objective (Nikon, Tokyo). The clot formation was monitored in real time until the targeted vessel or downstream capillaries were firmly occluded. Stable clots were subsequently identified by a non-fluorescent vessel segmentation ending with highly fluorescent regions. In control experiments, either laser illumination or Rose Bengal itself did not lead to clot formation. Treatments, MRS1873 (100 ul of 100 uM) or MRS4322 (100 ul of 100 uM) were introduced via intraperitoneal injections (i.p.).

Animals and Photothrombosis-induced Stroke: Stroke was performed as described in Zheng et al 2010 (PloS One 5 (12): e14401). Female C57Bl/6 mice (4-6 months) were used in this study. From the methods of this manuscript: Mice were anesthetized at 3% isoflurane with 100% oxygen and subsequently maintained at 1% isoflurane through a nosecone. Depth of anesthesia was monitored and regulated according to vital signs, pinch withdrawal and eye blinks. Body temperature was maintained at 37° C. by a feedback-controlled heating pad (Gaymar T/Pump). Vital signs including oxygen saturation, respiratory rate, and heart rate were continuously monitored by using the MouseOx system (STARR Life Sciences). The hair on the mouse head was trimmed and a small incision was made in the scalp to expose the skull. A custom-made stainless steel plate was glued to the skull with VetBond Tissue Adhesive (3M, St Paul, MN). A cranial thinned-skull imaging window was created over the right primary somatosensory cortex (~1.5 mm posterior to Bregma and 2 mm lateral from midline) depending on the experiment. In brief, a large region of the skull was first thinned with the electric drill and then further thinned with a surgical blade. The final thickness of the thinned skull was approximately 50 µm. After the cranial imaging window was created, mice were transferred to microscope stage and used for photothrombosis or imaging experiments. For the repeat imaging experiments, the plate was carefully detached from the skull and the scalp was sutured (Ethicon 6-0 sild suture). After each experiment, the mice were either returned to cages until the next timepoint or sacrificed. All procedures were approved by the Institutional Animal Care and Use Committee (IACUC) at University of Texas Health Science Center at San Antonio. Thirty minutes following stroke or sham (uninjured), mice were treated with either vehicle (saline) or drugs (MRS4322 or MRS2365).

Post photothrombotic infarction evaluation. The size of cerebral infarcts was evaluated using 2,3,5-Triphenyltetrazolium chloride (TTC) staining as described in Zheng et al 2010 (PloS One 5 (12): e14401). In brief, RB-induced lesions in brain slices were stained with TTC. TTC is a colorless dye that stains healthy brain tissue red when reduced by the mitochondrial enzyme succinyl dehydrogenase (Bederson J B et al., 1986). The absence of staining in necrotic tissue is then used to define the area of a brain infarction. Mice were sacrificed by cervical dislocation, their brains removed and then placed in ice cold HBSS for 3 minutes. The brain was subsequently transferred to a brain mold (KOPF), sliced into 1 mm sections and immersed in 2% TTC (5 min) at 37° C. The sections were fixed in 10% buffered formaldehyde solution overnight at 4° C. Slices were imaged on a flatbed scanner (HP scanjet 8300) for analysis of the lesion size at 1200 dpi.

Results

Figure 14:
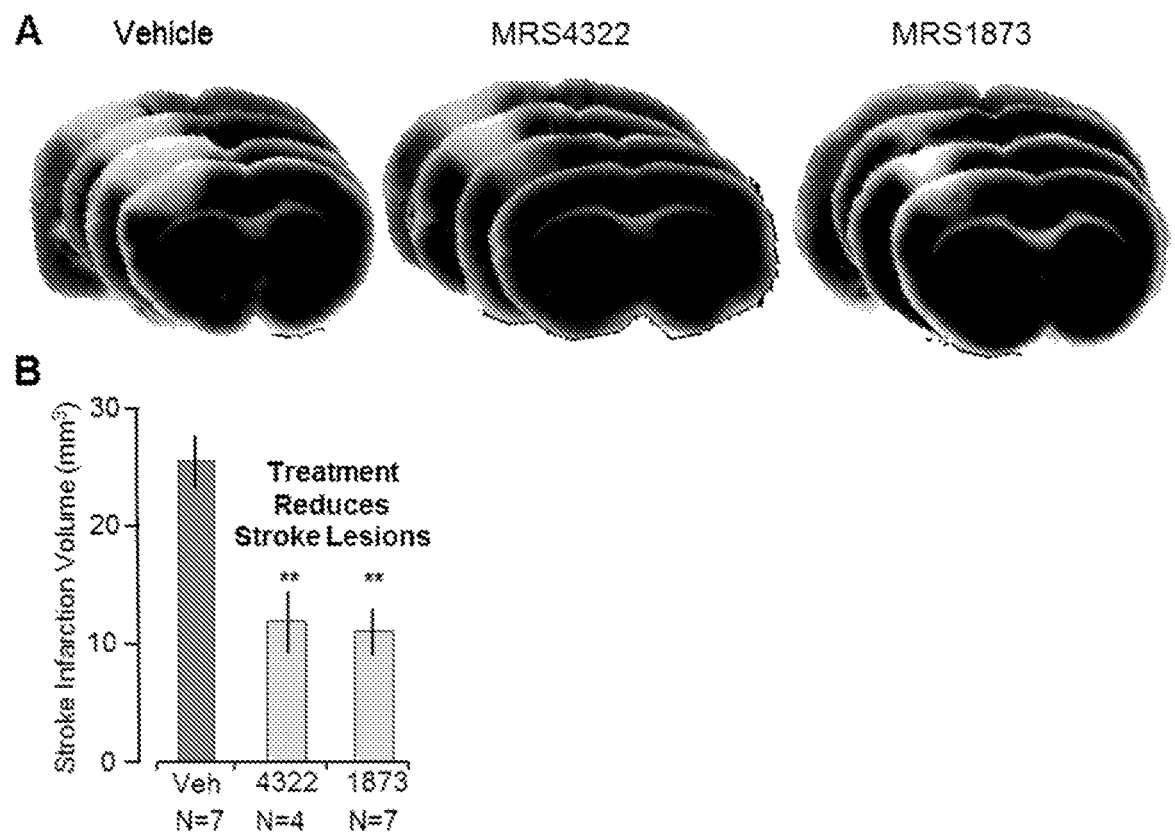
FIG. 14A-B shows the results of photothrombosis-induced stroke infarction experiments and the effects of administering MRS4322, MRS1873, or vehicle. Photothrombosis-induced stroke infarctions are reduced by MRS4322 and MRS1873.

MRS1873 treatment reduces brain infarctions after stroke: Multivessel photothrombotic strokes were induced in mice using tail-vein injected in conjunction with RB as described above. Within 30 minutes of clot formation, mice were injected intraperitoneal with either vehicle (saline control), MRS1873 (100 ul of 100 uM) or MRS4322 (100 ul of 100 uM). Twenty-four hours after the initial stroke, the brain infarction size was evaluated with TTC staining as described above. Representative TTC-stained brain slices are presented in FIG. 14B. We found that both MRS1873 and MRS4322 significantly reduced the size of the brain infarction. A histogram plot of the average size of brain infarctions for vehicle, MRS1873 and MRS4322-treated mice is presented in FIG. 14B. These data are pooled from 3 independent experiments. N refers to the total number of mice tested.

Pharmacokinetics and Rationale for Efficacy

MRS1873 is the 2-Cl analog of MRS4322 and is also an adenosine $A_3$ agonist. MRS1873 physicochemical properties are identical to those of MRS4322 in terms of low molecular weight, hydrophilicity (c Log P<0) and topological polar surface area. Since ADME/PK parameters such as plasma and brain binding, clearance and volume of distribution are driven by these physicochemical properties, we have demonstrated similar pharmacokinetics for MRS4322 and MRS1873. In addition, we have demonstrated similar efficacy for MRS4322 and MRS1873 in a murine photothrombotic model of stroke.

Example 8: Experimental Protocol for Determining Biased Agonism of Compounds at $A_3$ Adenosine Receptor ($A_3R$)

The following assay may be used to determine whether a disclosed compound, such as MRS4322 or MRS1873, exhibits biased agonism (also known as functional selectivity or agonist trafficking) at the $A_3$ receptor.

Materials. Fluo-4, Dulbecco's modified Eagle's medium (DMEM), and penicillin-streptomycin may be purchased from Invitrogen (Carlsbad, CA). Adenosine deaminase (ADA) and hygromycin-B may be purchased from Roche (Basel, Switzerland). Fetal bovine serum (FBS) may be purchased from ThermoTrace (Melbourne, Australia). AlphaScreen SureFire extracellular signal-regulated kinases 1 and 2 (ERK1/2), Akt 1/2/3, and cAMP kits may be obtained from PerkinElmer (Boston, MA). All compounds prefixed with MRS may be synthesized as described previously (Tosh et al., 2012a,b). All other reagents were purchased from Sigma-Aldrich (St. Louis, MO).

Cell Culture. The sequence of the human $A_3R$ may be cloned into the Gateway entry vector, pDONR201, and then transferred in the Gateway destination vector, pEF5/FRT/V5-dest, using methods described previously (Stewart et al., 2009). $A_3$-FlpIn-CHO cells may be generated using methods described previously (May et al., 2007) and maintained at 37° C. in a humidified incubator containing 5% $CO_2$ in DMEM supplemented with 10% FBS and the selection antibiotic hygromycin-B (500 μg/ml). For cell survival, ERK1/2 phosphorylation, Akt 1/2/3 phosphorylation, and calcium mobilization assays, cells may be seeded into 96-well culture plates at a density of 4×104 cells/well. After 6 hours, cells are washed with serum-free DMEM and maintained in serum-free DMEM for 12-18 hours at 37° C. in 5% $CO_2$ before assaying. For cAMP assays, cells may be seeded into 96-well culture plates at a density of 2×104 cells/well and incubated overnight at 37° C. in 5% $CO_2$ prior to assay.

Cell Survival Assays. Media is removed and replaced with HEPES-buffered saline solution (10 mM 4-(2-hydroxyethyl)-1-piperazineethanesulfonic acid (HEPES), 146 mM NaCl, 10 mM D-glucose, 5 mM KCl, 1 mM $MgSO_4$, 1.3 mM $CaCl_2$, and 1.5 mM $NaHCO_3$, pH 7.45) containing ADA (1 U/ml) and penicillin-streptomycin (0.05 U/ml) in the absence and presence of $A_3R$ ligands. Plates are then maintained at 37° C. in a humidified incubator for 24 hours, after which 5 mg/ml propidium iodide is added to cells. Plates may be then read on an EnVision plate reader (PerkinElmer), with excitation and emission set to 320 nm and 615 nm, respectively. Data will be normalized to 100% cell survival and 0% cell survival, determined at t=0 hours in HEPES buffer and t=24 hours in Milli-Q water, respectively.

ERK1/2 and Akt 1/2/3 Phosphorylation Assays. A concentration-response curve of ERK1/2 and Akt 1/2/3 phosphorylation for each ligand may be performed in serum-free DMEM containing 1 U/ml ADA (5-minute exposure at 37° C.). Agonist stimulation may be terminated by removal of media and the addition of 100 ml of SureFire lysis buffer to each well. Plates are then agitated for 5 minutes. Detection of pERK1/2 may involve an 80:20:120:1:1 v/v/v/v/v dilution of lysate: activation buffer: reaction buffer: AlphaScreen acceptor beads: AlphaScreen donor beads in a total volume of 11 ml in a 384-well ProxiPlate. Plates may be incubated in the dark at 37° C. for 1 hour followed by measurement of fluorescence by an EnVision plate reader (PerkinElmer) with excitation and emission set to 630 nm and 520-620 nm, respectively. Detection of Akt 1/2/3 phosphorylation may employ a 40:9.8:39.2:1 v/v/v/v dilution of lysate: activation buffer: reaction buffer: AlphaScreen acceptor beads in a total volume of 91 in a 384-well Proxiplate. Plates may be incubated in the dark at room temperature for 2 hours, after which a 19:1 v/v dilution of dilution buffer: AlphaScreen donor beads may be added in a total volume of 11 μl. Plates may be incubated at room temperature for a further 2 hours, followed by measurement of fluorescence by an EnVision plate reader (PerkinElmer) with excitation and emission set to 630 nm and 520-620 nm, respectively. Agonist concentration-response curves are normalized to the phosphorylation mediated by 10% FBS (5-minute stimulation).

Calcium Mobilization Assays. Media may be removed from 96-well plates and replaced with HEPES-buffered saline solution containing 1 U/ml ADA, 2.5 mM probenecid, 0.5% bovine serum albumin (BSA), and 1 M Fluo4. Plates may be incubated in the dark for 1 hour at 37° C. in a humidified incubator. A FlexStation plate reader (Molecular Devices, Sunnyvale, CA) may perform the addition of HEPES-buffered saline solution in the absence and presence of agonist and measured fluorescence (excitation, 485 nm; emission, 520 nm) every 1.52 seconds for 75 seconds. The difference between the peak and baseline fluorescence may be measured as a marker for intracellular $Ca^{2+}$ mobilization. $A_3R$ agonist concentration-response curves may be normalized to the response mediated by 100 μM ATP to account for differences in cell number and loading efficiency.

Inhibition of cAMP Accumulation Assays. Media may be replaced with a stimulation buffer (140 mM NaCl, 5 mM KCl, 0.8 M $MgSO_4$, 0.2 mM $Na_2HPO_4$, 0.44 mM $KH_2PO_4$, 1.3 mM $CaCl_2$, 5.6 mM D-glucose, 5 mM HEPES, 0.1% BSA, 1 U/ml ADA, and 10 μM rolipram, pH 7.45) and incubated at 37° C. for 1 hour. Inhibition of cAMP accumulation may be assessed by preincubation of $A_3$-FlpIn-CHO cells with $A_3R$ agonists for 10 minutes, after which 3 μM forskolin was added for a further 30 minutes. The reaction may be terminated by rapid removal of buffer and addition of 50 μl ice-cold 100% ethanol. Ethanol is allowed to evaporate before the addition of 50 μl detection buffer (0.1% BSA, 0.3% Tween-20, 5 mM HEPES, pH 7.45). Plates are agitated for 10 minutes, after which 10 μl lysate was transferred to a 384-well Optiplate. Detection may employ addition of a 5 μl 1:49 v/v dilution of AlphaScreen acceptor beads: stimulation buffer. Following this, a 15 μl 1:146:3 v/v/v dilution of AlphaScreen donor beads: detection buffer: 3.3 U/μl biotinylated cAMP to form a total volume of 30 μl. The donor bead/biotinylated cAMP mixture may be equilibrated for 30 minutes prior to addition. Plates may be incubated overnight in the dark at room temperature, followed by measurement of fluorescence by an EnVision plate reader (PerkinElmer) with excitation and emission set to 630 nm and 520-620 nm, respectively. Agonist concentration-response curves may be normalized to the response mediated by 3 μM forskolin (0%) or buffer (100%) alone.

Molecular Modeling. Docking simulations can be performed for all the compounds investigated in this study using homology models of the human $A_3R$. In particular, three previously reported models can be used: a model entirely based on an agonist-bound $hA_{2A}AR$ crystal structure (PDB ID: 3QAK), a model based on a hybrid $A_{2A}AR$-β2 adrenergic receptor template, and a model based on a hybrid $A_{2A}AR$-opsin template (β2 adrenoceptor X-ray structure PDB ID: 3SN6; opsin crystal X-ray crystal structure PDB ID: 3DQB) (Tosh et al., 2012a). Models based on hybrid templates will show an outward movement of TM2 compared with the $A_{2A}AR$-based model. Structures of $A_3R$ ligands may be built and prepared for docking using the Builder and the LigPrep tools implemented in the Schrödinger suite (Schrödinger Release 2013-3, Schrödinger, LLC, New York, NY, 2013). Molecular docking of the ligands at the $A_3R$ models may be performed by means of the Glide package part of the Schrödinger suite. In particular, a Glide Grid may be centered on the centroid of some key residues of the binding pocket of adenosine receptors, namely, Phe (EL2), Asn (6.55), Trp (6.48), and His (7.43). The Glide Grid may be built using an inner box (ligand diameter midpoint box) of 14 Å×14 Å×14 Å and an outer box (box within which all the ligand atoms must be contained) that extends 25 Å in each direction from the inner one. Docking of ligands may be performed in the rigid binding site using the XP (extra precision) procedure. The top scoring docking conformations for each ligand may be subjected to visual inspection and analysis of protein-ligand interactions to select the proposed binding conformations in agreement with the experimental data.

Data Analysis. Statistical analyses and curve fitting may be performed using Prism 6 (GraphPad Software, San Diego, CA). To quantify signaling bias, agonist concentration-response curves may be analyzed by nonlinear regression using a derivation of the Black-Leff operational model of agonism, as described previously (Kenakin et al., 2012; Wootten et al., 2013; van der Westhuizen et al., 2014). The transduction coefficient, τ/KA [expressed as a logarithm, Log (τ/KA)], may be used to quantify biased agonism. To account for cell-dependent effects on agonist response, the transduction ratio may be normalized to the values obtained for the reference agonist, IB-MECA, MECA, to generate ALog (τ/KA). To determine the bias for each agonist at different signaling pathways, the ALog (τ/KA) will be normalized to a reference pathway, pERK1/2, to generate AALog (τ/KA). Bias may be defined as $10^{AALog(\tau/KA)}$ where a lack of bias will result in values that are not statistically different from 1, or 0 when expressed as a logarithm. All results may be expressed as the mean 6 S.E.M. Statistical analyses would involve an F test or a one-way analysis of variance with a Tukey or Dunnett's post hoc test, with statistical significance determined as P, 0.05.

Example 9: Synthetic Route for MRS4322

MRS4322 and similar compounds such as MRS1873 may be prepared according to methods known in the art. For example, MRS4322 may be prepared from D-ribose by following routes described in Choi, W. J. et al. J. Org. Chem. 2004, 69, 2634-2636, Tosh, D. K. et al. Purinergic Signalling 2015, 11, 371-387; and Chem. Eur. J., 2009, 15, 6244-6257. Schemes 1 and 2 below show the synthetic route.

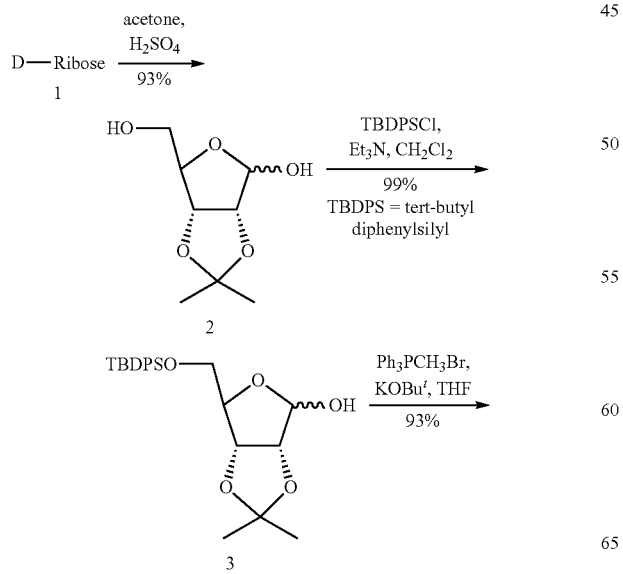

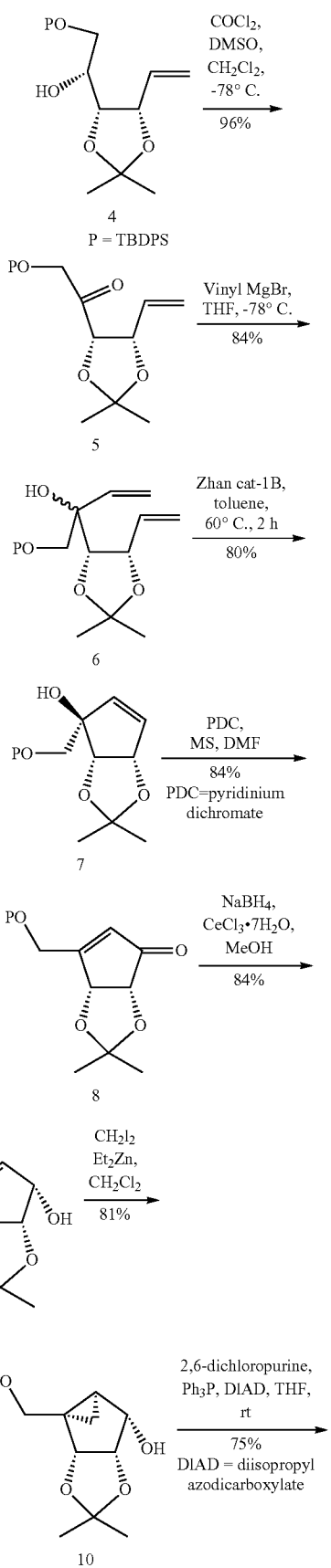

-continued

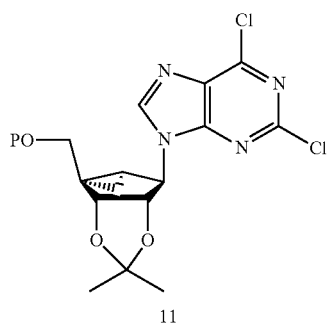

11

Zhan cat-1B has the following structure:

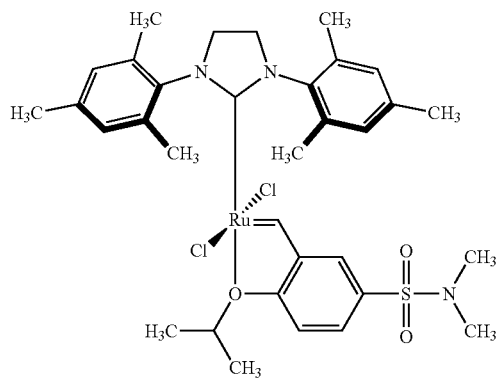

Scheme 2 shows the remainder of the synthesis.

Scheme 2: Synthesis of MRS4322

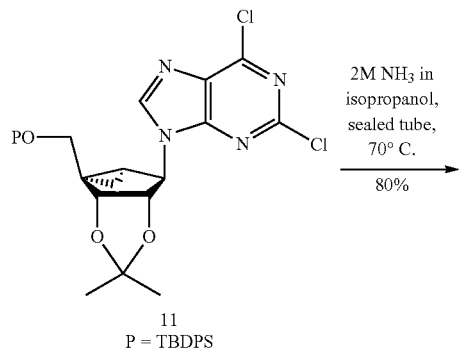
11
P = TBDPS

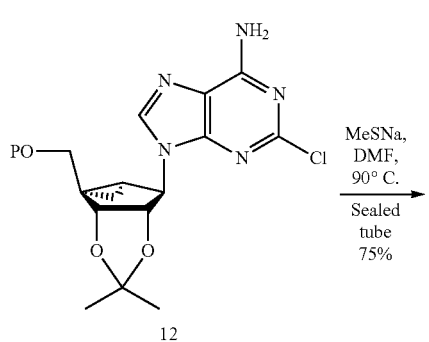
12

-continued

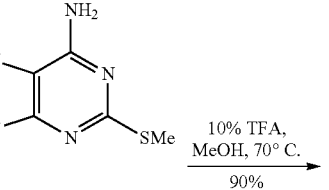
13

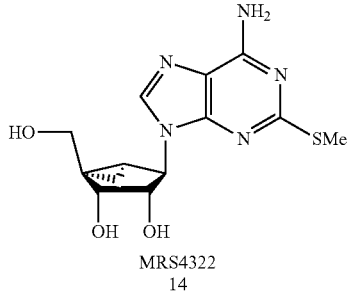
MRS4322
14

Example 10: Rationale for Cardioprotection of Disclosed Compounds

We have demonstrated the extremely rapid and quantitative dephosphorylation of P2Y1 agonists to compounds, such as, MRS4322 that are adenosine A3 agonists. These adenosine A3 agonists were surprisingly found to be efficacious in multiple murine models of stroke and traumatic brain injury, as described herein. Without wishing to be bound by any particular theory, it is believed that presently described A3 agonists, such as MRS4322 and MRS1873, are effective as cardioprotective agents.

Our data showing rapid and quantitative dephosphorylation of MRS2365 and related phosphorylated nucleosides to compounds such as MRS4322 and MRS1873 supports our claim that the purported cardioprotective efficacy of these P2X4 agonists is actually due to the adenosine A3 agonism of their dephosphorylated metabolites. Indeed, we have demonstrated that MRS1873 is an adenosine A3 agonist that is efficacious in stroke and traumatic brain injury models.

Example 11: Pharmacokinetics and Binding of MRS4322 Following Intravenous Administration to Neonatal Pigs Purpose This study was designed to determine the plasma, brain and CSF concentrations of MRS4322 following intravenous administration to neonatal pigs.

Methods

Chemicals. MRS4322 was obtained courtesy Dr. Ken Jacobson of the National Institute of Diabetes, Digestive and Kidney Diseases (Bethesda, MD).

Animals. Four-week old female neonatal pigs weighing approximately 7.5 Kg were used for this study, supplied by the Department of Bioengineering, University of Pennsylvania (Philadelphia, PA). Animals were equipped with brain microdialysis probes to obtain brain extracellular fluid samples for drug concentration determinations during the study. All studies were conducted under approved University of Pennsylvania IACUC protocols.

Drug Administration: MRS4322 was solubilized in DMSO and then diluted in saline to prepare dosing solution. A 10 mL volume of dosing solution was administered by intravenous bolus administration to each neonatal pig (n=3).

Tissue Sampling: Blood samples were obtained at 0.25, 0.5, 1, 2, 4 and 6 hours post-dose. Brain extracellular fluid samples were obtained from implanted microdialysis probes at 1, 4 and 6 hours post-dose. Whole blood (1 mL) was obtained at each timepoint and placed in vacutainer tubes containing heparin and immediately centrifuged for preparation of plasma; plasma was stored at −80° C. Brain extracellular and cerebrospinal fluid samples were stored at −80° C. At the time of euthanasia (6 hours post-dose), cerebrospinal fluid samples were obtained and frozen, while brain samples from the cortex and hippocampus were obtained by decapitation, rinsed in ice-cold phosphate-buffered saline and weighed. Brain samples were then immediately flash-frozen in liquid nitrogen and stored at −80° C.

Bioanalysis

Plasma, brain, brain extracellular fluid and cerebrospinal fluid concentrations of MRS4322 were determined by LC-MS/MS utilizing tolbutamide as an internal standard. The following table outlines the LC and MS/MS conditions employed:

TABLE 12

Bioanalytical Methods for MRS4322 Plasma, Brain, Brain Extracellular and Cerebrospinal Fluid Concentration Determinations System Components

| Module | Manufacturer | Model |
|---|---|---|
| LC | Waters | Acquity I Class |
| Autosampler | Waters | Acquity Sample Manager |
| MS Detection | AB Sciex | API 5500 QQQ |

HPLC Method

| Column | Phenomenex Kinetex C18 (2.1 × 50 mm, 2.6 μm) |
|---|---|
| Elution | Gradient, 0.6 mL/min Mobile Phase A: 0.1% Formic Acid Mobile Phase B: 0.1% Formic Acid in Acetonitrile |

MS Detection and Calibration for MRS4322 in Swine Plasma

Peak Name: Tolbutamide
Use as Internal Standard
Q1/Q3 Masses:
271.00/155.00 Da
Peak Name: MRS4322
Internal Standard:
Tolbutamide
Q1/Q3 Masses:
324.08/182.10 Da

| Fit | Linear | Weighting | 1/x |
|---|---|---|---|
| Intercept | 0.000570 | | |
| Slope | 0.00699 | | |
| Correlation coefficient | 0.9998 | | |
| Use Area | | | |

TABLE 12-continued

Bioanalytical Methods for MRS4322 Plasma, Brain, Brain Extracellular and Cerebrospinal Fluid Concentration Determinations MS Detection and Calibration for MRS4322 in Swine Brain Homogenate Peak Name: Tolbutamide
Use as Internal Standard
Q1/Q3 Masses:
271.00/155.00 Da
Peak Name: MRS4322
Internal Standard:
Tolbutamide
Q1/Q3 Masses:
324.08/182.10 Da

| Fit | Quadratic | Weighting | 1/x |
|---|---|---|---|
| a0 | 0.000244 | | |
| a1 | 0.00675 | | |
| a2 | −0.00000134 | | |
| Correlation coefficient | 0.9999 | | |
| Use Area | | | |

MS Detection and Calibration for MRS4322 in Swine ECF and CSF

Peak Name: Tolbutamide
Use as Internal Standard
Q1/Q3 Masses:
271.00/155.00 Da
Peak Name: MRS4322
Internal Standard:
Tolbutamide
Q1/Q3 Masses:
324.08/182.10 Da

| Fit | Quadratic | Weighting | 1/x |
|---|---|---|---|
| a0 | 0.000297 | | |
| a1 | 0.00783 | | |
| a2 | 0.000000130 | | |
| Correlation coefficient | 0.9998 | | |
| Use Area | | | |

For each tissue matrix, standard curves were created and LLOQ/ULOQ concentrations determined. The calibration ranges for all of the MRS4322 matrice's standard curves were 0.1-1000 ng/mL.

For bioanalysis of brain concentrations of MRS4322, brain samples were homogenized in ice-cold phosphate-buffered saline in a 4× dilution. Aliquots of the resulting diluted brain homogenate were treated with acetonitrile and analyzed by LC-MS/MS.

Results

Following intravenous administration to neonatal pigs, MRS4322 concentrations were detectable in plasma, brain, brain extracellular fluid and cerebrospinal fluid samples (FIG. 1B and FIG. 16, Table 13).

TABLE 13

Plasma, Brain, Brain Extracellular and Cerebrospinal Fluid Concentrations of MRS4322 in Neonatal Pigs Following Intravenous Administration

| Test Article | Matrix | Route | Dose (mg/kg) | Time (h) | 161128U | 161128U-1 | 161128U-2 | Mean | SD | N |
|---|---|---|---|---|---|---|---|---|---|---|
| | | | | | Plasma Concentration (ng/mL) by Subject | | | | | |
| MRS4322 | Plasma | IV | 0.2 | 0 | BLQ | BLQ | BLQ | BLQ | — | 0 |
| | | | | 0.25 | 133 | 120 | 163 | 139 | 22 | 3 |
| | | | | 0.5 | 85.3 | 54.1 | 98.7 | 79.4 | 22.9 | 3 |
| | | | | 1 | 58.9 | 51.4 | 63.0 | 57.8 | 5.9 | 3 |
| | | | | 2 | 27.2 | 18.7 | 46.8 | 30.9 | 14.4 | 3 |
| | | | | 4 | 23.3 | 21.9 | 28.7 | 24.6 | 3.6 | 3 |
| | | | | 6 | 15.3 | 9.08 | 20.8 | 15.1 | 5.9 | 3 |
| | | | | | Brain Concentration (ng/mL) by Subject | | | | | |
| MRS4322 | Brain Cortex | IV | 0.2 | 6 | 5.34 | 3.80 | 6.15 | 5.10 | 1.19 | 3 |
| | Brain Hippocampus | | | | 6.47 | 4.56 | 5.39 | 5.47 | 0.96 | 3 |
| | | | | | Extracellular Fluid Concentration (ng/mL) by Subject | | | | | |
| MRS4322 | ECF | IV | 0.2 | 1 | 1.55 | 0.641 | 1.70 | 1.30 | 0.57 | 3 |
| | | | | 4 | 0.693 | 0.579 | 1.36 | 0.941 | 0.388 | 3 |
| | | | | 6 | 0.602 | 0.459 | 1.08 | 0.714 | 0.326 | 3 |
| | | | | | Cerebro-Spinal Fluid Concentration (ng/mL) by Subject | | | | | |
| MRS4322 | CSF | IV | 0.2 | 6 | 1.37 | 1.04 | 1.75 | 1.39 | 0.36 | 3 |

BLQ = Below the Lower Limit of Quantitation (0.0975 ng/mL for Plasma)

TABLE 14

Plasma Pharmacokinetics of MRS4322 in Neonatal Pigs Following Intravenous Administration

| Test Article | Route | Dose (mg/kg) | Animal ID | C0 (ng/mL) | Cmax (ng/mL) | Tmax (hr) | AUClast (hr*ng/mL) | AUCINF (hr*ng/mL) | Cl (mL/min/kg) | Vz (L/kg) | Half Life (hr) |
|---|---|---|---|---|---|---|---|---|---|---|---|
| MRS4322 | IV | 0.2 | 161128U | 207 | 133 | 0.25 | 238 | 344 | 9.68 | 4.04 | 4.82 |
| | | | 161128U-1 | 286 | 120 | 0.25 | 203 | 233 | 14.3 | 2.86 | 2.31 |
| | | | 161128U-2 | 289 | 163 | 0.25 | 307 | 401 | 8.31 | 2.25 | 3.13 |
| | | | N | 3 | 3 | 3 | 3 | 3 | 3 | 3 | 3 |
| | | | Mean | 248 | 139 | 0.25 | 249 | 326 | 10.8 | 3.05 | 3.42 |
| | | | SD | 34.9 | 22.1 | 0.00 | 52.9 | 85.3 | 3.13 | 0.907 | 1.28 |
| | | | CV % | 14.1 | 15.9 | 0.0 | 21.2 | 26.1 | 29.1 | 29.8 | 37.4 |

Plasma concentrations allowed initial estimates of Tmax, Cmax, plasma clearance, volume of distribution, half-life and AUC (Table 14).

Although MRS4322 concentrations in the brain, brain extracellular fluid and cerebrospinal fluid were detectable, data was insufficient for estimation of half-life or other pharmacokinetic parameters other than Cmax and Tmax. However, based on the available plasma and brain data at 6 hours post-dose when samples were obtained for all matrices, it was estimated that the brain/plasma ratio of total drug was approximately 0.3 based on mean concentrations in plasma and brain.

These results confirm that circulating plasma concentrations of MRS4322 are detectable following intravenous administration to neonatal pigs, and that MRS4322 is well distributed to the brain under these dosing conditions.

Example 12: Plasma and Brain Binding of MRS4322 in the Neonatal Pigs

Purpose

This study was designed to determine the plasma and brain free fraction of MRS4322 in neonatal pigs.

Methods

Chemicals. MRS4322 was obtained courtesy Dr. Ken Jacobson of the National Institute of Diabetes, Digestive and Kidney Diseases (Bethesda, MD). Analytical-grade sulfamethoxazole and warfarin were obtained from commercial supplies at Seventh Wave Laboratories (Maryland Heights, MO). All other chemicals were obtained from Sigma-Aldrich (St. Louis, MO).

Animals and Tissue Preparation. Plasma and brain samples from female neonatal pigs were obtained from the University of Pennsylvania and stored at −80° C. until use.

Plasma ultrafiltrate blank samples were prepared by thawing frozen plasma and then pre-warming plasma in a humidified 5% CO2 chamber at 37 C for 60 minutes. Aliquots of 800 ul were transferred to Centrifree Centrifugal Filters (Ultracel regenerated cellulose (NMWL 30,000 amu) Lot R5JA31736) and centrifuged at 2900 RPM at 37 C for 10 minutes; plasma water filtrates were collected and used in preparation of standards, blanks and QC standards.

Brains were weighed and homogenized with 1:9 phosphate-buffered saline, pH 7.4 using an Omni tissue homogenizer. Brains from four mice were homogenized, pooled and mixed to form one sample.

Plasma Binding Determination. MRS4322, sulfamethaxazole and warfarin were solubilized in DMSO and then diluted in 1:1 acetonitrile:water to prepare 100 uM dialysis stock solutions. Sulfamethaxazole and warfarin were utilized as study standards with known plasma binding values. Plasma samples were pre-warmed for 60 minutes in a humidified, 5% $CO_2$ incubator maintained at 37° C. Three ml aliquots of pre-warmed plasma were each spiked with MRS4322, sulfamethaxazole or warfarin using 100 uM stock solutions for each compound resulting in final test concentrations of 1 uM. Spiked plasma samples were incubated on a rotary mixer in a humidified 5% $CO_2$ chamber at 37° C. for a minimum of 60 minutes. After 60 minutes, three 800 ul aliquots of each sample were added to Centrifree centrifugal filters. The filters were subjected to centrifugation at 2900 rpm for 10 minutes at 37° C. Three 100 ul aliquots of residual plasma were collected along with ultrafiltrate for bioanalysis.

Brain Binding Determination: MRS4322, sulfamethoxazole and warfarin were solubilized in DMSO and diluted in 1:1 acetonitrile:water to prepare 100 uM dialysis stock solutions. Pooled homogenized brains were pre-warmed for 60 minutes in a humidified, 5% $CO_2$ incubator maintained at 37° C. Three ml aliquots of brain homogenate were each spiked with MRS4322, sulfamethaxazole or warfarin using the 100 uM stock solutions for each compound resulting in final spiked concentrations of 1 uM. Spiked pooled brain homogenates were placed on a Nutator mixer in a humidified, 5% $CO_2$ incubator at 37° C. for 60 minutes. After 60 minutes, three 800 ul aliquots of each sample were added to Centrifree centrifugal filters. The filters were subjected to centrifugation at 2900 rpm for 10 minutes at 37 C. Aliquots of residual brain homogenate and ultrafiltrate were collected for bioanalysis.

Bioanalysis

Plasma and brain concentrations of MRS4322 in spiked plasma, brain homogenates and associated ultrafiltrates were determined by LC-MS/MS utilizing tolbutamide as an internal standard. Associated concentrations of sulfamethaxazole and warfarin were also determined by LC-MS/MS using standard conditions (data not shown). The following tables outline the LC and MS/MS conditions employed (Tables 15 and 16). Bioanalytical methods were identical for all matrices; standard curve statistics (e.g. Fit, Intercept, Slope, Correlation Coefficient) were determined for each matrix but were not significantly different and thus are not shown for each matrix.

TABLE 15

Bioanalytical Methods for MRS4322 for Determination of Plasma, Brain Homogenate, Plasma Ultrafiltrate and Brain Homogenate Ultrafiltrate Concentrations
Bioanalysis of Plasma, Brain Homogenates, Plasma Ultrafiltrate and Brain Homogenate Ultrafiltrate Samples

| System Components | | |
|---|---|---|
| Module | Manufacturer | Model |
| HPLC | Shimadzu | Prominence LC20AD Binary Pumps |
| Autosampler | CTC Leap | HTC PAL |
| Mass Spectrometer | AB Sciex | API 4000 |

| HPLC Method | |
|---|---|
| Column | Phenomenex Kinetex C18 (2.1 × 50 mm, 2.6 μm) |
| Elution | Gradient, 0.4 mL/min Mobile Phase A: 0.1% Formic acid in Water Mobile Phase B: 0.1% Formic acid in Acetontrile |

| Mass Spectrometer Conditions for MRS4322 |
|---|
| Peak Name: MRS4322 |
| Q1/Q3 Masses: |
| 324.10/182.00 Da |
| Peak Name: Tolbutamide |
| Q1/Q3 Masses: |
| 271.20/155.20 Da |

| Fit | Linear | Weighting | 1/x |
|---|---|---|---|
| Intercept | 0.0181 | | |
| Slope | 0.00192 | | |
| Correlation coefficient | 0.9988 | | |

For each tissue matrix, standard curves were created and LLOQ/ULOQ concentrations determined. The calibration range for the MRS4322 plasma concentration standard curves was 5-1000 nM. The calibration range for MRS4322 plasma ultrafiltrate standard curves was 5-1000 nM. The calibration range for MRS4322 brain homogenate and brain homogenate ultrafiltrate standard curves were 5-1000 nM and 5-1000 nM, respectively.

Results

Plasma binding and free fraction were determined for MRS4322 utilizing plasma ultrafiltration. Plasma binding was 21.6% for MRS4322; associated free fraction was 0.784 (Table 16). Binding of the study standards sulfamethaxazole and warfarin were consistent with literature values.

TABLE 16

Fraction Unbound and Binding of MRS4322 in Neonatal Pig Plasma

| | Fraction Unbound | | % Bound | | |
|---|---|---|---|---|---|
| Substrate | Mean | SD | Mean | SD | N |
| MRS4322 | 0.784 | 0.061 | 21.6 | 6.1 | 3 |
| Sulfamethoxazole | 0.606 | 0.016 | 39.4 | 1.6 | 2 |
| Warfarin | 0.0159 | 0.0021 | 98.4 | 0.2 | 3 |

* Plasma ultrafiltrate concentrations of MRS5698 were BLQ.

Brain binding and free fraction were determined for MRS4322 utilizing brain homogenate ultrafiltration. Brain binding was 74.7% for MRS4322; associated free fraction was 0.253 (Table 17). Binding of the study standards sulfamethaxazole and warfarin were consistent with literature values.

TABLE 17

Fraction Unbound and Binding of MRS4322 in Neonatal Pig Brain Homogenates

| Substrate | Fraction Unbound Mean | SD | % Bound Mean | SD | N |
|---|---|---|---|---|---|
| MRS4322 | 0.253 | 0.043 | 74.7 | 4.3 | 3 |
| Sulfamethoxazole | 0.309 | 0.029 | 69.1 | 2.9 | 3 |
| Warfarin | 0.189 | 0.006 | 81.1 | 0.6 | 3 |

These data indicate that for a given total plasma or brain concentration, substantial unbound drug concentrations of MRS4322 will be available in the brain for interaction with the adenosine A3 receptor. These findings are consistent with those also observed in the mouse.

Example 13: Pharmacological Characterization of MRS4322

The compound MRS4322 was investigated in competition binding studies at human and mouse $A_3$ adenosine receptors recombinantly expressed in Chinese hamster ovary (CHO) cells using cell membrane preparations. [$^3$H] NECA was employed as an $A_3$ agonist radioligand. The non-selective agonist NECA could be used because CHO cells do not natively express adenosine receptors. Concentration-dependent displacement of the radioligand by MR4322 was determined.

Additionally cAMP experiments were conducted at CHO cells recombinantly expressing human $A_3$ or mouse $A_3$ adenosine receptors, respectively. The non-selective agonist NECA was used as a control.

Results

MRS4322 showed a Kc value of 1490±410 nM at human $A_3$ receptors and a Kc value of 4940±974 nM at mouse $A_3$ receptors in radioligand binding studies versus [$^3$H]NECA.

In functional cAMP accumulation experiments in CHO cells expressing $A_3$ adenosine receptors, MRS4322 showed agonistic activity with an $EC_{50}$ value of 3630±370 nM at the human $A_3$ receptor, and an $EC_{50}$ value of 759±170 nM at the mouse $A_3$ receptor. $EC_{50}$ values of agonists at GPCRs are dependent on receptor expression levels. The human $A_3$ receptor cell line seems to have a lower expression level than the cell lines with the mouse $A_3$ receptors since higher $EC_{50}$ values are observed, which was also the case for the control agonist NECA.

TABLE 18

Affinities of agonists at adenosine receptors stably expressed in CHO cells determined in radioligand binding studies [$K_i$ ± SEM (nM)]

| | Receptor | |
|---|---|---|
| Agonist | Human $A_3$R [$^3$H]NECA | Mouse $A_3$R [$^3$H]NECA |
| MRS4322 | 1490 ± 410 | 4940 ± 974 |
| NECA | 6.18 $(K_D)^a$ | 15.1 $(K_D)^a$ |

[a]Alnouri M. W. et al. Selectivity is species-dependent: Characterization of standard agonists and antagonists at human, rat, and mouse adenosine receptors. *Purinergic Signal.* 2015, 11, 389-407. The same cell lines were used in the present and in the published study.

TABLE 19

Potencies of agonists at $A_3$ adenosine receptors stably expressed in CHO cells determined in cAMP accumulation assays

| Agonist | Human $A_3$R $EC_{50}$ ± SEM (nM) (efficacy at 100 μM concentration in % relative to maximal effect of NECA) | Mouse $A_3$R |
|---|---|---|
| MRS4322 | 3630 ± 370 | 759 ± 170 |
| | (70 ± 12) | (72 ± 18) |
| NECA | 41.8 ± 6.3 | 6.85 ± 0.88 |

Figure 17:
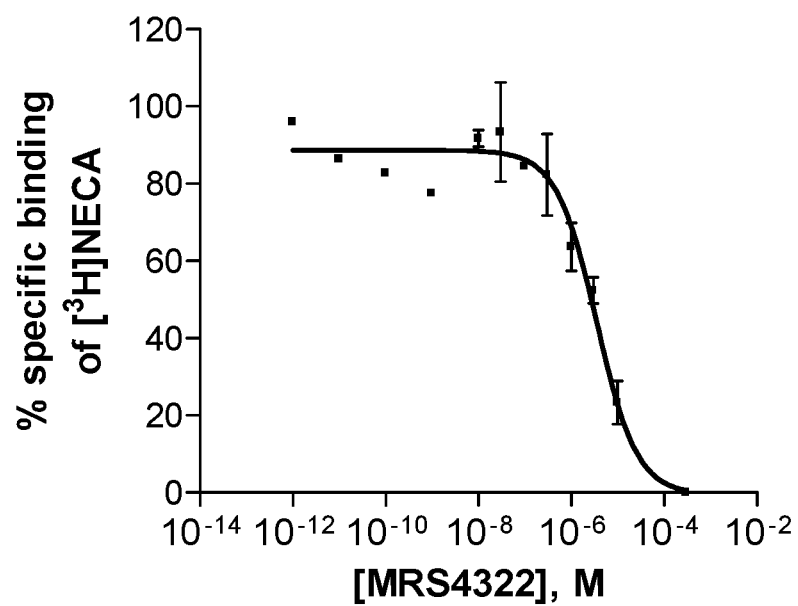
FIG. 17 shows competition binding experiments of MRS4322 versus the $A_3$ agonist radioligand [$^3$H]NECA (10 nM) at human $A_3$ receptors expressed in CHO cells. The calculated Kc-value for MRS4322 was 1490±410 nM.

FIG. 17 shows competition binding experiments of MRS4322 versus the $A_3$ agonist radioligand [$^3$H]NECA (10 nM) at human $A_3$ receptors expressed in CHO cells. The calculated $K_i$-value for MRS4322 was 1490±410 nM.

Figure 18:
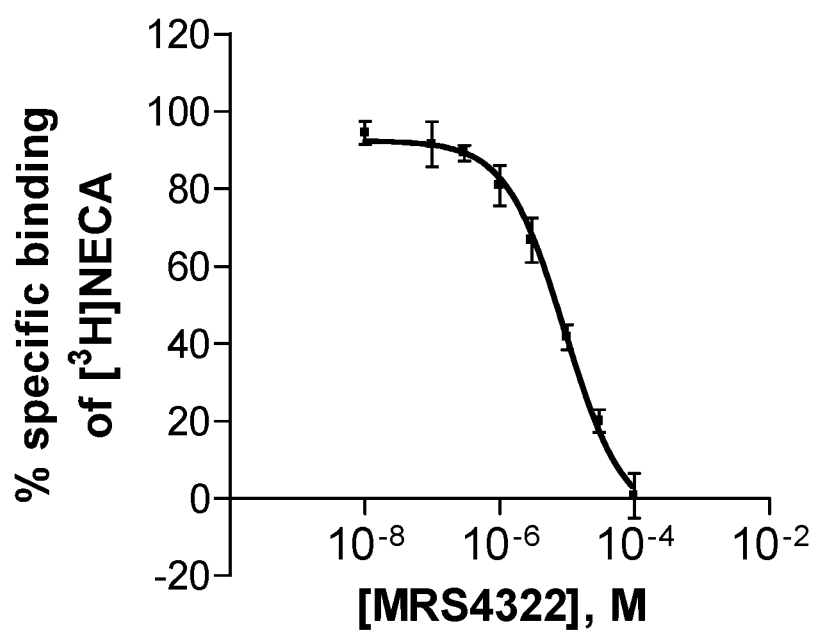
FIG. 18 shows competition binding experiments of MRS4322 versus the $A_3$ agonist radioligand [$^3$H]NECA (10 nM) at mouse $A_3$ receptors expressed in CHO cells. The calculated Kc-value for MRS4322 was 4940±974 nM.
Figure 19:
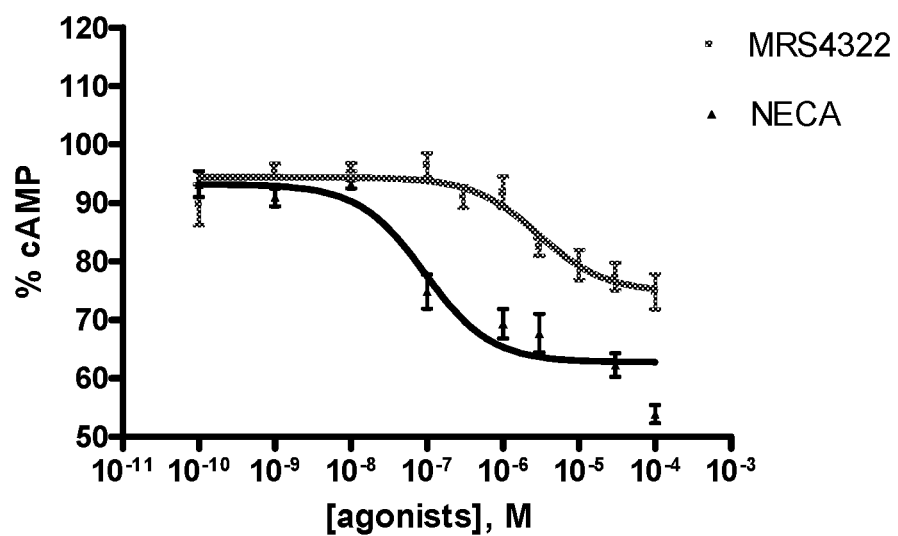
FIG. 19 shows cAMP accumulation experiments of MRS4322 and NECA at human $A_3$ receptors expressed in CHO cells. The calculated $EC_{50}$-value for MRS4322 was 3630±370 nM; for NECA an $EC_{50}$ value of 41.8±6.3 nM was determined.
Figure 20:
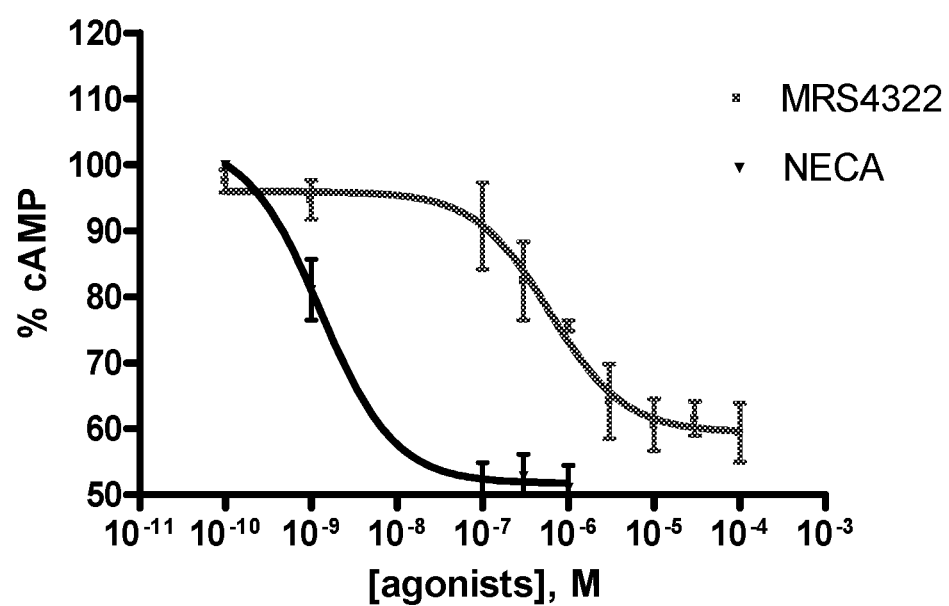
FIG. 20 shows cAMP accumulation experiments of MRS4322 and NECA at mouse $A_3$ receptors expressed in CHO cells. The calculated $EC_{50}$-value for MRS4322 was 759±170 nM; for NECA an $EC_{50}$ value of 6.85±0.88 nM was determined.

FIG. 18 shows competition binding experiments of MRS4322 versus the $A_3$ agonist radioligand [$^3$H]NECA (10 nM) at mouse $A_3$ receptors expressed in CHO cells. The calculated $K_i$-value for MRS4322 was 4940±974 nM. FIG. 19 shows cAMP accumulation experiments of MRS4322 and NECA at human $A_3$ receptors expressed in CHO cells. The calculated $EC_{50}$-value for MRS4322 was 3630±370 nM; for NECA an $EC_{50}$ value of 41.8±6.3 nM was determined. FIG. 20 shows cAMP accumulation experiments of MRS4322 and NECA at mouse $A_3$ receptors expressed in CHO cells. The calculated $EC_{50}$-value for MRS4322 was 759±170 nM; for NECA an $EC_{50}$ value of 6.85±0.88 nM was determined.

These results are lower than but related to the known binding data for MRS1873. Human $A_3$, Ki data: MRS1873 Ki=353 nM; EC50=803 nM, published in: J. Med. Chem. 2002 45:4471-4484. "Structural Determinants of A3 Adenosine Receptor Activation: Nucleoside Ligands at the Agonist/Antagonist Boundary," Gao, Z-G. et al.

An earlier paper lists the human $A_3$ Ki as 85 nM: Bioorganic and Medicinal Chemistry Letters 2001 11:1333-1337. "Ring-Constrained (N)-Methanocarba Nucleosides as Adenosine Receptor Agonists: Independent 5'-Uronamide and 2'-Deoxy Modifications," Lee, K. et al.

While a number of embodiments of this invention are described, it is understood that the particular examples described above may be altered using routine experimentation to provide other embodiments that utilize the compounds and methods of this invention. Therefore, it will be appreciated that the scope of this invention is to be defined only by the following claims rather than by the specific embodiments that have been provided.

We claim:

1. A method of treating an injury, disease, or condition selected from traumatic brain injury (TBI) and a stroke selected from ischemic stroke, hemorrhagic stroke, subarachnoid hemorrhage, cerebral vasospasm, and transient ischemic attacks (TIA), comprising administering to a patient in need thereof an effective amount of a compound selected from:

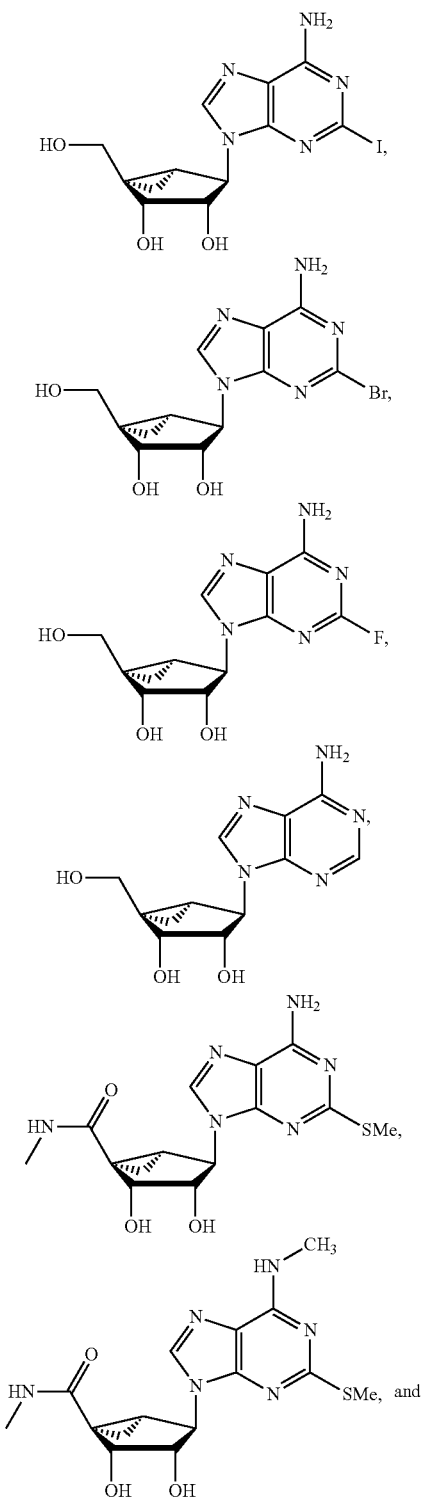

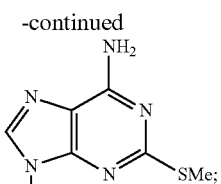

or a pharmaceutically acceptable salt thereof.

2. The method of claim 1, wherein the injury, disease, or condition is TBI.

3. The method of claim 2, wherein the TBI is selected from concussion, blast injury, combat-related injury, or a mild, moderate or severe blow to the head.

4. The method of claim 1, wherein the recovery period after the TBI or stroke is decreased as compared with an untreated patient.

5. The method of claim 1, wherein the compound is administered chronically to treat stroke during the time period after the injury has occurred as it resolves.

6. The method of claim 1, wherein the compound is selected from:

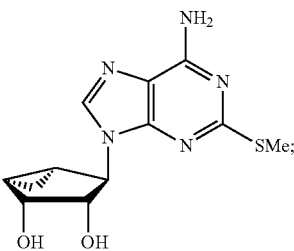

or a pharmaceutically acceptable salt thereof.

7. The method of claim 1, wherein the injury, disease, or condition is stroke and the compound or pharmaceutically acceptable salt thereof is administered within 48 hours of the stroke.

8. The method of claim 1, wherein the injury, disease, or condition is stroke and the compound or pharmaceutically acceptable salt thereof is administered within 24 hours of the stroke.

9. The method of claim 1, wherein the injury, disease, or condition is TBI and the compound or pharmaceutically acceptable salt thereof is administered within 48 hours of the TBI.

10. The method of claim 1, wherein the injury, disease, or condition is TBI and the compound or pharmaceutically acceptable salt thereof is administered within 24 hours of the TBI.

11. The method of claim 2, wherein neuroprotection or neurorestoration is increased in the patient as compared with an untreated patient.

* * * * *